US008940722B2

(12) United States Patent
Kinzel et al.

(10) Patent No.: US 8,940,722 B2
(45) Date of Patent: Jan. 27, 2015

(54) COMPOUNDS FOR MODULATION OF ORPHAN NUCLEAR RECEPTOR RAR-RELATED ORPHAN RECEPTOR-GAMMA (RORγ, NR1F3) ACTIVITY AND FOR THE TREATMENT OF CHRONIC INFLAMMATORY AND AUTOIMMUNE DISEASE

(75) Inventors: Olaf Kinzel, Heidelberg (DE); Christoph Steeneck, Dossenheim (DE); Gerald Kleymann, Bad Salzuflen (DE); Michael Albers, Mannheim-Seckenheim (DE); Thomas Hoffmann, Viernheim (DE); Claus Kremoser, Heidelberg (DE); Sanja Perovic-Ottstadt, Ginsheim-Gustavsburg (DE); Thomas Schlüter, Heidelberg (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 132 days.

(21) Appl. No.: 13/581,961

(22) PCT Filed: Feb. 28, 2011

(86) PCT No.: PCT/EP2011/000976
§ 371 (c)(1),
(2), (4) Date: Nov. 14, 2012

(87) PCT Pub. No.: WO2011/107248
PCT Pub. Date: Sep. 9, 2011

(65) Prior Publication Data
US 2013/0053380 A1    Feb. 28, 2013

Related U.S. Application Data

(60) Provisional application No. 61/309,062, filed on Mar. 1, 2010.

(30) Foreign Application Priority Data

Mar. 1, 2010    (EP) .................................... 10002069

(51) Int. Cl.
| | | |
|---|---|---|
| C07D 245/06 | (2006.01) |
| C07D 267/22 | (2006.01) |
| C07D 413/10 | (2006.01) |
| C07D 413/12 | (2006.01) |
| C07D 417/12 | (2006.01) |
| C07D 487/04 | (2006.01) |
| C07D 498/04 | (2006.01) |
| A61K 31/395 | (2006.01) |
| C07D 281/18 | (2006.01) |
| C07D 403/12 | (2006.01) |

(52) U.S. Cl.
CPC ............ *C07D 267/22* (2013.01); *C07D 245/06* (2013.01); *C07D 281/18* (2013.01); *C07D 403/12* (2013.01); *C07D 413/10* (2013.01); *C07D 413/12* (2013.01); *C07D 417/12* (2013.01); *C07D 487/04* (2013.01); *C07D 498/04* (2013.01)
USPC .......................................... 514/183; 540/476

(58) Field of Classification Search
USPC .......................................... 540/476; 514/183
See application file for complete search history.

(56) References Cited

FOREIGN PATENT DOCUMENTS

| | | |
|---|---|---|
| JP | 2006-56881 A | 3/2006 |
| WO | WO 99/32451 A1 | 7/1999 |

OTHER PUBLICATIONS

Kleinpeter et al. (Monatshefte fuer Chemie (1988), 119(2), 233-46). Abstract.*
He et al., "RORγt, a Novel Isoform of an Orphan Receptor, Negatively Regulates Fas Ligand Expression and IL-2 Production in T Cells," *Immunity*, 9:797-806, Dec. 1998.
Mohan et al., "Orphan Nuclear Receptor Modulators," *Current Topics in Medicinal Chemistry* 3(14): 1637-1647, 2003.
André et al., "A novel isoform of the orphan nuclear receptor RORβ is specifically expressed in pineal gland and retina," *Gene* 216: 277-283, 1998.
André et al., Disruption of retinoid-related orphan receptor β changes circadian behavior, causes retinal degeneration and leads to *vacillans* phenotype in mice, *The EMBO Journal* 117(14): 3867-3877, 1998.
Awasthi et al., "$T_h17$ cells: from precursors to players in inflammation and infection," *International Immunology* 21(5): 489-498, 2009.
Becker-André et al., "Identification of Nuclear Receptor mRNAs by RT-PCR Amplification of Conserved Zinc-finger Motif Sequences," *Biochemical and Biophysical Research Communications* 194(3): 1371-1379, Aug. 16, 1993.
Crome et al., "Translational Mini-Review Series on Th17 Cells: Function and regulation of human T helper 17 cells in health and disease," *Clinical & Experimenetal Immunology* 159: 109-119, 2009.
Dyer et al., "A Noncommercial Dual Luciferase Enzyme Assay System for Reporter Gene Analysis," *Analytical Biochemistry* 282: 158-161, 2000.

(Continued)

*Primary Examiner* — Bruck Kifle
(74) *Attorney, Agent, or Firm* — Seed IP Law Group PLLC

(57) ABSTRACT

The invention provides modulators for the orphan nuclear receptor RORγ and methods for treating RORγ mediated diseases by administrating these novel RORγ modulators to a human or a mammal in need thereof. Specifically, the present invention provides compounds of Formula (1) and the enantiomers, diastereomers, tautomers, solvates and pharmaceutically acceptable salts thereof.

(1)

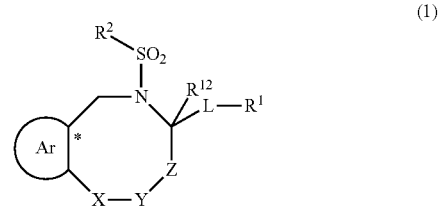

10 Claims, 4 Drawing Sheets

(56) References Cited

OTHER PUBLICATIONS

Eberl et al., "The role of the nuclear hormone receptor RORγt in the development of lymph nodes and Peyer's patches," *Immunological Reviews 195*: 81-90, 2003.

Eberl et al., "Thymic Origin of Intestinal αβ T Cells Revealed by Fate Mapping of RORγt+ Cells," *Science 305*: 248-251, Jul. 9, 2004.

Evans, "The Steroid and Thyroid Hormone Receptor Superfamily," *Science 240*: 889-895, May 13, 1988.

Giguère et al., "The Orphan Nuclear Receptor RORα (RORA) Maps to a Conserved Region of Homology on Human Chromosome 15q21-q22 and Mouse Chromosome 9," *Genomics 28*: 596-598, 1995.

Gu et al., "Interleukin 10 suppresses Th17 cytokines secreted by macrophages and T cells," *Eur. J Immunol. 38*: 1807-1813, 2008.

He et al., "Down-Regulation of the Orphan Nuclear Receptor RORγt Is Essential for T Lymphocyte Maturation," *J. Immunol. 164*: 5668-5674, 2000.

Houck et al., "T0901317 is a dual LXR/FXR agonist," *Molecular Genetics and Metabolism 83*: 184-187, 2004.

Ivanov et al., "The Orphan Nuclear Receptor RORγt Directs the Differentiation Program of Proinflammatory IL-17+ T Helper Cells," *Cell 126*: 1121-1133, Sep. 22, 2006.

Kallen et al., "X-Ray Structure of the hRORα LBD at 1.63 Å: Structural and Functional Data that Cholesterol or a Cholesterol Derivative Is the Natural Ligand of RORα," *Structure 10*: 1697-1707, Dec. 2002.

Kumar et al., "The Benzenesulfoamide T0901317 [N-(2,2,2-Trifluoroethyl)-N-[4[2,2,2-trifluoro-1-hydroxy-1-(trifluoromethyl)ethyl]phenyl]benzenesulfonamide] Is a Novel Retinoic Acid Receptor-Related Orphan Receptor-α/γ Inverse Agonist," *Mol. Pharmacol. 77*(2): 228-236, 2010.

Lau et al., "The Orphan Nuclear Receptor, RORα, Regulates Gene Expression That Controls Lipid Metabolism: Staggerer (SG/SG) Mice are Resistant to Diet-induced Obesity," *Journal of Biological Chemistry 283*(26): 18411-18421, Jun. 27, 2008.

Mangelsdorf et al., "The Nuclear Receptor Superfamily: The Second Decade," *Cell 83*: 835-839, Dec. 15, 1995.

McKenna et al., "Nuclear Receptor Coregulators: Cellular and Molecular Biology," *Endocrine Reviews 20*(3): 321-344, 1999.

Missbach et al., "Thiazolidine Diones, Specific Ligands of the Nuclear Receptor Retinoid Z Receptor/Retinoid Acid Receptor-related Orphan Receptor α with Potent Antiarthritic Activity," *Journal of Biological Chemistry 271*(23): 13515-13522, Jun. 7, 1996.

Stehlin-Gaon et al., All-*trans* retinoic acid is a ligand for the orphan nuclear receptor RORβ, *Nature Structural Biology 10*(10): 820-825, Oct. 2003.

Sun et al., "Requirement for RORγ in Thymocyte Survival and Lymphoid Organ Development," *Science 288*: 2369-2373, Jun. 30, 2000.

Tesmer et al., "Th17 cells in human disease," *Immunological Reviews 223*: 87-113, 2008.

Tilley et al., "Retinoid-Related Orphan Receptor γ Controls Immunoglobulin Production and Th1/Th2 Cytokine Balance in the Adaptive Immune Response to Allergen," *The Journal of Immunology 178*: 3208-3218, 2007.

Vanacker et al., "Transcriptional Activities of the Orphan Nuclear Receptor ERRα (Estrogen Receptor-Related Receptor-α)," *Molecular Endocrinology 13*: 764-773, 1999.

Villey et al., "RORγT, a thymus-specific isoform of the orphan nuclear receptor RORγ/TOR, is up-regulated by signaling through the pre-T cell receptor and binds to the TEA promoter," *Eur. J. Immunol. 29*: 4072-4080, 1999.

Wang et al., "Modulation of Retinoic Acid Receptor-related Orphan Receptor α and γ Activity by 7-Oxygenated Sterol Ligands," *Journal of Biological Chemistry 285*(7): 5013-5025, Feb. 12, 2010.

Wiesenberg et al., "Transcriptional activation of the nuclear receptor RZRα by the pineal gland hormone melatonin and identification of CGP 52608 as a synthetic ligand," *Nucleic Acids Research 23*(3): 327-333, 1995.

Wilson et al., "The Orphan Receptors NGFI-B and Steroidogenic Factor 1 Establish Monomer Binding as a Third Paradigm of Nuclear Receptor-DNA Interaction," *Molecular and Cellular Biology 13*(9): 5794-5804, Sep. 1993.

Xue et al., "Crystal structure of the PXR-T1317 complex provides a scaffold to examine the potential for receptor antagonism," *Bioorg. Med. Chem.*(2007), doi:10.1016/j.bmc.2006.12.026, 11 pages.

Zhou et al., "Transcriptional regulatory networks in Th17 cell differentiation," *Curr. Opin. Immunol. 21*(2): 146-152, Apr. 2009.

Rujirawanich et al., "Substituted 1,4-Benzoxazepines, 1,5-Benzoxazocines, and N- and S-Variants," *Organic Letters 11*(23): 5494-5496, Oct. 30, 2009.

European Search Report mailed Aug. 30, 2010, for EP10002069.2, 6 pages.

Kleinpeter et al., "Intramolecular Flexibility of Heteroanalogous Benzo- and Dibenzo-1,5,cyclooctadienes," *Monatshefte für Chemie 119*: 233-246, 1988.

* cited by examiner

Figure 1
Figure 1a
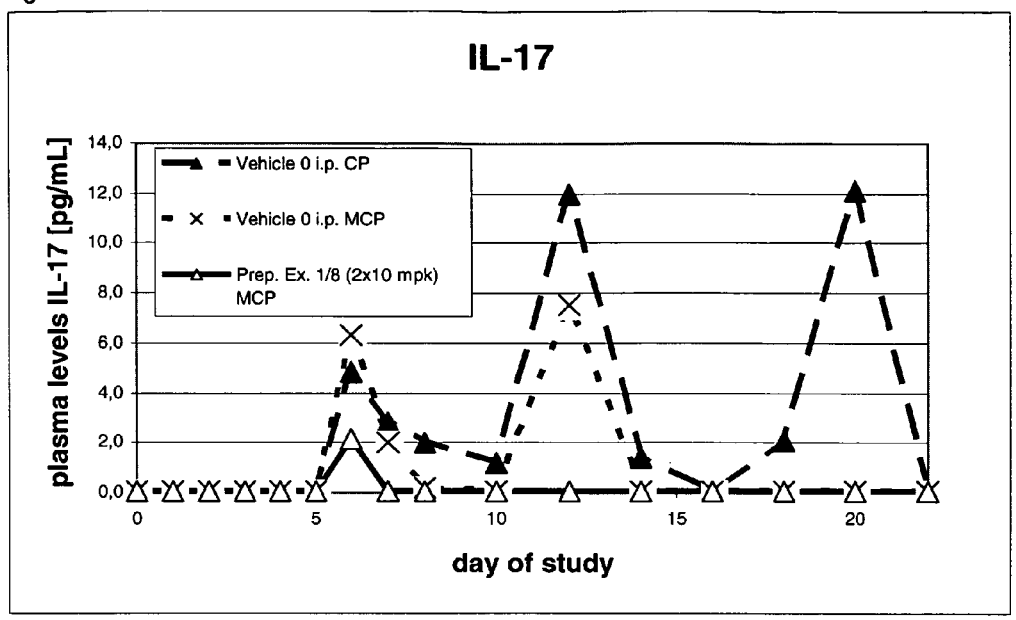
Figure 1b
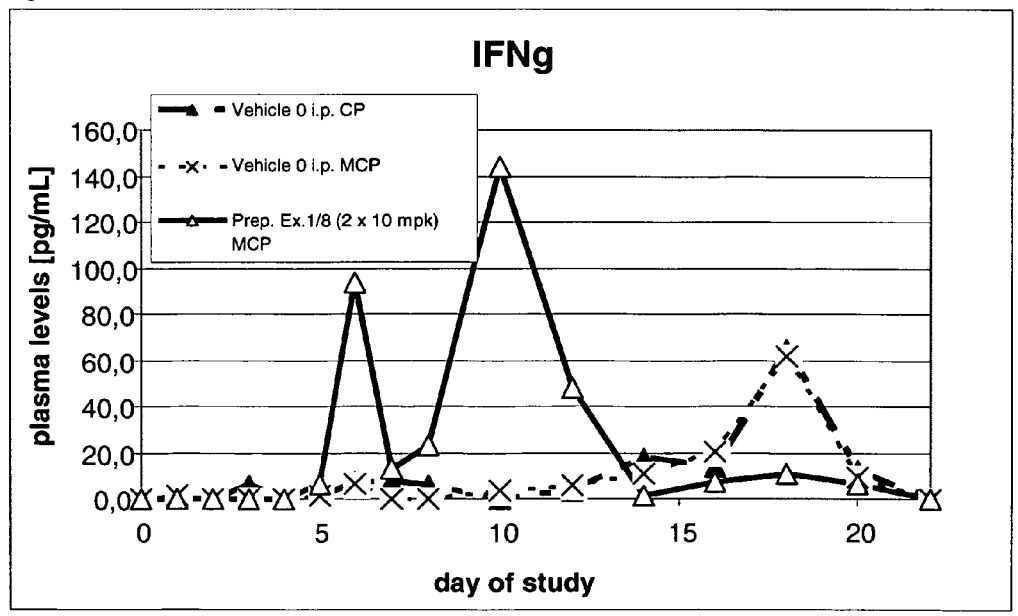

Figure 2
Figure 2a
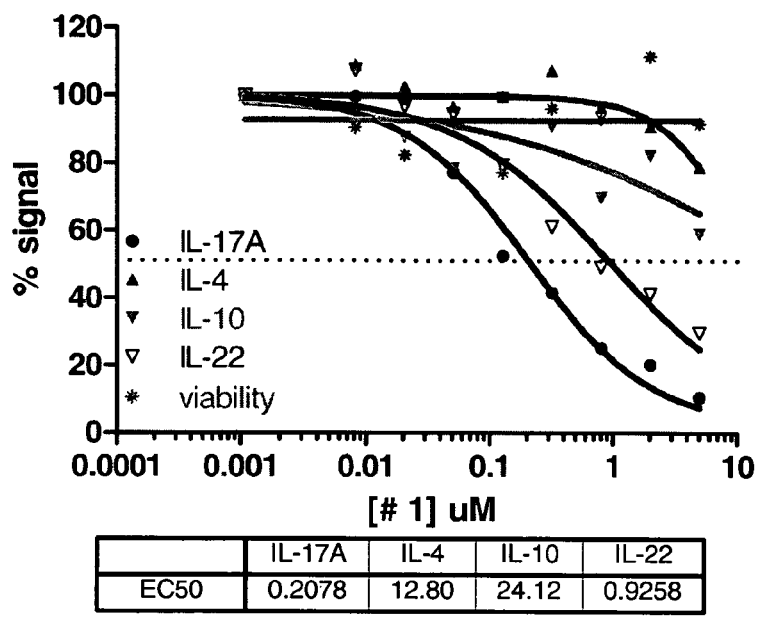
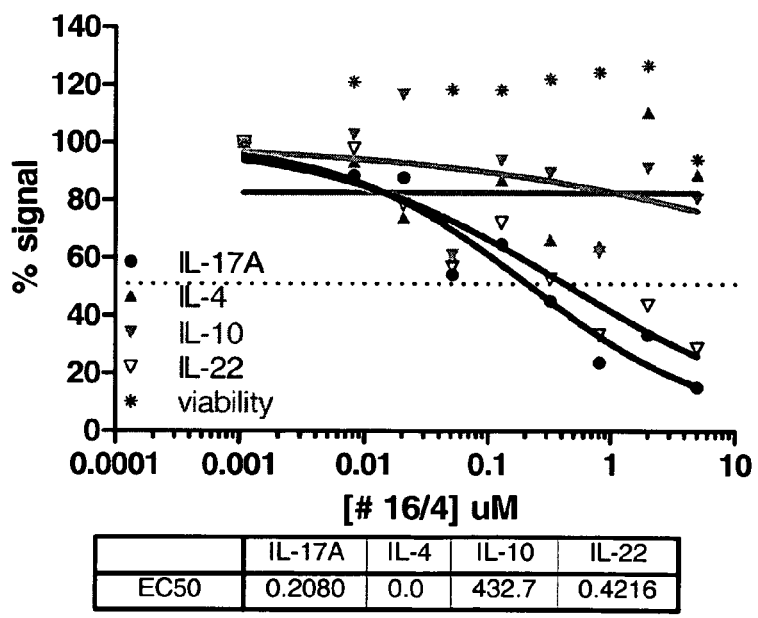

COMPOUNDS FOR MODULATION OF ORPHAN NUCLEAR RECEPTOR RAR-RELATED ORPHAN RECEPTOR-GAMMA (RORγ, NR1F3) ACTIVITY AND FOR THE TREATMENT OF CHRONIC INFLAMMATORY AND AUTOIMMUNE DISEASE

This application is a U.S. National Phase Application of International Application No. PCT/EP2011/000976, filed Feb. 28, 2011, which claims priority to European Patent Application No. EP 10002069.2, filed Mar. 1, 2010, and U.S. Provisional Patent Application No. 61/309,062 filed Mar. 1, 2010. These applications are incorporated herein by reference in their entireties.

The invention provides modulators for the orphan nuclear receptor RORγ and methods for treating RORγ mediated chronic inflammatory and autoimmune diseases by administrating these novel RORγ modulators to a human or a mammal in need thereof.

The retinoid-receptor related orphan receptors consist of three family members, namely RORα (Beckerandre et al., *Biochem. Biophys. Res. Commun.* 1993, 194:1371), RORβ (Andre et al., *Gene* 1998, 516:277) and RORγ (He et al., *Immunity* 1998, 9:797) and constitute the NR1F (ROR/RZR) subgroup of the nuclear receptor superfamily (Mangelsdorf et al., *Cell* 1995, 83:835).

The nuclear receptor superfamily shares common modular structural domains consisting of a hypervariable N-terminal domain, a conserved DNA binding domain (DBD), a hinge region, and a conserved ligand-binding domain (LBD). The DBD targets the receptor to specific DNA sequences (nuclear hormone response elements or NREs), and the LBD functions in the recognition of endogenous or exogenous chemical ligands. A constitutive transcriptional activation domain is found at the N-terminus (AF1) and a ligand regulated transcriptional activation domain is embedded within the C-terminal LBD of typical NRs. The nuclear receptors can exist in a transcriptional activating or repressing state when bound to their target NREs. The basic mechanism of gene activation involves ligand dependent exchange of co-regulatory proteins, namely co-activators and co-repressors (McKenna et al., *Endocrine Rev.* 1999, 20:321). A NR in the repressing state is bound to its DNA recognition element and is associated with co-repressor proteins that recruit histone-deacetylases (HDACs). In the presence of an agonist, co-repressors are exchanged for coactivators that recruit transcription factors, which contribute to assembling of a chromatin-remodeling complex, which relieves transcriptional repression and stimulates transcriptional initiation via histone acetylation. The AF-2 domain of the LBD acts as a ligand dependant molecular switch presenting interaction surfaces for co-repressor or coactivator proteins and providing with a conserved mechanism for gene activation or repression that is shared by the members of the nuclear receptor superfamily.

The members of the NR1F family of nuclear receptors (such as RORγ) have been considered to be constitutively active transcription factors in the absence of known ligands, which is similar to the estrogen-related receptor alpha (Vanacker et al., *Mol. Endocrinol.* 1999, 13:764). Most recently, 7-oxygenated oxysterols were identified to be high affinity ligands for RORα and RORγ (Wang et al., *J. Biol. Chem.* 2010, 285:5013). 7-Hydroxycholesterol is a key metabolite during the conversion of cholesterol into bile acids, but to date it is not clear whether it is a true endogenous ligand for the RORs. In any case it can be expected that inverse agonists of RORγ should reduce the transcriptional activity of RORγ and influence the biological pathways controlled by RORγ.

The RORs are expressed as isoforms arising from differential splicing or alternative transcriptional start sites. So far, isoforms have been described that differ only in their N-terminal domain (A/B-domain). In humans, four different RORα isoforms have been identified (RORα 1-4) while only two isoforms are known for both RORβ (1 and 2) and RORγ (1 and 2) (Andre et al., *Gene* 1998, 216:277; Villey et al., *Eur. J. Immunol.* 1999, 29:4072). RORγ is used herein as a term describing both, RORγ1 and/or RORγ2.

The ROR isoforms show different tissue expression patterns and regulate different target genes and physiological pathways. For example, the RORγ2 (also called RORγt) is highly restricted to $CD4^+CD8^+$ thymocytes and to interleukin-17 (IL-17) producing T cells while other tissues express RORγ1 (Eberl et al., *Science* 2004, 305:248, Zhou and Littmann, *Curr. Opin. Immunol.* 2009, 21:146).

RORs exhibit a structural architecture that is typical of nuclear receptors. RORs contain four major functional domains: an amino-terminal (A/B) domain, a DNA-binding domain (DBD), a hinge domain, and a ligand-binding domain (LBD) (Evans et al., *Science* 1988, 240:889). The DBD consists of two highly conserved zinc finger motifs involved in the recognition of ROR response elements (ROREs) which consist of the consensus motif AGGTCA preceded by an AT-rich sequence (Andre et al., *Gene* 1998, 216:277) which is similar to that of the nuclear receptors Rev-ErbAα and Rev-Erbβ (NR1D1 and D2, respectively) (Giguere et al., *Genomics* 1995, 28:596). These recognition elements do also show high similarity to those identified for the estrogen related receptors and in particular ERRα (ERRs, NR3B1, -2, -3) (Vanacker et al., *Mol. Endocrinol.*, 1999, 13:764), steroidogenic factor 1 (SF-1, NR5A) and NGFI-B (NR4A1, -2, -3) (Wilson et al., *Mol. Cell. Biol.* 1993, 13:5794).

RORα is highly expressed in different brain regions and most highly in cerebellum and thalamus. RORα knock-out mice show ataxia with strong cerebellar atrophy, highly similar to the symptoms displayed in the so-called staggerer mutant mouse ($ROR\alpha^{sg/sg}$). This mouse carries mutations in RORα that results in a truncated RORα which does not contain a LBD (Hamilton et al., *Nature* 1996, 379:736).

Analysis of $ROR\alpha^{sg/sg}$ staggerer-mice have revealed a strong impact on lipid metabolism beyond the CNS defects, namely significant decreases in serum and liver triglyceride, reduced serum HDL cholesterol levels and reduced adiposity. SREBP1c and the cholesterol transporters ABCA1 and ABCG1 are reduced in livers of staggerer mice and CHIP analysis suggest that RORα is directly recruited to and regulates the SREBP1c promoter. In addition, PGC1α, PGC1β, lipin1 and β2-adrenergic receptor were found to be increased in tissues such as liver or white and brown adipose tissue, which may help to explain the observed resistance to diet-induced obesity in staggerer mice (Lau et al., *J. Biol. Chem.* 2008, 283:18411).

RORβ expression is mainly restricted to the brain and most abundantly found in the retina. RORβ knock-out mice display a duck-like gait and retinal degeneration which leads to blindness (Andre et al., *EMBO J.* 1998, 17:3867). The molecular mechanisms behind this retinal degeneration are still poorly understood.

RORγ (particularly RORγ2) null-mutant mice lack lymph nodes and Peyer's patches (Eberl and Littmann, *Immunol., Rev.* 2003, 195:81) and lymphatic tissue inducer (LTi) cells are completely absent from spleen mesentery and intestine. In addition, the size of the thymus and the number of thymocytes is greatly reduced in RORγ null mice (Sun et al., *Science* 2000, 288:2369) due to a reduction in double-positive $CD4^+$ $CD8^+$ and single positive $CD4^-CD8^+$ or $CD4^+CD8^-$ cells suggesting a very important role of RORγ2 in thymocyte development.

Thymocyte development follows a complex program involving coordinated cycles of proliferation, differentiation, cell death and gene recombination in cell populations dedicated by their microenvironment. Pluripotent lymphocyte progenitors migrating from fetal liver or adult bone marrow to the thymus are being committed to the T-cell lineage. They develop through a series of steps from $CD4^-CD8^-$ double negative cells to $CD4^+CD8^+$ cells and those with low affinity towards self-MHC peptides are eliminated by negative selection. These develop further into $CD4^-CD8^+$ (killer) or $CD4^+$ $CD8^-$ (helper) T-cell lineages. RORγ2 is not expressed in double negative and little expressed in immature single negative thymocytes (He et al., *J. Immunol.* 2000, 164:5668), while highly upregulated in double-positive thymocytes and downregulated during differentiation in single-positive thymocytes. RORγ deficiency results in increased apoptosis in $CD4^+CD8^+$ cells and the number of peripheral blood thymocytes is decreased by 6-fold (10-fold $CD4^+$ and 3-fold $CD8^+$ thymocytes).

Recent experiments in a model of ovalbumin (OVA)-induced inflammation in mice, as a model for allergic airway disease, demonstrated a severe impairment of the development of the allergic phenotype in the RORγ KO mice with decreased numbers of $CD4^+$ cells and lower Th2 cytokine/chemokine protein and mRNA expression in the lungs after challenge with OVA (Tilley et al., *J. Immunol.* 2007, 178: 3208). IFN-γ and IL-10 production were increased in splenocytes following re-stimulation with the OVA antigen compared to wt splenocytes suggesting a shift towards a Th1 type immune response on cost of a reduction of Th2 type response. This suggests that down-modulation of RORγ transcriptional activity with a ligand could result in a similar shift of the immune response towards a Th1 type response, which could be beneficial in the treatment of certain pulmonary diseases like asthma or allergic inflammatory conditions.

T-helper cells were previously considered to consist of Th1 and Th2 cells. However, a new class of Th cells, the Th17 cells, which produce IL-17, were also identified as a unique class of T-cells that are considered to be pro-inflammatory. They are recognized as key players in autoimmune and inflammatory diseases since IL-17 expression has been associated with many inflammatory diseases such as rheumatoid arthritis, systemic lupus erythematosis (SLE) and allograft rejection. (Tesmer et al., *Immunol. Rev.* 2008, 223:87).

RORγ2 is exclusively expressed in cells of the immune system and has been identified as a master regulator of Th17 cell differentiation. Expression of RORγ2 is induced by TGF-beta or IL-6 and overexpression of RORγ2 results in increased Th17 cell lineage and IL-17 expression. RORγ2 KO mice show very little Th17 cells in the intestinal lamina propria and demonstrate an attenuated response to challenges that usually lead to autoimmune disease (Ivanov et al., *Cell* 2006, 126: 1121).

Inhibition of IL-17 production via inhibition of Th17 cell development may also be advantageous in atopic dermatitis and psoriasis where IL-17 is deeply involved. Interestingly, recent evidence was presented that IL-10 suppresses the expression of IL-17 secreted by both, macrophages and T-cells. In addition, the expression of the Th17 transcription factor RORγ2 was suppressed (Gu et al., *Eur. J. Immunol.* 2008, 38:1807). Moreover, IL-10 deficient mice provide a good model for inflammatory bowel disease (IBD) where a shift towards a Th1 type inflammatory response is frequently observed. Oral IL-10 delivery poses a potential treatment option for IBD.

The proinflammatory actions of IL-17 producing Th17 cells are counteracted by another T-helper cell type, so-called regulatory T-cells or Tregs. Naïve T cells are differentiated into Tregs upon stimulation by TGFβ. This results in upregulation of the transcriptional modulator FoxP3 resulting in $CD4^+FoxP3^+$ Tregs. In case the naïve T-cells are co-stimulated by IL-6, FoxP3 expression is suppressed and RORγt expression is induced. These $CD4^+FoxP3^-RORγt^+$ T-helper cells then differentiate into IL-17 producing Th17 cells. (reviewed in Awasthi and Kuchroo, *Int. Immunol.* 2009, 21:489, and Zhou and Littmann, *Curr. Opin. Immunol.* 2009, 21:146). Several lines of evidence suggest that these Th17 cells are responsible for the etiology of a whole range of autoimmune diseases such as multiple sclerosis, rheumatoid arthritis, ankylosing spondylitis, psoriasis, Crohn's disease and other types of inflammatory bowel disease, lupus erythematosus and asthma. The severity of disease seems to correlate with the presence of IL-17$^+$ Th17 cells and it is believed that interception of RORγt by a small molecule inverse agonist or antagonist should result in a reduction of these IL-17$^+$ Th17 cells ultimately leading to alleviation of disease symptoms and outcome (Crome et al., *Clin. Exp. Immunol.* 2010, 159: 109).

Liqands for the RORs:

It was reported that cholesterol and its sulfated derivatives might function as RORα ligands and in particular cholesterol-sulfate could restore transcriptional activity of RORα in cholesterol-depleted cells (Kallen et al., *Structure* 2002, 10:1697). Previously, melatonin (Missbach et al., *J. Biol. Chem.* 1998, 271:13515) and thiazolidinediones were suggested to bind to RORα (Wiesenberg et al., *Nucleic Acid Res.* 1995, 23:327). However, none of these have been shown to be functional ligands of RORα or of any other of the RORs. Certain retinoids including all-trans retinoid acid have been demonstrated to bind to RORβ and function as partial antagonists for RORβ but not RORα (Stehlin-Gaon et al., *Nat. Struct. Biol.* 2003, 10:820).

Recently, 7-oxygenated sterols such as 7-hydroxy-cholesterol and 7-keto-cholesterol were identified as highly potent modulators of RORγ activity (Wang et al., *J. Biol. Chem.* 2010, 285:5013) in in vitro assays. The same group of investigators also found that a known LXR agonist, T0901317 ([N-(2,2,2-trifluoroethyl)-N-[4-[2,2,2-trifluoro-1-hydroxy-1-(trifluoromethyl)ethyl]phenyl]-benzenesulfonamide]) acts as a RORγ inverse agonist at submicromolar potency (Kumar et al., *Mol. Pharmacol.* 2010, 77:228). In neither case, however, in vivo data were obtained that demonstrate a beneficial impact of these RORγ modulating compounds. In case of the 7-oxysterols their endogenous presence as metabolites naturally produced by the body itself as well as their rapid turn-over and their biological activities on many cellular proteins prevent a meaningful animal study that allows drawing conclusions on the role of RORγ. In case of the T0901317 its polypharmacodynamic properties, acting on at least six different nuclear receptors (LXRα/β, FXR, PXR, RORα/γ) prevents its usefulness as a drug candidate for the development in an autoimmune disease application (Houck et al., *Mol. Genet. Metab.* 2004, 83:184; Xue et al., *Bioorg. Med. Chem.* 2007, 15:2156).

SUMMARY OF THE DESCRIPTION

It is therefore the object of the present invention to provide compounds, which bind to the orphan nuclear receptors RORγ1 and/or RORγ2 and, thus, to open new methods for treating diseases associated with the modulation of RORγ, such as autoimmune diseases, inflammatory skin diseases or multiple sclerosis.

This object is solved by the surprising discovery of small molecule ligands for the human RORγ.

Thus, the present invention provides RORγ modulators, which can be used for treating or preventing a disease or disorder associated with the inactivation or activation of the RORγ receptor.

Furthermore, the present invention relates to compounds identified by the methods described herein.

The present invention relates to a RORγ modulator for use in the treatment or prophylaxis of a disease or disorder associated with the inhibition or activation of RORγ.

When treating the disease or disorder associated with the modulation of the RORγ receptor, the activity of said receptor is preferably reduced.

Preferably, the disease or disorder is selected from the group consisting of autoimmune diseases. Autoimmune diseases comprise a group of diseases with a similar etiology of an overshooting immune response against endogenous targets resulting in chronic inflammation and physical disabilities or other severe symptoms. Autoimmune diseases comprise e.g. rheumatoid arthritis, ankylosing spondylitis, lupus erythematosus, psoriasis, atopic eczema, inflammatory bowel diseases such as Crohn's disease, asthma, multiple sclerosis, type 1 diabetes and amyotrophic lateral sclerosis.

JP-A-2006/056881 describes 6 to 9-membered heterocyclic fused pyrimidine compounds as TGF receptor agonists for the treatment of e.g. heart failure or myocardial infarction. As shown exemplarily in Formula (A), all of the examples in JP-A-2006/056881 bear a cyclic structure as substituent at the atom position neighbouring the bridgehead atom "*".

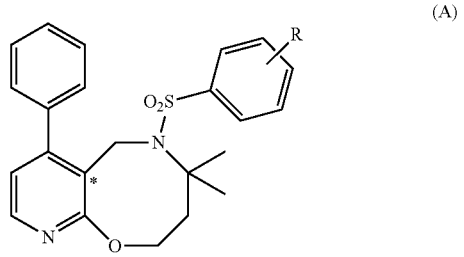

(A)

BRIEF DESCRIPTION OF THE FIGURES

FIG. 1 in general shows the daily development of plasma key cytokine levels after immunisation with CFA+PTX alone ("CP"), with MOG peptide+CFA+PTX ("MCP") and dosing of vehicle and with MOG peptide+CFA+PTX ("MCP") and dosing of 2×10 mg/(kg×day) of the compound of Preparative Example 1/8.

FIG. 1a shows the development of interleukin-17 levels upon compound of Preparative Example 1/8 dosing.

FIG. 1b describes the development of interferon gamma levels upon compound of Preparative Example 1/8 dosing.

FIG. 2a and FIG. 2b show Preparative Examples of compounds according to Formula (1) with selective inhibitory effects on Th17-cytokine production in activated human PBMCs.

Figure 1C:
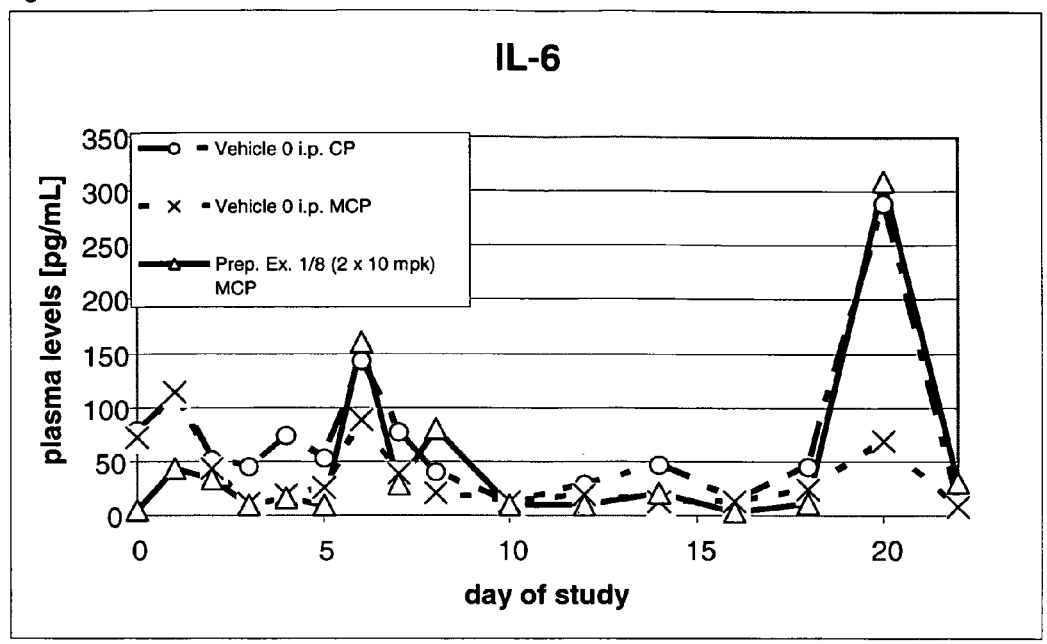
FIG. 1c shows the development of interleukin-6 levels upon compound of Preparative Example 1/8 dosing.

The present invention provides compounds to be used in the treatment of diseases or disorders associated with the inactivation or activation of the RORγ receptor. Specifically, the present invention provides compounds of Formula (1)

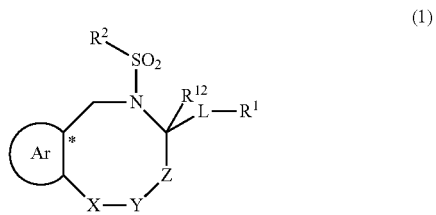

(1)

and the enantiomers, diastereomers, tautomers, solvates and pharmaceutically acceptable salts thereof,
wherein:
$R^1$ is hydrogen; $C_{1-12}$-alkyl; $C_{1-12}$-alkenyl; $C_{1-12}$-alkynyl; $C_{3-10}$-cycloalkyl; $COOC_{1-6}$-alkyl; $CONR^{10}R^{11}$; CN; $NR^{10}R^{11}$, a saturated 3-10 membered heterocycle containing 1 or 2 heteroatoms independently selected from the group consisting of N, O and S; a 5-10 membered mono- or bicyclic heteroaromatic ring system containing 1, 2, 3 or 4 heteroatoms independently selected from the group consisting of N, O and S; or a 6-10 membered mono- or bicyclic aromatic ring system
  wherein the alkyl, the alkenyl, the alkynyl, the cycloalkyl and the heterocyclic groups are unsubstituted or substituted by 1, 2 or 3 substituents independently selected from the group consisting of hydroxy, oxo, halogen, cyano, halo-$C_{1-6}$-alkyl, O—$C_{1-6}$-alkyl, O-(halo-$C_{1-6}$-alkyl), COOH, $CONR^{10}R^{11}$ and $NR^{10}R^{11}$;
  or wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{1-12}$-alkyl, $C_{3-6}$-cycloalkyl, O—$C_{1-6}$-alkyl, O-(halo-$C_{1-6}$-alkyl), COOH, $CO_2NR^{10}R^{11}$, $NR^{10}R^{11}$, a 5-10 membered mono- or bicyclic heteroaromatic ring system containing 1, 2 or 3 heteroatoms independently selected from the group consisting of N, O and S, a 6-10 membered mono- or bicyclic aromatic ring system, and a saturated 3-8 membered heterocycle containing 1 or 2 heteroatoms independently selected from the group consisting of N, O and S
    wherein the ring systems, the alkyl and the cycloalkyl groups are independently from each other unsubstituted or substituted by 1, 2 or 3 substituents selected from the group consisting of hydroxy, oxo, halogen, cyano, $C_{1-6}$-alkyl, halo-$C_{1-6}$-alkyl, O—$C_{1-6}$-alkyl, O-(halo-$C_{1-6}$-alkyl) and COOH;
  or wherein the heteroaromatic and the aromatic ring systems are fused with a saturated 5-8 membered heterocycle containing 1, 2, or 3 heteroatoms independently selected from the group consisting of N, O and S
    wherein the fused ring system is unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, $CO_2NR^{10}R^{11}$ and $NR^{10}R^{11}$;
$R^2$ is $C_{1-12}$-alkyl; $C_{3-10}$-cycloalkyl; a saturated 3-10 membered heterocycle containing 1 or 2 heteroatoms independently selected from the group consisting of N, O and S; a 5-10 membered mono- or bicyclic heteroaromatic ring system containing 1, 2 or 3 heteroatoms independently selected from the group consisting of N, O and S; or a 6-10 membered mono- or bicyclic aromatic ring system wherein the alkyl, the cycloalkyl and the heterocyclic groups are unsubstituted or substituted by 1, 2 or 3 substituents independently selected from the group consisting of hydroxy, oxo, halogen, cyano, halo-$C_{1-6}$-alkyl, O—$C_{1-6}$-alkyl, O-(halo-$C_{1-6}$-alkyl), COOH, CONR$^{10}$R$^{11}$ and NR$^{10}$R$^{11}$;

and wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{3-6}$-cycloalkyl, O—$C_{1-6}$-alkyl, O-(halo-$C_{1-6}$-alkyl), O—$C_{1-6}$-alkyl substituted with a saturated 5 or 6 membered heterocycle containing 1 or 2 heteroatoms independently selected from the groups consisting of N, O and S, COOH, CO$_2$($C_{1-6}$-alkyl), CONR$^{10}$R$^{11}$, NR$^{10}$R$^{11}$, SO$_2$($C_{1-6}$-alkyl), a saturated 3-10 membered heterocycle containing 1 or 2 heteroatoms independently selected from the group consisting of N, O and S, a 5-10 membered mono- or bicyclic heteroaromatic ring system containing 1, 2 or 3 heteroatoms independently selected from the group consisting of N, O and S, and a 6-10 membered mono- or bicyclic aromatic ring system wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, CO$_2$NR$^{10}$R$^{11}$ and NR$^{10}$R$^{11}$;

or wherein the heteroaromatic and the aromatic ring systems are fused with a saturated 5-8 membered heterocycle containing 1, 2, or 3 heteroatoms independently selected from the group consisting of N, O and S wherein the fused ring system is unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, CO$_2$NR$^{10}$R$^{11}$ and NR$^{10}$R$^{11}$;

L is —(CR$^6_2$)$_x$—, —NR$^7$—(CR$^6_2$)$_x$—, —(CR$^6_2$)$_x$—NR$^7$—, —(CR$^6_2$)$_x$—O—, or —(CR$^6_2$)$_x$—O—(CR$^6_2$)$_x$;

R$^6$ is independently H, $C_{1-6}$-alkyl, halo-$C_{1-6}$-alkyl or halogen;

R$^7$ is H, $C_{1-6}$-alkyl, halo-$C_{1-6}$-alkyl and hydroxy-$C_{1-6}$-alkyl;

R$^{10}$ and R$^{11}$ in each occurrence are independently selected from hydrogen, $C_{1-6}$-alkyl, halo-$C_{1-6}$-alkyl, $C_{3-6}$-cycloalkyl; or R$^{10}$ and R$^{11}$ when taken together with the nitrogen to which they are attached complete a 3- to 8-membered ring containing carbon atoms and optionally containing a heteroatom selected from O, S, SO, SO$_2$ or NR$^7$ and which is optionally substituted one or more with halogen, oxo or $C_{1-6}$-alkyl;

R$^{12}$ is H, $C_{1-6}$-alkyl or halo-$C_{1-6}$-alkyl;

x is independently 1, 2, 3 or 4;

Ar is a 5-10 membered mono- or bicyclic heteroaromatic ring system containing 1, 2, or 3 heteroatoms independently selected from the group consisting of N, O and S; or a 6-10 membered mono- or bicyclic aromatic ring system wherein the heteroaromatic and the aromatic ring system is unsubstituted or substituted by 1, 2 or 3 substituents independently selected from the group consisting of hydroxy, halogen, cyano, halo-$C_{1-6}$-alkyl, $C_{1-6}$-alkyl, $C_{3-6}$-cycloalkyl, O—$C_{1-6}$-alkyl, O-(halo-$C_{1-6}$-alkyl), COOH, CO$_2$NR$^{10}$R$^{11}$, NR$^{10}$R$^{11}$, a saturated 3-10 membered heterocycle containing 1 or 2 heteroatoms independently selected from the group consisting of N, O and S, a 5-10 membered mono- or bicyclic heteroaromatic ring system containing 1, 2 or 3 heteroatoms independently selected from the group consisting of N, O and S and a 6-10 membered mono- or bicyclic aromatic ring system wherein the heteroaromatic and aromatic ring system is unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl and COOH;

X, and Y are independently from each other selected from the group consisting of O, CH$_2$, C(CH$_3$)$_2$, NH, N($C_{1-6}$-alkyl), N(hydroxy-$C_{1-6}$-alkyl), S, SO$_2$, C=O and

wherein $C_{1-6}$-alkyl is unsubstituted or substituted by 1, 2 or 3 substituents independently selected from the group consisting of hydroxy, oxo, halogen and cyano; Z is CH$_2$, C(CH$_3$)$_2$ or CO;

whereby (1) combinations of X, Y and Z where O is directly connected to O, NH, N($C_{1-6}$-alkyl), N(hydroxy-$C_{1-6}$-alkyl), S, CO or SO$_2$, (2) combinations of X, Y and Z where NH, N($C_{1-6}$-alkyl), N(hydroxy-$C_{1-6}$-alkyl) is directly connected to S, NH, N($C_{1-6}$-alkyl), N(hydroxy-$C_{1-6}$-alkyl) and (3) combinations of X, Y and Z where S is directly connected to S, CO or SO$_2$ are excluded and with the proviso that (1) the compound wherein Ar is unsubstituted phenyl, X is O, Y is CH$_2$, Z is CH$_2$, R$^2$ is phenyl para-substituted with CH$_3$ and (L)$_a$-R$^1$ is CH$_2$Ph and (2) the compounds, where the carbon atom in ring Ar directly neighbouring the bridgehead atom marked with "*" is substituted with an aromatic, $C_{3-6}$-cycloalkyl or heterocyclic group are excluded.

In a preferred embodiment in combination with any of the above or below embodiments, the radical X represents NH or a CH$_2$ group. More preferably, X represents a CH$_2$ group.

In a further preferred embodiment in combination with any of the above or below embodiments, the radical Y represents an oxygen atom, NH, or N($C_{1-6}$-alkyl), wherein the alkyl group is unsubstituted or substituted by 1,2 or 3 substituents independently selected from the group consisting of hydroxy, oxo, halogen and cyano. More preferably, Y represents an oxygen atom or a CH$_2$ group.

In a further preferred embodiment in combination with any of the above or below embodiments, the radical Z represents a CH$_2$ group.

The following combinations of X, Y and Z are preferred within the invention in combination with any of the above or below embodiments:

| X | Y | Z |
|---|---|---|
| NR$^{13}$ | CO | CH$_2$, C(CH$_3$)$_2$ |
| NR$^{13}$ | CH$_2$ | CH$_2$, C(CH$_3$)$_2$ |

-continued

| X | Y | Z |
|---|---|---|
| NR$^{13}$ | SO$_2$ | CH$_2$, C(CH$_3$)$_2$ |
| S | CH$_2$, C(CH$_3$)$_2$ | CH$_2$, C(CH$_3$)$_2$ |
| CH$_2$, C(CH$_3$)$_2$ | S | CH$_2$, C(CH$_3$)$_2$ |
| SO$_2$ | CH$_2$, C(CH$_3$)$_2$ | CH$_2$, C(CH$_3$)$_2$ |
| SO$_2$ | NR$^7$ | CH$_2$, C(CH$_3$)$_2$ |
| SO$_2$ | NR$^7$ | CO |
| CH$_2$, C(CH$_3$)$_2$ | CO | CH$_2$, C(CH$_3$)$_2$ |
| CH$_2$, C(CH$_3$)$_2$ | CH$_2$, C(CH$_3$)$_2$ | CO |
| CH$_2$, C(CH$_3$)$_2$ | SO$_2$ | CH$_2$, C(CH$_3$)$_2$ |
| CH$_2$, C(CH$_3$)$_2$ | CH$_2$, C(CH$_3$)$_2$ | CH$_2$, C(CH$_3$)$_2$ |
| CH$_2$, C(CH$_3$)$_2$ | NR$^7$ | CH$_2$, C(CH$_3$)$_2$ |
| CH$_2$, C(CH$_3$)$_2$ | NR$^7$ | CO |
| CO | CH$_2$, C(CH$_3$)$_2$ | CH$_2$, C(CH$_3$)$_2$ |
| CO | NR$^7$ | CH$_2$, C(CH$_3$)$_2$ | with R$^{13}$ being selected from H, C$_{1-6}$-alkyl, halo-C$_{1-6}$-alkyl and hydroxy-C$_{1-6}$-alkyl.

In a further preferred embodiment in combination with any of the above or below embodiments, the radical L is preferably —CH$_2$—, —CH$_2$CH$_2$—, —CH$_2$CH$_2$CH$_2$—, —CH$_2$CH$_2$CH$_2$CH$_2$—, —CF$_2$—, —CH$_2$CF$_2$—, —CF$_2$CH$_2$—, —CH$_2$CH$_2$CF$_2$—, —CH$_2$—NH—, —CH$_2$—N(CH$_3$)—, —CH$_2$—O—, —CH$_2$CH$_2$—O—, or —CH$_2$—O—CH$_2$—, more preferably —CH$_2$—, —CF$_2$—, —CH$_2$—NH—, —CH$_2$—O—CH$_2$— or —CH$_2$—O—. In a particular preferred embodiment in combination with any of the above or below embodiments, the radical L is —CH$_2$—, —CH$_2$—O— or —CH$_2$OCH$_2$—.

In a further preferred embodiment in combination with any of the above or below embodiments, Ar is phenyl, pyridyl, pyrazyl, pyridazyl and pyrimidyl, wherein Ar is unsubstituted or substituted by 1, 2, or 3 substituents independently selected from the group consisting of hydroxy, halogen, cyano, C$_{3-6}$-cycloalkyl, O—C$_{1-6}$-alkyl, and halo-(C$_{1-6}$-alkyl). More preferably, Ar is phenyl, pyridyl, or pyrimidyl, wherein Ar is unsubstituted or substituted by 1, 2, or 3 substituents independently selected from the group consisting of hydroxy, halogen, C$_{1-4}$-alkyl, O—C$_{1-4}$-alkyl, and halo-(C$_{1-4}$-alkyl);

In a further preferred embodiment in combination with any of the above or below embodiments, the radical R$^1$ is C$_{1-12}$-alkyl; C$_{3-10}$-cycloalkyl, a 5-6 membered monocyclic heteroaromatic ring containing 1, 2, 3 or 4 heteroatoms independently selected from the group consisting of N, O and S; or a 6-membered monocyclic aromatic ring wherein the alkyl group, the cycloalkyl group, the heteroaromatic and the aromatic rings are independently from each other unsubstituted or substituted by 1, 2 or 3 substituents independently selected from the group consisting of hydroxy, oxo, halogen, cyano, halo-C$_{1-12}$-alkyl, C$_{1-6}$-alkyl, C$_{3-6}$-cycloalkyl, O—C$_{1-6}$-alkyl, COOH, a 5-10 membered mono- or bicyclic heteroaromatic ring system containing 1, 2 or 3 heteroatoms independently selected from the group consisting of N, O and S, and a 6-10 membered mono- or bicyclic aromatic ring system wherein the heteroaromatic and the aromatic ring systems are independently from each other unsubstituted or substituted by 1, 2 or 3 substituents independently selected from the group consisting of hydroxy, oxo, halogen, cyano, halo-C$_{1-12}$-alkyl, C$_{3-6}$-cycloalkyl, O—C$_{1-6}$-alkyl and COOH.

More preferably, the alkyl group, the cycloalkyl group, the heteroaromatic and the aromatic rings are independently from each other unsubstituted or substituted by 1, 2 or 3 substituents independently selected from the group consisting of hydroxy, oxo, halogen, halo-C$_{1-12}$-alkyl, O—C$_{1-6}$-alkyl and O-(halo-C$_{1-6}$-alkyl).

In a more preferred embodiment in combination with any of the above or below embodiments, the radical R$^1$ is C$_{1-12}$-alkyl; C$_{3-10}$-cycloalkyl or a 6-membered aromatic ring system wherein the alkyl and the cycloalkyl groups are unsubstituted or substituted by 1, 2 or 3 substituents independently selected from the group consisting of halogen, cyano, halo-C$_{1-6}$-alkyl, O—C$_{1-6}$-alkyl and O-(halo-C$_{1-6}$-alkyl);

and wherein the 6-membered aromatic ring system is unsubstituted or substituted by 1, 2 or 3 substituents independently selected from the group consisting of halogen, cyano, C$_{1-6}$-alkyl, halo-C$_{1-6}$-alkyl, O—C$_{1-6}$-alkyl and O-(halo-C$_{1-6}$-alkyl).

In a preferred embodiment in combination with any of the above or below embodiments, L-R$^1$ represents

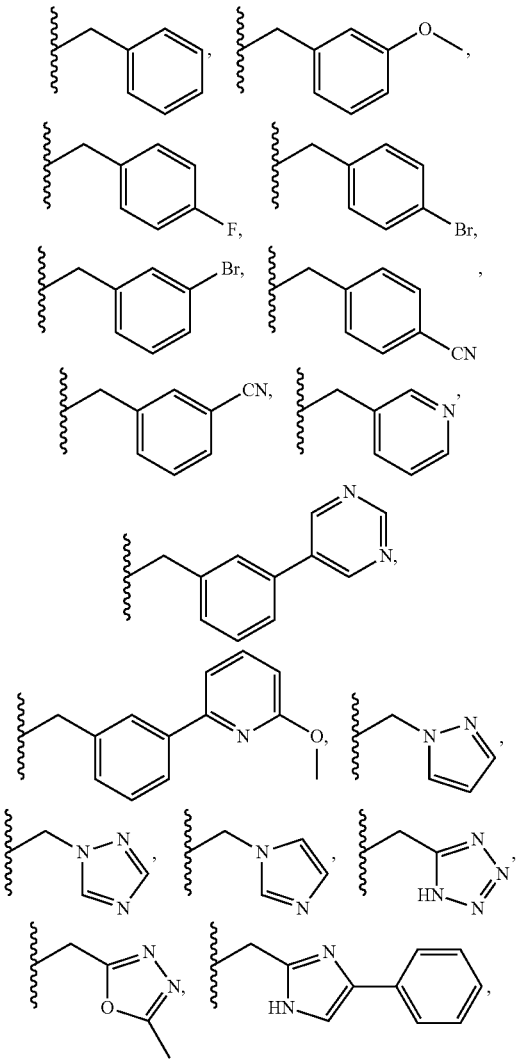

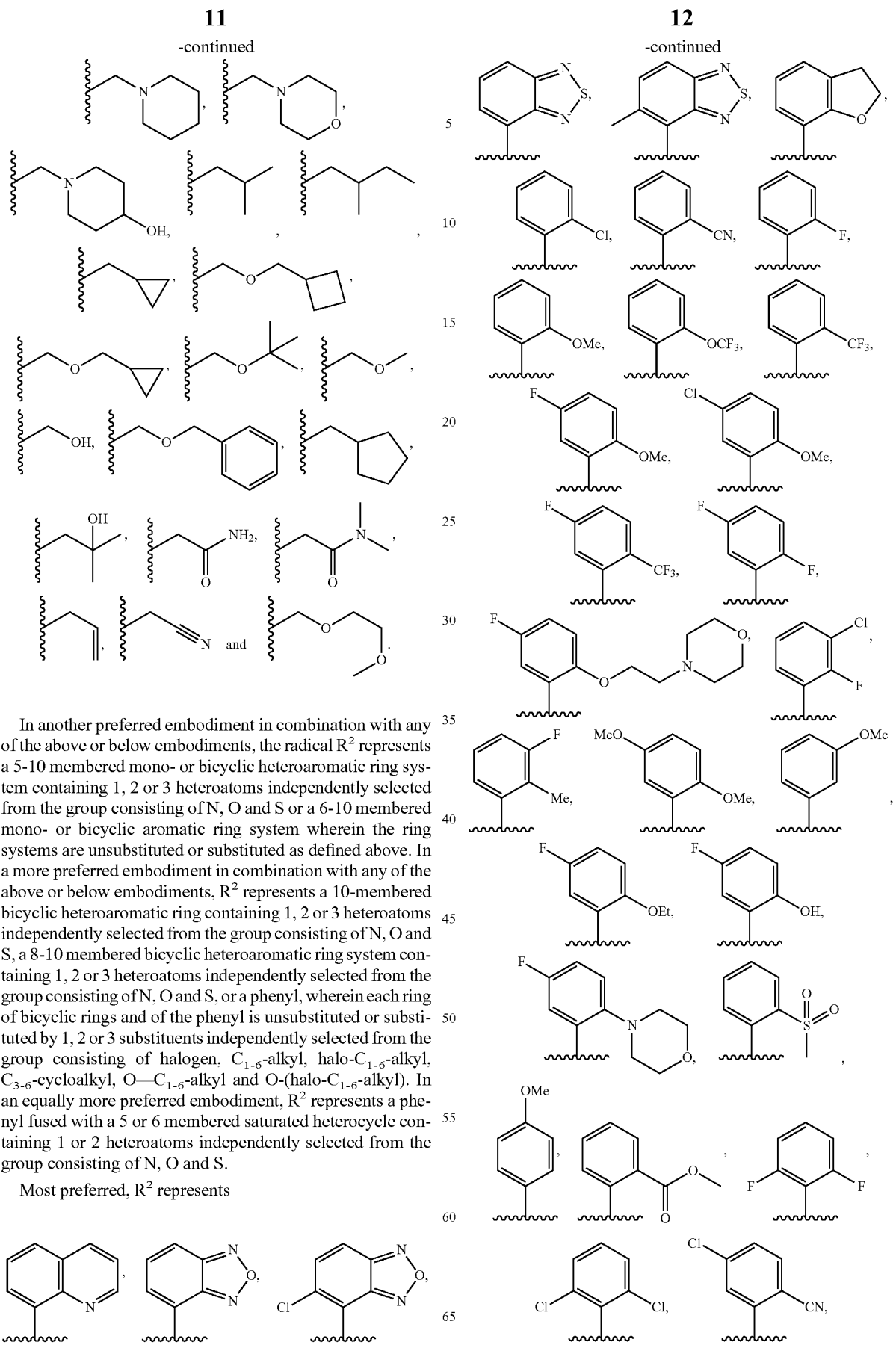

In another preferred embodiment in combination with any of the above or below embodiments, the radical $R^2$ represents a 5-10 membered mono- or bicyclic heteroaromatic ring system containing 1, 2 or 3 heteroatoms independently selected from the group consisting of N, O and S or a 6-10 membered mono- or bicyclic aromatic ring system wherein the ring systems are unsubstituted or substituted as defined above. In a more preferred embodiment in combination with any of the above or below embodiments, $R^2$ represents a 10-membered bicyclic heteroaromatic ring containing 1, 2 or 3 heteroatoms independently selected from the group consisting of N, O and S, a 8-10 membered bicyclic heteroaromatic ring system containing 1, 2 or 3 heteroatoms independently selected from the group consisting of N, O and S, or a phenyl, wherein each ring of bicyclic rings and of the phenyl is unsubstituted or substituted by 1, 2 or 3 substituents independently selected from the group consisting of halogen, $C_{1-6}$-alkyl, halo-$C_{1-6}$-alkyl, $C_{3-6}$-cycloalkyl, O—$C_{1-6}$-alkyl and O-(halo-$C_{1-6}$-alkyl). In an equally more preferred embodiment, $R^2$ represents a phenyl fused with a 5 or 6 membered saturated heterocycle containing 1 or 2 heteroatoms independently selected from the group consisting of N, O and S.

Most preferred, $R^2$ represents

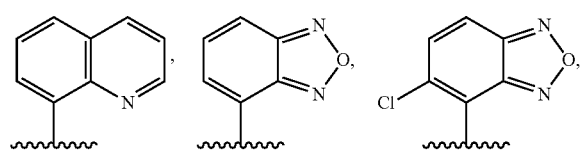

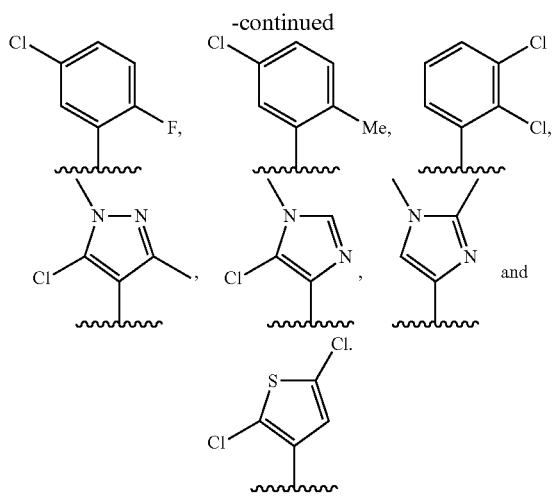

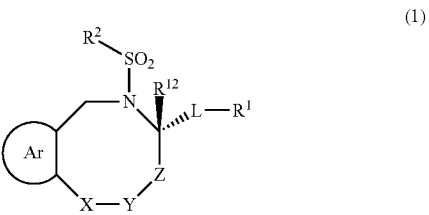

(1)

In the context of the present invention $C_{1-12}$-alkyl means a saturated alkyl chain having 1 to 12 carbon atoms which may be straight chained or branched. Examples thereof include methyl, ethyl, propyl, isopropyl, n-butyl, isobutyl, tert-butyl, n-pentyl, isopentyl, neopentyl, hexyl, heptyl, octyl, nonyl, decyl, undecyl and dodecyl.

The term "halo-$C_{1-12}$-alkyl" means that one or more hydrogen atoms in the alkyl chain are replaced by a halogen. A preferred example thereof is $CF_3$.

$C_{1-12}$-alkenyl means an alkyl chain having 1 to 12 carbon atoms which may be straight chained or branched, containing at least one carbon to carbon double bond. Examples thereof include ethenyl, propenyl, dodecenyl, 2-methylenehexyl and (2E,4E)-hexa-2,4-dienyl.

$C_{1-12}$-alkynyl means an alkyl chain having 1 to 12 carbon atoms which may be straight chained or branched, containing at least one carbon to carbon triple bond. Examples thereof include ethynyl, propynyl and dodecynyl.

A $C_{3-10}$-cycloalkyl group means a saturated mono-, bi- or multicyclic ring system comprising 3 to 10 carbon atoms. Examples include cyclopropyl, cyclobutyl, cyclopentyl, cyclohexyl, bicyclo[2.2.2]octyl, bicyclo[2.2.1]heptyl, pentacyclo[4.2.0.0$^{2.5}$.0$^{3.8}$.0$^{4.7}$]octyl and adamantyl.

A saturated heterocycle having at least 3 up to 10 ring members and containing up to 3 heteroatoms means a 3 to 10 membered carbon mono-, bi- or multicyclic ring wherein 1, 2 or 3 carbon atoms are replaced by 1, 2 or 3 heteroatoms, respectively, wherein the heteroatoms are independently selected from N, O and S. Examples thereof include epoxide, oxiran, pyrrolidine, tetrahydrofuran, piperidine, piperazine, tetrahydropyran, dioxane, morpholine and 4-quinuclidinyl.

A 5-10 membered mono- or bicyclic heteroaromatic ring system containing up to 4 heteroatoms means a monocyclic heteroaromatic ring such as pyrrole, imidazole, furan, thiophene, pyridine, pyrimidine, pyrazine, pyrazole, oxazole, isoxazole, triazole, oxadiazole, and thiadiazole. It further means a bicyclic ring system wherein the heteroatom(s) may be present in one or both rings including the bridgehead atoms. Examples thereof include quinoline, isoquinoline, quinoxaline, benzimidazole, benzisoxazole, benzodioxane, benzofuran, benzoxazole, indole, indolizine and pyrazolo[1,5-a]pyrimidine.

A 6-10 membered mono- or bicyclic aromatic ring system means an aromatic carbon cycle such as phenyl or naphthalene.

Halogen is selected from fluorine, chlorine, bromine and iodine.

The compounds of the present invention are optical isomers. The stereoisomer of Formula (1) with the following structure is preferred:

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

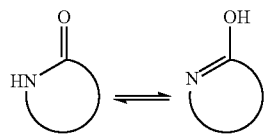

Moreover, the circle depicting the group Ar in Formula (1) is to be interpreted that the bridgehead atoms connecting Ar to the 8 membered ring system can be independently from each other a carbon atom or a nitrogen atom and, furthermore, is to be interpreted that both bridgehead atoms are vicinal to each other.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds used in the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous), ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing RORγ-mediated conditions for which compounds of Formula (1) are indicated, generally satisfactory results are obtained when the compounds are administered at a daily dosage of from about 0.1 milligram to about 100 milligram per kilogram of mammal body weight, preferably given as a single daily dose or in divided doses two to six times a day, or in sustained release form. For most large mammals, the total daily dosage is from about 1.0 milligram to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The present invention describes modulators, in the following also referred to as ligands, which bind to the RORγ receptor. Surprisingly, it has been found that compounds of Formula (1) act as modulators of the RORγ receptor.

The RORγ receptor is considered to be involved in thymocyte development, thus the modulators described herein may be useful in the treatment of inflammatory skin diseases such as atopic eczema and psoriasis. It is further suggested that down-modulation of RORγ transcriptional activity with a ligand could result in a shift of the immune response towards a Th2 type response which could be beneficial in the treatment of certain allergic inflammatory conditions such as rheumatoid arthritis, systemic lupus erythomatosis, inflammatory bowel disease (Crohn's Disease), and multiple sclerosis (Tesmer et. al., *Immunol. Rev.* 2008, 223:97).

The compounds of Formula (1) show antagonistic activity, with respect to the dose dependent modulation of the constitutive interaction of the RORγ ligand binding domain with peptides derived from the co-activators such as SRC-1, TRAP 220 or TIF-2.

It has been surprisingly found that the interaction between RORγ ligand binding domain and the peptides can be determined by a homogenous FRET based ligand-sensing assays. Even more surprising was the identification of compounds of Formula (1) as ligands for RORγ.

The identification of high affinity ligands for RORγ with agonistic and antagonistic properties is the basis to enable experts knowledgeable in the field to establish assays for the identification of novel agonistic and antagonistic RORγ ligands from libraries of small molecules. The identification of ligands which bind to and modulate the activity of RORγ1 and RORγ2 is the first mandatory step to develop new small molecule based medicines with a potential to be developed for the treatment of diseases which are directly or indirectly controlled by the activity of RORγ1 or RORγ2. Such diseases include but are not restricted to inflammatory diseases, asthma, rheumatoid arthritis, autoimmune diseases or diseases with an autoimmune component such as systemic lupus erythomatosis, inflammatory bowel disease (Crohn's disease), ulcerative colitis, inflammatory skin diseases such as atopic eczema or psoriasis, multiple sclerosis or similar diseases.

The compounds of the present invention can be prepared by a combination of methods known in the art including the procedures described in Schemes I to IV below.

Scheme I depicts the alkylation of an amino alcohol of formula (A-II) with a (hetero)aromatic methylester ortho-substituted with a bromomethyl substituent (A-I) in the presence of an appropriate base in a suitable solvent. The resulting ether intermediate (A-III) can be successively amine deprotected and saponified to yield amino acids of formula (A-IV). The eight-membered lactam ring can be formed by the use of suitable amide coupling reagents and after reduction to the corresponding cyclic amines (A-VI) by suitable hydride donor reagents final compounds (A-VII) can be obtained by reaction with sulfonylchlorides in the presence of appropriate bases in appropriate solvents.

Alternatively, as shown in Scheme II, intermediates of formula (A-III) can be reduced to the corresponding alcohols (B-I) by use of appropriate hydride donor reagents. B-I can be reacted with phosphorous tribromide to afford bromomethyl intermediate (B-II). After deprotection of the amino group under acidic conditions (B-III) can be transformed into cyclic intermediate (A-VI) by treatment with an appropriate base. Reaction with sulfonyl chlorides in the presence of a base affords the final compounds (A-VII).

Scheme II

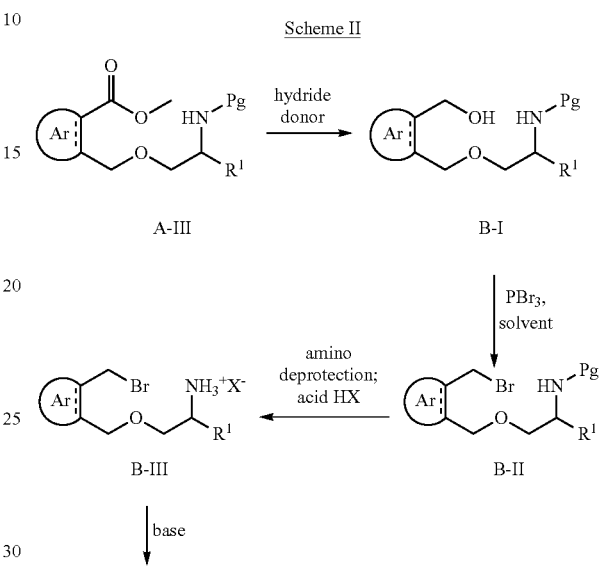

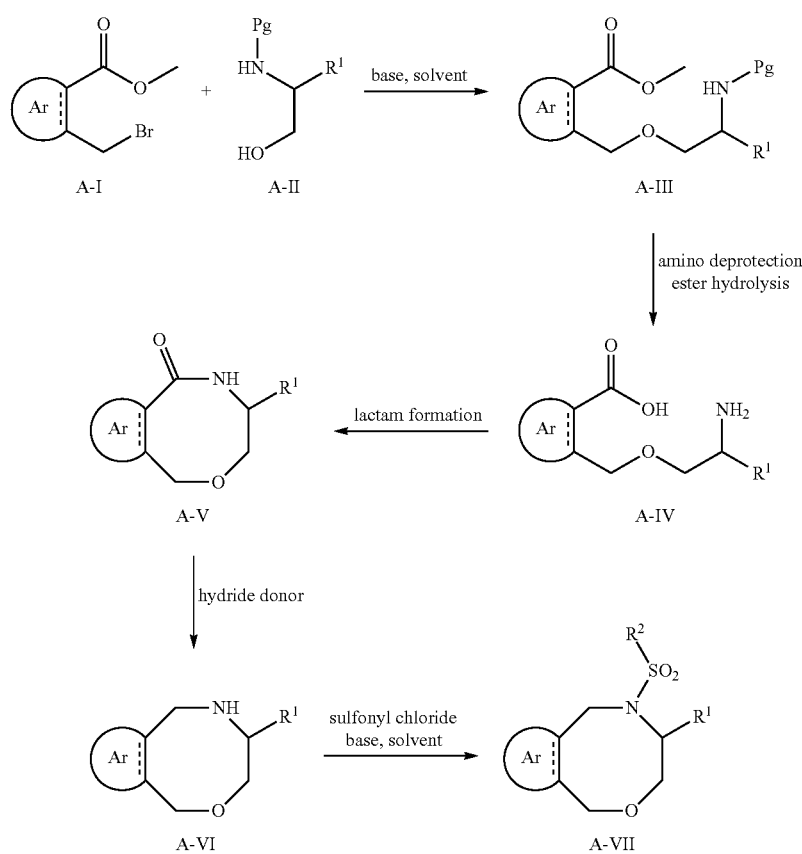

-continued

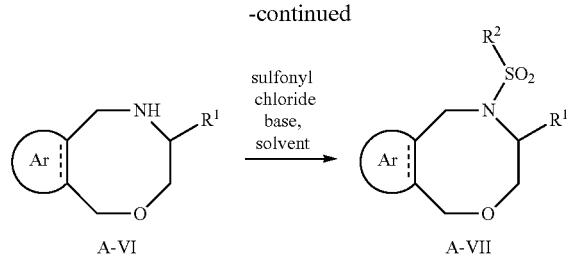

Another way of preparing compounds of the present invention is depicted in Scheme III. Protected aminoethylsulfonamide (C-I) is alkylated with compounds of formula (A-I) in the presence of a base like NaH in solvents like DMF to afford intermediates (C-II). Ester hydrolysis and amino-deprotection afford compounds (C-III) which can be cyclized to eight membered lactams (C-IV) by the use of appropriate amide coupling reagents. Alkylation of the lactam nitrogen and reduction of the lactam to an amine yields final compounds (C-VI).

Scheme III

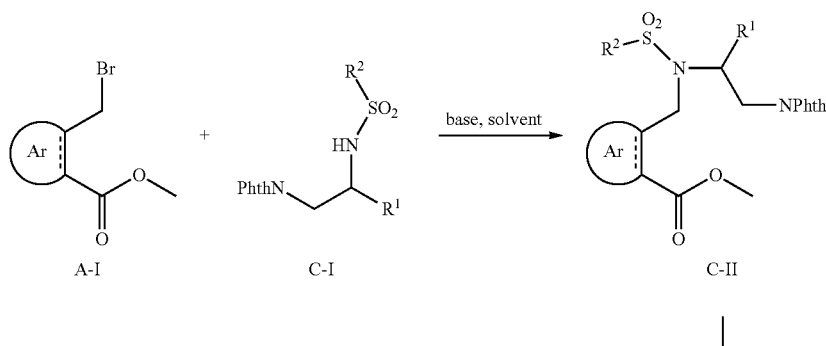

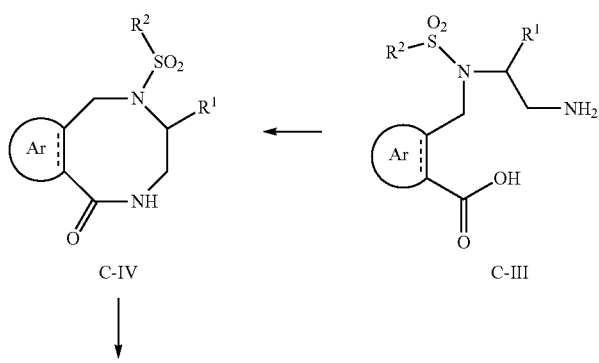

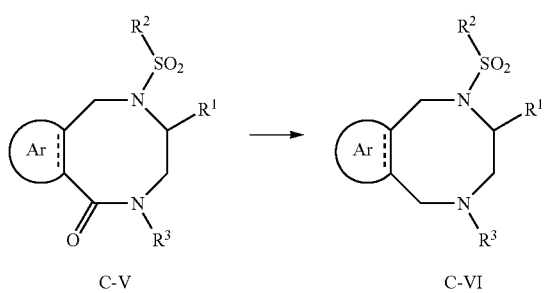

Another way of preparing compounds of the present invention is depicted in Scheme IV. Protected aminoester (D-I) is reduced to the corresponding aldehyde followed by Wittig reaction to afford intermediates (D-II). Amino deprotection and subsequent sulfonylation afford compounds (D-III). N-alkylation with bromo ester and base affords intermediates (D-IV). Reduction followed by ester hydrolysis yields amino acid intermediates (D-V) which can be cyclized to eight membered lactams (C-VI) by the use of appropriate amide coupling reagents. Thionation of the lactam carbonyl affords intermediates (D-VII) which can be converted to heterocylic compounds (D-VIII).

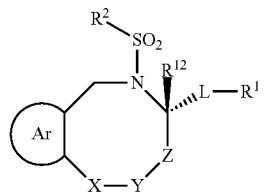

(1)

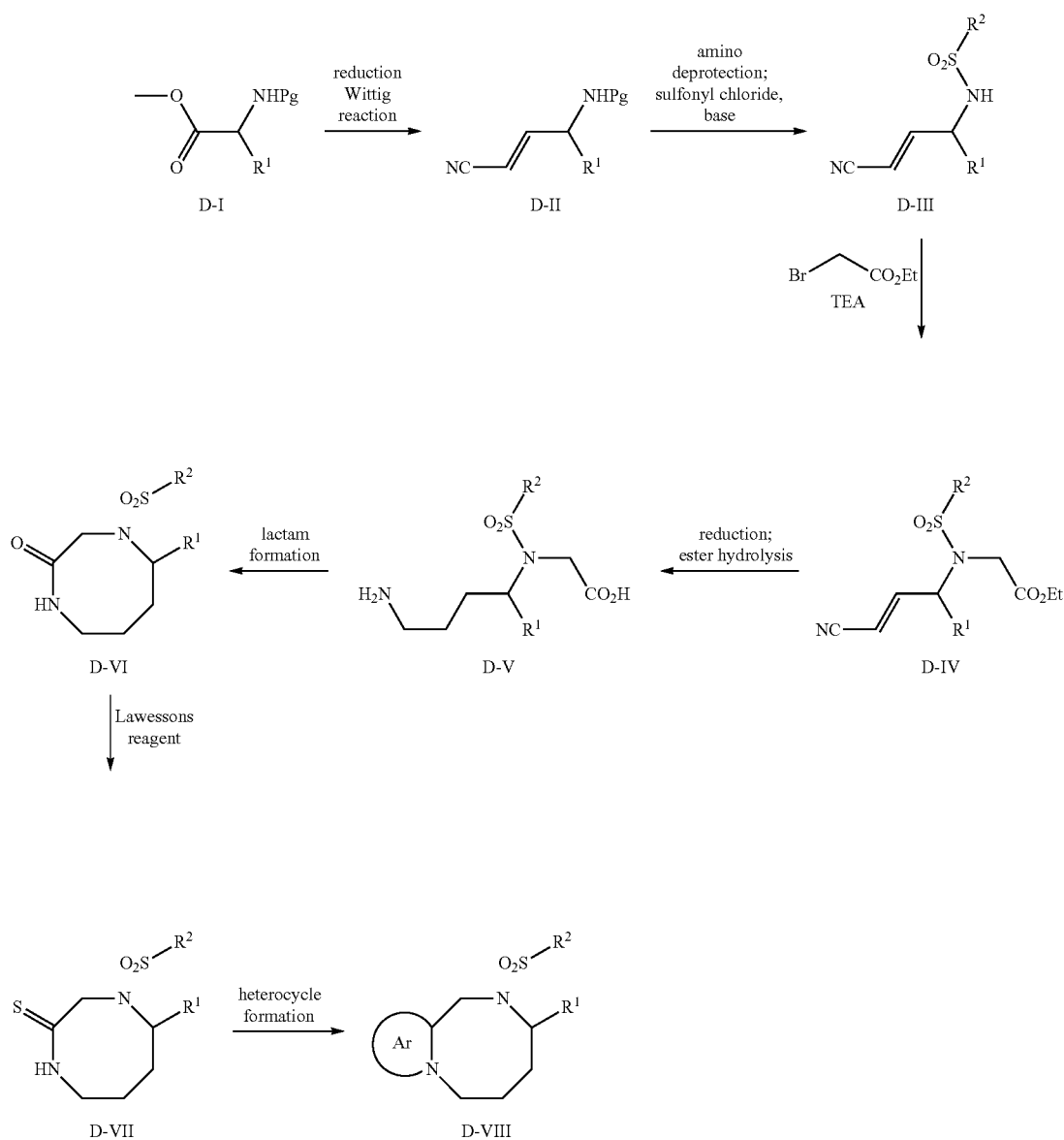

The compounds described in the present invention are racemates and can be prepared as single enantiomers when homochiral aminoalcohols (A-II) or diamines (C-I) are used. The stereoisomer of Formula (1) with the following structure usually shows a higher biological activity:

In the following examples the abbreviations listed below are used.

ACN acetonitrile
Boc tert-butyloxycarbonyl
BOP-Cl (bis(2-oxo-3-oxazolidin)yl)phosphonic chloride CC column chromatography
DCM dichloromethane
DIBAL-H Diisobutylaluminium hydride
DIPEA diisopropyl-ethylamine
DMAP 4-(dimethylamino)-pyridine
DMF dimethylformamide
DPPA diphenylphosphoryl azide
EA ethyl acetate
Et ethyl
HATU 2-(1H-7-azabenzotriazol-1-yl)-1,1,3,3-tetramethyl uronium hexafluorophosphate
LAH lithium aluminium hydride
mCPBA meta-chloroperoxybenzoic acid
Ms methanesulfonyl
NBS N-bromo-succinimide
Phth phthalate
Pg protecting group
PE petroleum ether
rt room temperature
SM starting material
TEA triethylamine
TFA trifluoro acetic acid
THF tetrahydrofuran
TLC thin layer chromatography

EXAMPLES

Preparative Example 1

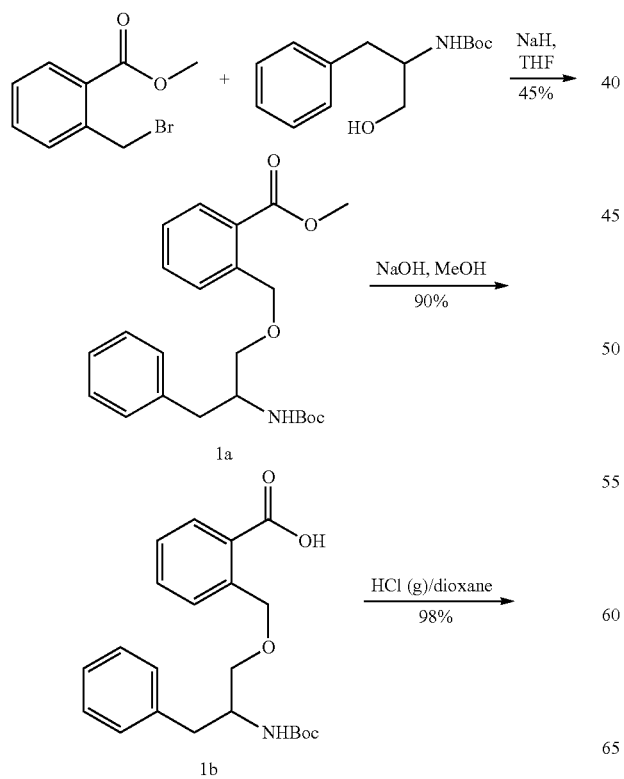

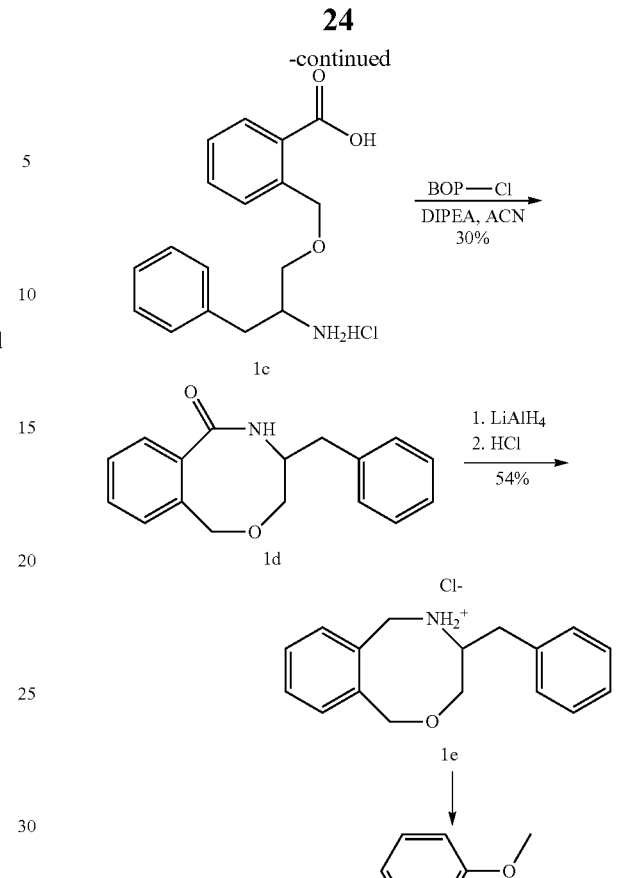

Step 1: Methyl 2-((2-(tert-butoxycarbonylamino)-3-phenylpropoxy)methyl)benzoate (1a)

To a solution of methyl 2-(bromomethyl)benzoate (25.1 g, 100 mmol) in dry THF (600 mL) was added NaH (60 percent, 8.8 g, 220 mmol) in small portions at 5° C. and stirred for 10 min. Then tert-butyl 1-hydroxy-3-phenylpropan-2-yl carbamate (22.9 g, 100 mmol) in THF (100 mL) was added dropwise, and the reaction mixture was allowed to stir at rt overnight. The reaction was quenched with water (400 mL) and extracted with EA (2×400 mL). The combined organic extracts were dried over anhydrous $Na_2SO_4$ and concentrated under reduced pressure. The residue was purified by CC eluting with PE:EA=7:1 to give compound 1a as a white solid (18.0 g, 45% yield). $^1$H NMR (400 MHz, $CDCl_3$): δ 7.93 (d, J=8.0 Hz, 1H), 7.62 (d, J=8.0 Hz, 1H), 7.52 (t, J=8.0 Hz, 1H), 7.33 (t, J=7.2 Hz, 1H), 7.25-7.16 (m, 5H), 4.95-4.93 (m, 1H), 4.90-4.79 (m, 2H), 3.87 (s, 3H), 3.49-3.43 (m, 2H), 2.91-2.84 (m, 2H), 1.40 (s, 9H).

Step 2: 2-((2-(tert-Butoxycarbonylamino)-3-phenyl-propoxy)methyl)benzoic acid (1b)

The suspension of compound 1a (39.9 g, 100 mmol) in 3.5N aqueous NaOH (130 mL) and MeOH (350 mL) was heated to 50° C. for 3 hr. Then the mixture was cooled to rt and acidified to pH=3 with 3.5N aqueous HCl, extracted with EA (2×300 mL). The organic extracts were combined and dried over anhydrous Na$_2$SO$_4$, concentrated under reduced pressure to get compound 1b as a white solid (34.7 g, 90% yield). $^1$H NMR (400 MHz, CDCl$_3$): δ 8.08-8.06 (m, 1H), 7.73-7.53 (m, 2H), 7.42-7.40 (m, 1H), 7.30-7.19 (m, 5H), 4.95-4.84 (m, 2H), 4.05-4.02 (m, 1H), 3.55-3.48 (m, 2H), 2.93-2.91 (m, 2H), 1.45 (s, 9H).

Step 3:
2-((2-Amino-3-phenylpropoxy)methyl)benzoic acid hydrochloride (1c)

Compound 1b (34.7 g, 90 mmol) was treated with HCl (g) in dioxane (700 mL) at rt overnight. Concentrated in vacuo gave the hydrochloride salt of compound 1c which was used for next step without any further purification (28.3 g, 98% yield). MS (ESI+): 286 [M+1]$^+$.

Step 4: 4-Benzyl-4,5-dihydro-1H-benzo[f][1,4]oxazocin-6(3H)-one (1d)

To a solution of compound 1c (28 g, 87 mmol) obtained above in CH$_3$CN (1.5 L) was added DIPEA (68 g, 520 mmol) at 0° C., followed by BOP-Cl (70 g, 275 mmol). The resulting mixture was stirred at 0° C. for 30 min and then warmed to rt overnight. The solid was removed by filtration and the filtrate was concentrated in vacuo. The residue was dissolved in EA, washed with 2N HCl and dried over anhydrous Na$_2$SO$_4$. Concentration in vacuo and purification by CC eluting with PE:EA=1:2 gave compound 1d as a yellow oil (7.0 g, 30% yield). $^1$H NMR (400 MHz, CDCl$_3$): δ 7.50 (dd, J=7.6, 1.6 Hz, 1H), 7.41-7.34 (m, 2H), 7.28-7.19 (m, 4H), 7.05 (d, J=7.2 Hz, 2H), 5.83 (m, 1H), 4.82 (d, J=14.0 Hz, 1H), 4.61 (d, J=13.6 Hz, 1H), 3.82-3.78 (m, 1H), 3.78-3.67 (m, 1H), 3.58-3.55 (m, 1H), 2.75-2.71 (m, 2H). MS (ESI+): 268 [M+1]$^+$.

Step 5: 4-Benzyl-3,4,5,6-tetrahydro-1H-benzo[f][1,4]oxazocine hydrochloride (1e)

To a solution of compound 1d (7.0 g, 26.2 mmol) in THF (150 mL) was added slowly LiAlH$_4$ (6.0 g, 157 mmol) at 0° C. The resulting mixture was heated to reflux for 2 hr. Then the reaction was cooled to 5° C., quenched with water (6 mL) and aqueous NaOH (15% w/w; 6 mL) under vigorous stirring. The precipitate was removed by filtration and the filtrate was concentrated in vacuo. The residue was dissolved in 2N HCl (100 mL) and extracted with EA (2×80 mL). The aqueous phase was basified with 2N aq. NaOH and extracted with EA (2×100 mL). The combined organic layers were dried over anhydrous Na$_2$SO$_4$ and concentrated in vacuo to give compound 1e as pale yellow oil (3.7 g, 56% yield). $^1$H NMR (400 MHz, CDCl$_3$): δ 7.27-7.16 (m, 5H), 7.12-7.06 (m, 4H), 4.96-4.82 (m, 2H), 4.34 (d, J=14.4 Hz, 1H), 3.96 (d, J=14.4 Hz, 1H), 3.82 (dd, J=12.0, 2.0 Hz, 1H), 3.60 (dd, J=12.0, 8.0 Hz, 1H), 3.20-3.14 (m, 1H), 2.63 (dd, J=14.0, 5.2 Hz, 1H), 2.52 (dd, J=14.0, 8.4 Hz, 1H).
Preparation of Hydrochloride Salt of Compound (1e)

The solution of compound 1e (5.4 g, 21 mmol) in EA (10 mL) was treated with HCl (1.0N in EA, 45 mL) at rt for 10 min and then concentrated in vacuo to one fifth of its original volume. Hexane (50 mL) was added to the residue under stirring. The solid formed was collected by filtration and washed with hexane, dried in vacuo to afford the hydrochloride salt of compound 1e as a light pink solid (5.95 g, 96% yield). $^1$H NMR (400 MHz, CDCl$_3$): δ 10.36 (brs, 1H), 10.21 (brs, 1H), 7.62 (d, J=6.8 Hz, 1H), 7.42-7.11 (m, 8H), 5.18 (d, J=12.8 Hz, 1H), 5.10 (d, J=16.0 Hz, 1H), 4.63 (d, J=16.4 Hz, 1H), 4.50 (d, J=12.4 Hz, 1H), 4.25 (dd, J=12.8, 9.2 Hz, 1H), 3.73 (dd, J=13.2, 2.8 Hz, 1H), 3.52-3.49 (m, 2H), 3.09 (t, J=12.0 Hz, 1H). MS (ESI+): 254 [M+H]$^+$.

Step 6: 4-Benzyl-5-(2-methoxyphenylsulfonyl)-3,4,5,6-tetrahydro-1H-benzo[f][1,4]-oxazocine (1)

To a solution of compound 1e—HCl salt (50 mg, 0.17 mmol) in DCM (3 mL) and Et$_3$N (34 mg, 0.34 mmol) was added 2-methoxybenzene-1-sulfonyl chloride (41 mg, 0.2 mmol). The mixture was stirred at rt overnight. The solvent was removed under vacuum and the resulting crude product was purified by prep-HPLC to afford the target compound 1 (46 mg, 64% yield). $^1$H NMR (400 MHz, CDCl$_3$): δ 7.89 (d, J=6.0 Hz, 1H), 7.46 (m, 1H), 7.25-7.10 (m, 5H), 7.06-6.99 (m, 4H), 6.82 (d, J=8.4 Hz, 1H), 5.10 (d, J=14.8 Hz, 1H), 4.93 (d, J=14.7, 1H), 4.82 (d, J=14.7, 1H), 3.99 (d, J=10.8 Hz, 1H), 3.74 (s, 3H), 3.75-3.73 (m, 1H), 3.51 (d, J=12.8 Hz, 1H), 3.15 (t, J=12.4 Hz, 1H), 2.49-2.45 (m, 1H). MS (ESI+): 424 [M+H]$^+$.

Preparative Examples 1/1 to 1/44

Following similar procedures as described in the Preparative Example 1 the following compounds were prepared.

| # | Structure | MW (g/mol) | Measured m/z of [M + H]$^+$ |
|---|---|---|---|
| 1/1 | 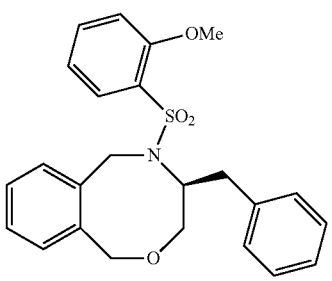 with subsequent separation by chiral chromatography | 423.5 | 424 |

-continued

| # | Structure | MW (g/mol) | Measured m/z of [M + H]+ |
|---|---|---|---|
| 1/2 | (structure with OMe, SO₂, benzoxocine, benzyl) from homochiral SM | 423.5 | 424 |
| 1/3 | (structure with OCF₃, sulfonyl, benzoxocine, benzyl) | 477.5 | 478 |
| 1/4 | (structure with CN, sulfonyl, benzoxocine, benzyl) | 418.5 | 441 of [M + Na]+ |
| 1/5 | (structure with OMe, F, sulfonyl, benzoxocine, benzyl) | 441.5 | 442 |
| 1/6 | (structure with OMe, Cl, sulfonyl, benzoxocine, benzyl) | 458.0 | 458; 460 |

| # | Structure | MW (g/mol) | Measured m/z of [M + H]+ |
|---|---|---|---|
| 1/7 | 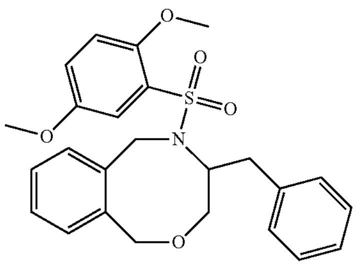 [SMILES: COc1ccc(OC)c(S(=O)(=O)N2Cc3ccccc3COCC2Cc2ccccc2)c1] | 453.6 | 454 |
| 1/8 | 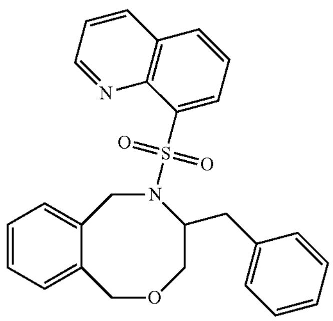 [SMILES: O=S(=O)(c1cccc2cccnc12)N1Cc2ccccc2COCC1Cc1ccccc1] | 444.5 | 445 |
| 1/9 | 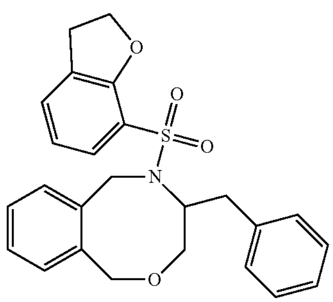 [SMILES: O=S(=O)(c1cccc2c1OCC2)N1Cc2ccccc2COCC1Cc1ccccc1] | 435.5 | 436 |
| 1/10 | 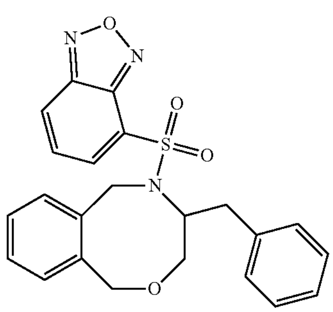 [SMILES: O=S(=O)(c1cccc2nonc12)N1Cc2ccccc2COCC1Cc1ccccc1] | 435.5 | 436 |
| 1/11 | 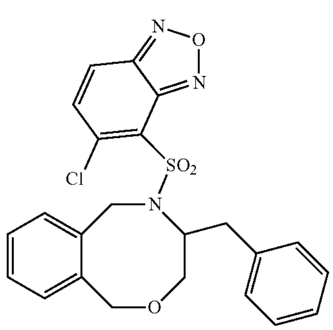 [SMILES: O=S(=O)(c1c(Cl)ccc2nonc12)N1Cc2ccccc2COCC1Cc1ccccc1] | 469.9 | 492; 494 of [M + Na]+ |

-continued

| # | Structure | MW (g/mol) | Measured m/z of [M + H]+ |
|---|---|---|---|
| 1/12 | 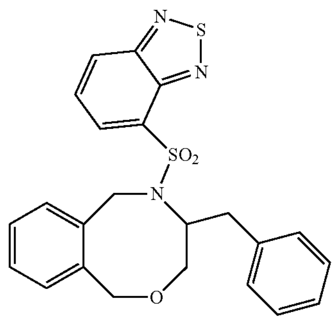 [SMILES: O=S(=O)(c1cccc2nsnc12)N1Cc2ccccc2COCC1Cc1ccccc1] | 451.6 | 452 |
| 1/13 | 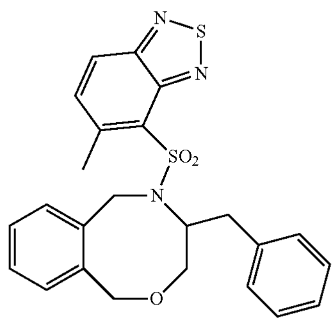 [SMILES: Cc1ccc2nsnc2c1S(=O)(=O)N1Cc2ccccc2COCC1Cc1ccccc1] | 465.6 | 466 |
| 1/14 | 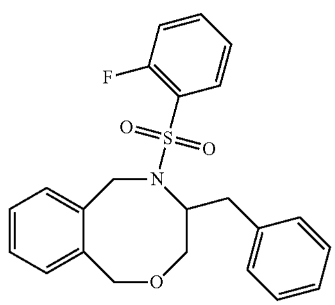 [SMILES: O=S(=O)(c1ccccc1F)N1Cc2ccccc2COCC1Cc1ccccc1] | 411.5 | 412 |
| 1/15 | 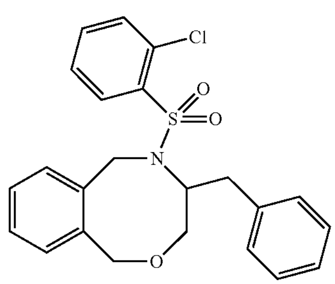 [SMILES: O=S(=O)(c1ccccc1Cl)N1Cc2ccccc2COCC1Cc1ccccc1] | 427.9 | 428; 430 |
| 1/16 | 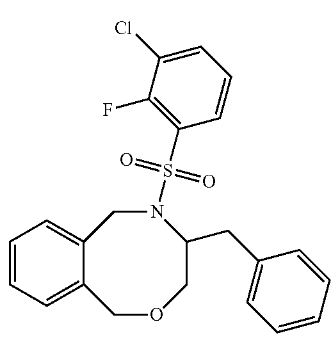 [SMILES: O=S(=O)(c1cccc(Cl)c1F)N1Cc2ccccc2COCC1Cc1ccccc1] | 445.9 | 468; 470 of [M + Na]+ |

-continued
| # | Structure | MW (g/mol) | Measured m/z of [M + H]+ |
|---|---|---|---|
| 1/17 | 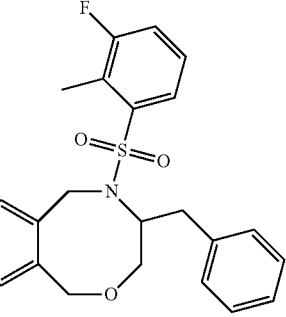 | 425.5 | 426 |
| 1/18 | 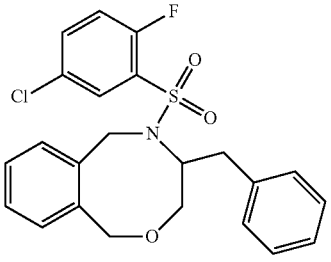 [SMILES: O=S(=O)(c1cc(Cl)ccc1F)N1Cc2ccccc2COCC1Cc1ccccc1] | 445.9 | 468; 470 of [M + Na]+ |
| 1/19 | 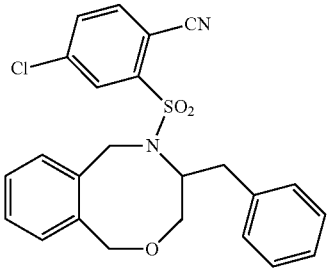 [SMILES: N#Cc1ccc(Cl)cc1S(=O)(=O)N1Cc2ccccc2COCC1Cc1ccccc1] | 453.0 | 475; 477 of [M + Na]+ |
| 1/20 | 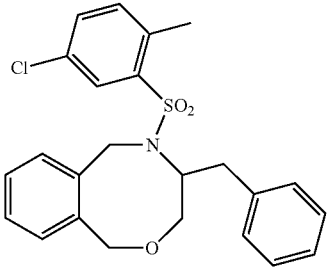 [SMILES: Cc1ccc(Cl)cc1S(=O)(=O)N1Cc2ccccc2COCC1Cc1ccccc1] | 442.0 | 464; 466 of [M + Na]+ |
| 1/21 | 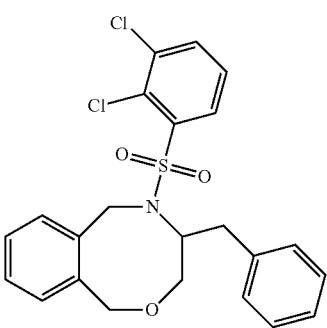 [SMILES: O=S(=O)(c1cccc(Cl)c1Cl)N1Cc2ccccc2COCC1Cc1ccccc1] | 462.4 | 484; 486 of [M + Na]+ |

-continued

| # | Structure | MW (g/mol) | Measured m/z of [M + H]+ |
|---|---|---|---|
| 1/22 | 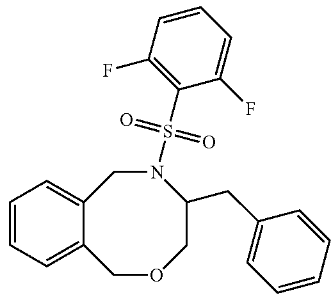 [SMILES: O=S(=O)(c1c(F)cccc1F)N1Cc2ccccc2COCC1Cc1ccccc1] | 429.5 | 430 |
| 1/23 | 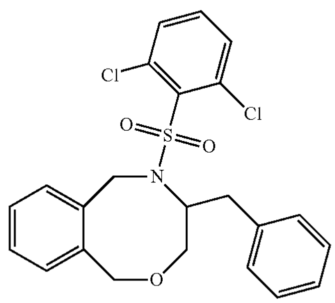 [SMILES: O=S(=O)(c1c(Cl)cccc1Cl)N1Cc2ccccc2COCC1Cc1ccccc1] | 462.4 | 484; 486 of [M + Na]+ |
| 1/24 | 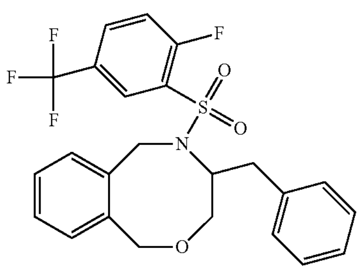 [SMILES: O=S(=O)(c1cc(C(F)(F)F)ccc1F)N1Cc2ccccc2COCC1Cc1ccccc1] | 479.5 | 480 |
| 1/25 | 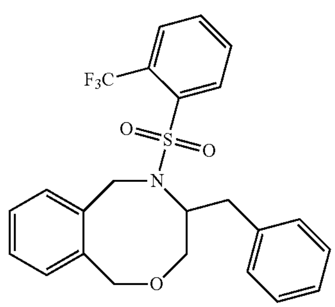 [SMILES: O=S(=O)(c1ccccc1C(F)(F)F)N1Cc2ccccc2COCC1Cc1ccccc1] | 461.5 | 462 |
| 1/26 | 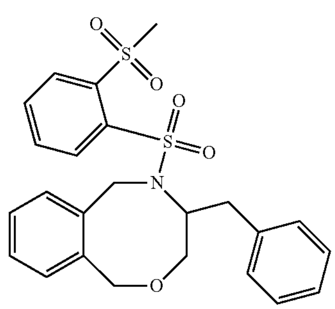 [SMILES: CS(=O)(=O)c1ccccc1S(=O)(=O)N1Cc2ccccc2COCC1Cc1ccccc1] | 471.6 | 472 |

-continued

| # | Structure | MW (g/mol) | Measured m/z of [M + H]+ |
|---|---|---|---|
| 1/27 | 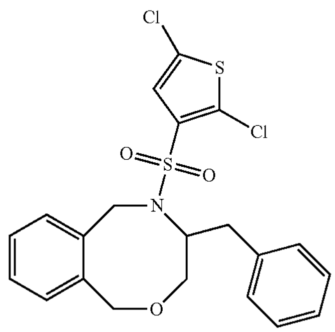 [SMILES: O=S(=O)(c1cc(Cl)sc1Cl)N1Cc2ccccc2COCC1Cc1ccccc1] | 468.4 | 468, 470 |
| 1/28 | 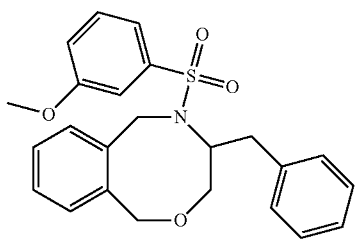 [SMILES: COc1cccc(S(=O)(=O)N2Cc3ccccc3COCC2Cc2ccccc2)c1] | 423.5 | 424 |
| 1/29 | 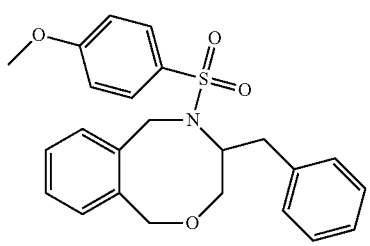 [SMILES: COc1ccc(S(=O)(=O)N2Cc3ccccc3COCC2Cc2ccccc2)cc1] | 423.5 | 424 |
| 1/30 | 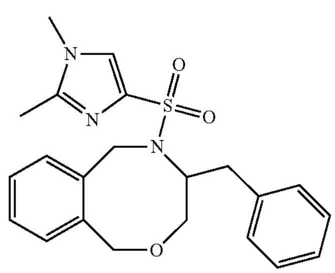 [SMILES: Cc1nc(S(=O)(=O)N2Cc3ccccc3COCC2Cc2ccccc2)cn1C] | 411.5 | 412 |
| 1/31 | 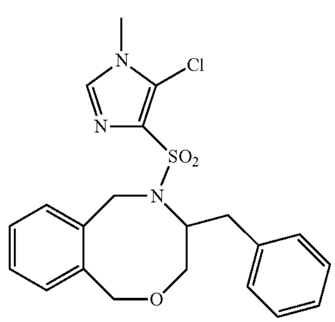 [SMILES: Cn1cnc(S(=O)(=O)N2Cc3ccccc3COCC2Cc2ccccc2)c1Cl] | 431.9 | 432;434 |

-continued

| # | Structure | MW (g/mol) | Measured m/z of [M + H]$^+$ |
|---|---|---|---|
| 1/32 | 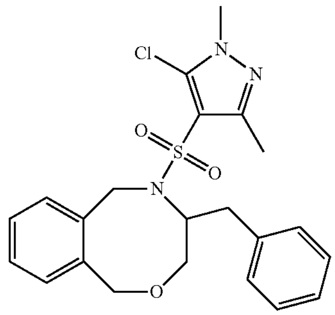 [SMILES: Cc1nn(C)c(Cl)c1S(=O)(=O)N1Cc2ccccc2COCC1Cc1ccccc1] | 446.0 | 446; 448 |
| 1/33 | 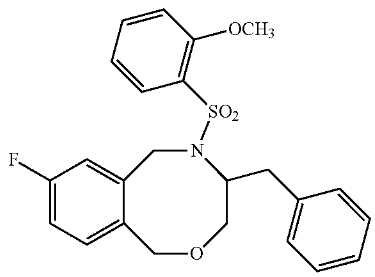 [SMILES: COc1ccccc1S(=O)(=O)N1Cc2cc(F)ccc2COCC1Cc1ccccc1] | 441.5 | 442 |
| 1/34 | 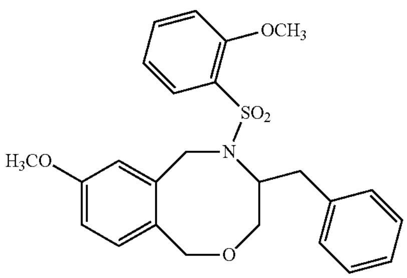 [SMILES: COc1ccc2c(c1)CN(S(=O)(=O)c1ccccc1OC)C(Cc1ccccc1)COC2] | 453.6 | 454 |
| 1/35 | 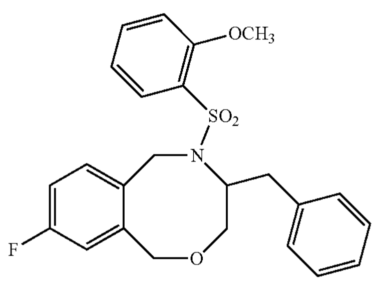 [SMILES: COc1ccccc1S(=O)(=O)N1Cc2ccc(F)cc2COCC1Cc1ccccc1] | 441.5 | 442 |
| 1/36 | 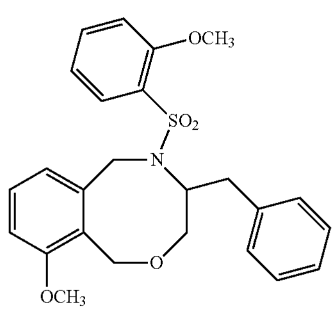 [SMILES: COc1ccccc1S(=O)(=O)N1Cc2cccc(OC)c2COCC1Cc1ccccc1] | 453.6 | 454 |

-continued
| # | Structure | MW (g/mol) | Measured m/z of [M + H]+ |
|---|---|---|---|
| 1/37 | 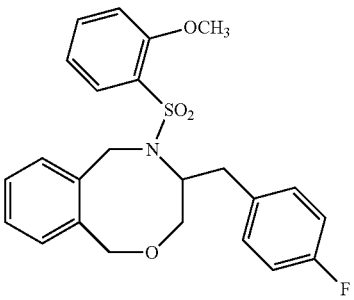 [SMILES: COc1ccccc1S(=O)(=O)N1Cc2ccccc2COCC1Cc1ccc(F)cc1] | 441.5 | 442 |
| 1/38 | 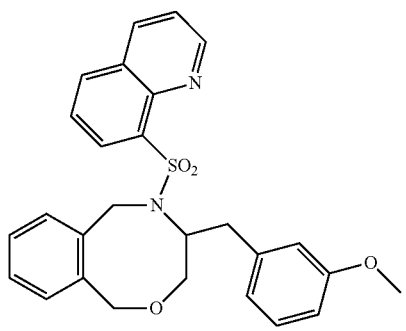 [SMILES: COc1cccc(CC2COCc3ccccc3CN2S(=O)(=O)c2cccc3cccnc23)c1] | 474.6 | 475 |
| 1/39 | 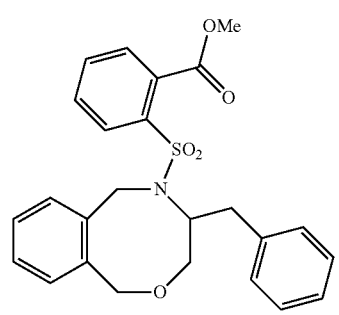 [SMILES: COC(=O)c1ccccc1S(=O)(=O)N1Cc2ccccc2COCC1Cc1ccccc1] | 451.5 | 452 |
| 1/40 | 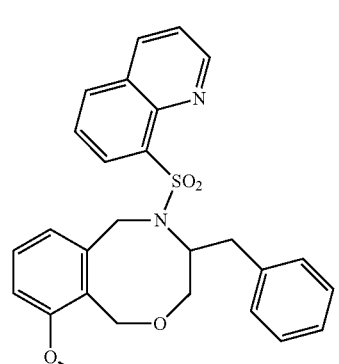 | 474.6 | 475 |
| 1/41 | 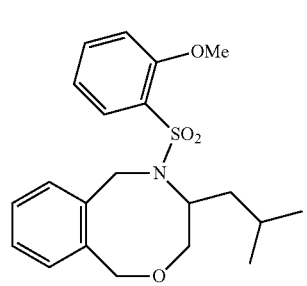 [SMILES: COc1ccccc1S(=O)(=O)N1Cc2ccccc2COCC1CC(C)C] | 389.5 | 390 |

-continued
| # | Structure | MW (g/mol) | Measured m/z of [M + H]+ |
|---|---|---|---|
| 1/42 | 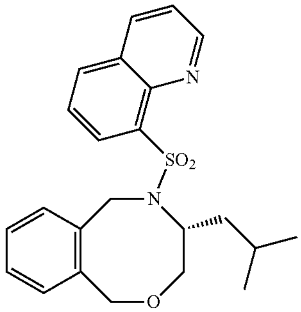 [SMILES: CC(C)C[C@@H]1COCc2ccccc2CN1S(=O)(=O)c1cccc2cccnc12] | 410.5 | 411 |
| 1/43 | 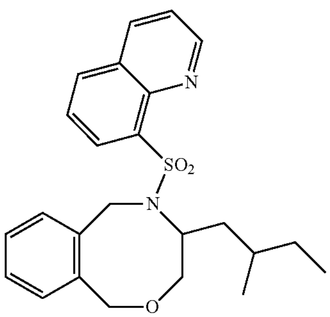 [SMILES: CCC(C)CC1COCc2ccccc2CN1S(=O)(=O)c1cccc2cccnc12] | 424.5 | 425 |
| 1/44 | 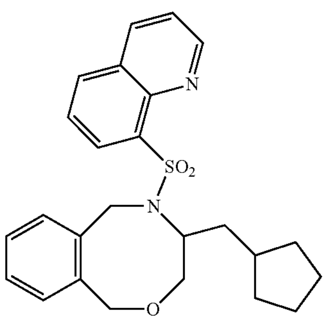 [SMILES: O=S(=O)(c1cccc2cccnc12)N1Cc2ccccc2COCC1CC1CCCC1] | 436.6 | 437 |
Preparative Example 2, 2g and 2h
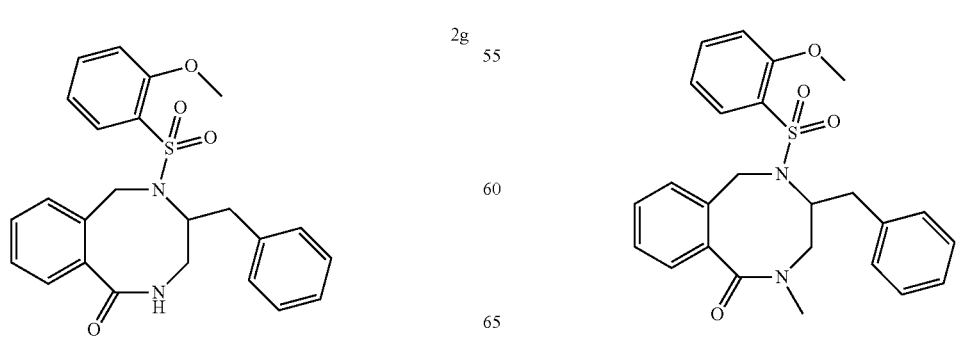

-continued

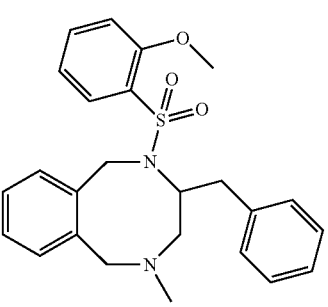

Step 1: 2-(2-Amino-3-phenylpropyl)isoindoline-1,3-dione (2b)

A solution of 2-(2-tert-butyloxycarbonylamino-3-phenylpropyl)isoindoline-1,3-dione (1.14 g, 3 mmol) in TFA (5 mL) and DCM (30 mL) was stirred at rt for 2 h. The solution was concentrated to give the compound as white solid which was dissolved in $Na_2CO_3$ (sat.) and extracted by EA (3×50 mL). The organic phase was washed with brine (20 mL) and dried over anhydrous $Na_2SO_4$ and concentrated in vacuo to give compound 2b as colorless oil (800 mg, yield 95%).

Step 2: N-(1-(1,3-Dioxoisoindolin-2-yl)-3-phenylpropan-2-yl)-2-methoxybenzenesulfonamide (2c)

To a solution of compound 2b (800 mg, 2.8 mmol) in pyridine (20 mL) was added 2-methoxybenzene-1-sulfonyl chloride (942 mg, 4.5 mmol) at 10° C. The mixture was stirred at rt overnight and then concentrated in vacuo. The residue was dissolved in DCM (20 mL), washed with water (20 mL) and brine (20 mL). The organic layer was dried over anhydrous $Na_2SO_4$ and concentrated in vacuo. The residue was purified by silica gel flash chromatography (PE:EA=2:1) to give compound 2c as a white solid (1.13 g, 83% yield).

Step 3: Methyl 2-((N-(1-(1,3-dioxoisoindolin-2-yl)-3-phenylpropan-2-yl)-2-methoxyphenyl-sulfonamido)methyl)benzoate (2d)

To a solution of compound 2c (500 mg, 1.1 mmol) in DMF (10 mL) at 10° C., NaH (60 wt %, 44 mg, 1.1 mmol) was added in portions. The mixture was stirred for an additional 30 min and then the solution of methyl 2-(bromomethyl)-benzoate (253 mg, 1.1 mmol) in DMF (2 mL) was added dropwise. The resulting mixture was stirred at 10° C. for 30 min and warmed to rt overnight. The reaction was quenched with water and diluted with EA (40 mL), washed with brine (3×20 mL). The organic phase was dried over anhydrous $Na_2SO_4$ and concentrated in vacuo. The residue was purification by silica gel flash chromatography (PE:EA=2:1) to give compound 2d as a white solid (520 mg, 79% yield).

Step 4: 2-((N-(1-(1,3-Dioxoisoindolin-2-yl)-3-phenylpropan-2-yl)-2-methoxyphenylsulfonamido)methyl)benzoic acid (2e)

To the solution of compound 2d (100 mg, 0.17 mmol) in $H_2O$ (2 mL) and MeOH (10 mL) was added aqueous NaOH (33 mg, 0.84 mmol). The resulting mixture was heated to reflux for 2 hr. Then the mixture was cooled to rt and acidified to pH=3 with 3.5N aqueous HCl, concentrated in vacuo to remove the volatile solvent. The resulting mixture was extracted with EA (2×30 mL). The organic extracts were combined and dried over anhydrous $Na_2SO_4$, concentrated in vacuo to give compound 2e as a white solid (80 mg, 80% yield).

Step 5: 2-((N-(1-Amino-3-phenylpropan-2-yl)-2-methoxyphenylsulfonamido)methyl)-benzoic acid (2f)

The mixture of compound 2e (100 mg, 0.17 mmol) and hydrazine monohydrate 98% (85 mg, 1.7 mmol) in ethanol (5 mL) was heated to reflux for 2 hr. The reaction mixture was cooled down to rt and acidified to pH=3 with 1N aqueous HCl. The precipitate was removed by filtration and the filtrate was concentrated in vacuo. The residue was purified by prep-HPLC to give compound 2f as a white solid (30 mg, 39% yield).

Step 6: 4-Benzyl-5-(2-methoxyphenylsulfonyl)-3,4,5,6-tetrahydrobenzo[f][1,4]diazocin-1(2H)-one (2g)

To a solution of compound 2f (45 mg, 0.1 mmol) in dry DMF (15 mL) was added 4-methylmorpholine (33 mg, 0.32 mmol). The mixture was stirred at rt for 10 min and DPPA (41 mg, 0.15 mmol) was added. This resulting mixture was stirred at rt for 24 h and then concentrated in vacuo to remove the solvent. The residue was dissolved in EA (10 mL), washed with saturated aqueous $NH_4Cl$ and brine, dried over anhydrous $Na_2SO_4$. Concentration in vacuo and purification by prep-TLC gave compound 2g as a white solid (40 mg, 91% yield). $^1$H-NMR (400 MHz, $CDCl_3$) δ 8.03 (dd, 1H, J=8.0, 1.6 Hz), 7.47-6.99 (m, 11H), 6.86 (d, 1H, J=8.0 Hz), 6.15 (m, 1H), 5.02 (d, J=15.6 Hz, 1H), 4.22 (d, J=15.6 Hz, 1H), 4.18 (m, 1H), 3.76 (s, 3H), 3.20 (dd, J=15.2, 8.8 Hz, 1H), 3.02-2.88 (m, 2H), 2.39 (d, J=8.8 Hz, 1H). MS (ESI+) m/z: 437 $[M+H]^+$, 459 $[M+Na]^+$.

Step 7: 4-Benzyl-5-(2-methoxyphenylsulfonyl)-2-methyl-3,4,5,6-tetrahydrobenzo[f][1,4]diazocin-1(2H)-one (2h)

To a solution of compound 2g (120 mg, 0.28 mmol) in DMF (15 mL) at 10° C., NaH (60% in mineral oil; 13 mg, 0.33 mmol) was added in portions. The mixture was stirred for an additional 45 min and then MeI (116 mg, 0.82 mmol) was added dropwise. The resulting mixture was stirred at 10° C. for 30 min and warmed to rt overnight. The reaction was quenched with water (30 mL) and extracted with EA (40 mL). The organic layer was washed with brine (2×20 mL) and dried over anhydrous $Na_2SO_4$. Concentration in vacuo and purification by prep-TLC (PE:EA=1:1) gave compound 2h as a white solid (110 mg, 89% yield). $^1$H-NMR (400 MHz, $CD_3OD$) δ 7.82 (dd, 1H, J=8.0, 1.6 Hz), 7.51 (t, J=8.8 Hz, 1H), 7.36-7.23 (m, 4H), 7.05-6.99 (m, 5H), 6.72-6.70 (m, 2H), 5.41 (d, J=18.8 Hz, 1H), 4.55 (d, J=19.2 Hz, 1H), 4.10 (m, 1H), 3.82 (s, 3H), 3.28 (dd, J=14.4, 11.6 Hz, 1H), 2.98 (dd, J=15.2, 4.8 Hz, 1H), 2.86 (s, 3H), 2.61 (dd, J=12.8, 9.6 Hz, 1H), 2.47 (dd, J=12.8, 4.8 Hz, 1H). MS (ESI+) m/z: 451 $[M+H]^+$

Step 8: 3-Benzyl-2-(2-methoxyphenylsulfonyl)-5-methyl-1,2,3,4,5,6-hexahydrobenzo-[f][1,4]-diazocine (2)

To a solution of compound 2h (150 mg, 0.33 mmol) in tetrahydrofuran (10 mL) at 5° C., LAH (76 mg, 2 mmol) was added. The resulting mixture was heated to reflux for 2 h and then cooled to 5° C., quenched with one drop of water. The precipitate formed was removed by filtration. The filtrate was diluted with 1N aqueous NaOH and extracted with EA. The organic layer was washed with brine and dried over anhydrous $Na_2SO_4$, concentrated in vacuo. The residue was purified by prep-HPLC to give compound 2 as a yellow solid (20 mg, 13% yield). $^1$H-NMR (400 MHz, $CDCl_3$) δ 8.00 (dd, 1H, J=8.0, 2.0 Hz), 7.44 (m, 1H), 7.19-7.00 (m, 8H), 6.87-6.81 (m, 3H), 5.30 (d, J=17.6 Hz, 1H), 4.59-4.55 (m, 2H), 4.29 (m, 1H), 3.72 (s, 3H), 3.45 (d, J=12.4 Hz, 1H), 2.62 (dd, J=13.2, 10.4 Hz, 1H), 2.49-2.39 (m, 3H), 2.24 (s, 3H). MS (ESI+) m/z: 437 [M+H]$^+$ Preparative Example 3

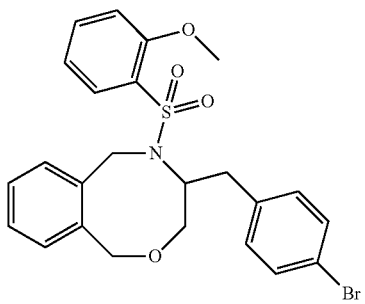

3

Step 1: Methyl 2-(bromomethyl)benzoate (3b)

To a solution of methyl 2-(methyl)benzoate 3a (9.46 g, 6.3 mmol) in chloroform (200 mL) were added NBS (13.8 g, 7.6 mmol) and benzoyl peroxide (760 mg, 0.32 mmol). The reaction mixture was stirred at reflux overnight. When the mixture was cooled to rt, filtered and concentrated. The residue was purified by CC, eluted with PE to give 3b as a colorless oil (9 g, 62% yield).

Step 2: Methyl 2-amino-3-(4-bromophenyl)propanoate (3d)

A mixture of 2-amino-3-(4-bromophenyl)propanoic acid 3c (24.4 g, 100 mmol) in HCl/MeOH (300 mL) was stirred at reflux overnight. TLC analysis indicated the total consumption of compound 3c. The mixture was concentrated to give 3d as a pale yellow solid (24 g, 92% yield).

Step 3: Methyl 3-(4-bromophenyl)-2-((tert-butoxycarbonyl)amino)propanoate (3e)

To a stirred mixture of compound 3d (24 g, 93 mmol) and TEA (19 g, 186 mmol) in DCM (300 mL) was added $(Boc)_2O$ (22 g, 102.3 mmol) at 0° C. Then the mixture was stirred at rt overnight. TLC analysis indicated the total consumption of compound 3d. Diluted HCl was added until the pH of the mixture was adjust to 7. Then the mixture was extracted with DCM (3×200 mL). The organic layer was washed with brine, dried over $Na_2SO_4$ and concentrated to give 3e as a pale yellow solid (32 g, 96% yield).

Step 4: tert-Butyl(1-(4-bromophenyl)-3-hydroxypropan-2-yl)carbamate (3f)

To a solution of compound 3e (15 g, 42 mmol) in ethanol (50 mL) and THF (50 mL) was added $LiCl.H_2O$ (10 g, 170 mmol) and $NaBH_4$ (6.3 g, 170 mmol) at 0° C. The mixture was stirred at rt overnight. LCMS analysis indicated the total consumption of compound 3e. The precipitate was removed by filtration and the filtrate was concentrated in vacuo to give 3f as a white solid (13 g, 94% yield).

Step 5: Methyl 2-((3-(4-bromophenyl)-2-((tert-butoxycarbonyl)amino)propoxy)methyl)-benzoate (3g)

To a solution of compound 3f (6.6 g, 20 mmol) in dry THF (100 mL) was added NaH (60%, 960 mg, 24 mmol) in small portions at 0° C. and stirred for 1 hr. Then compound 3b (5 g, 22 mmol) in THF (50 mL) was added dropwise, and the reaction mixture was allowed to stir at rt overnight. The reaction was quenched with water and extracted with EA (2×100 mL). The combined organic extracts were dried over anhydrous $Na_2SO_4$ and concentrated under reduced pressure. The residue was purified by CC eluting with PE:EA=9:1 to give 3g as a white solid (3.2 g, 34% yield).

Step 6: tert-Butyl(1-(4-bromophenyl)-3-((2-(hydroxymethyl)benzyl)oxy)propan-2-yl)carbamate (3h)

To a solution of compound 3g (5 g, 10 mmol) in dry ether (80 mL) was added slowly $LiAlH_4$ (1M in THF, 15.7 mL, 15.7 mmol) at 0° C. The mixture was stirred at 0° C. for 30 min. Then the mixture was quenched with water (1 mL) under vigorous stirring. The precipitate was removed by filtration and the filtrate was concentrated in vacuo to give 3h as a white solid (4.3 g, 92% yield).

Step 7: tert-Butyl(1-((2-(bromomethyl)benzyl)oxy)-3-(4-bromophenyl)propan-2-yl)carbamate (3i)

To a solution of compound 3h (4.15 g, 9.2 mmol) in dry THF (50 mL) was added NBS (4.1 g, 23 mmol) and $PPh_3$ (6 g, 23 mmol) at 0° C. The mixture was stirred at 0° C. for 20 min. Then the mixture was stirred at rt for 2 hr. The solvent was evaporated in vacuo and purified by CC eluting with PE:EA=4:1 to give 3i as a white solid (2.3 g, 50% yield).

Step 8: 1-((2-(Bromomethyl)benzyl)oxy)-3-(4-bromophenyl)propan-2-amine trifluoroacetic acid salt (3k)

To a solution of compound 3i (2.2 g, 4.3 mmol) in DCM (20 mL) was added slowly TFA (2 mL) at 0° C. The mixture was stirred at 0° C. for 2 hr. LCMS analysis indicated the total consumption of compound 3i. The solvent was removed in vacuum to give 3k as a white solid (1.68 g, 95% yield).

Step 9: 4-(4-Bromobenzyl)-3,4,5,6-tetrahydro-1H-benzo[f][1,4]oxazocine (3l)

A mixture of compound 3k (1.6 g, 3.9 mmol) and K₂CO₃ (1.6 g, 12 mmol) in dry THF (30 mL) was stirred at rt overnight. LCMS indicated the total consumption of compound 3k. The reaction mixture was filtered and the filtrate was evaporated in vacuum to give 3l as a white solid (1.1 g, 86% yield).

Step 10: 4-(4-Bromobenzyl)-5-((2-methoxyphenyl)sulfonyl)-3,4,5,6-tetrahydro-1H-benzo-[f][1,4]oxazocine (3)

To a mixture of compound 3l (900 mg, 2.7 mmol) and TEA (546 mg, 5.4 mmol) in acetonitrile (30 mL) was added 2-methoxybenzene sulfonyl chloride (559 mg, 2.7 mmol) and catalytic amount of DMAP. The reaction mixture was stirred at rt overnight. The solvent was evaporated in vacuo and purified by CC to give 3 as a white solid (510 mg, 38% yield).

Preparative Examples 3/1 to 3/2

Following similar procedures as described in the Preparative Example 3 the following compounds were prepared.

| # | Structure | MW (g/mol) | Measured m/z of [M + H]⁺ |
|---|---|---|---|
| 3/1 | 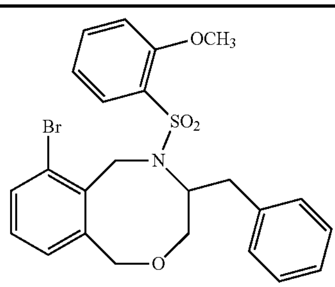 | 502.4 | 502; 504 |
| 3/2 | | 502.4 | 502; 504 |

Preparative Example 4

Following a similar procedure as described in *Org. Lett.* 2009, 11:5494, compound 4-benzyl-5-(2-methoxyphenylsulfonyl)-3,4,5,6-tetrahydro-2H-benzo[b][1,5]oxazocine (4) was prepared.

Preparative Examples 5/1 to 5/6

By using Pd-catalysed Br substitution the following compounds were prepared.

| # | Structure | SM # | MW (g/mol) | Measured m/z of [M + H]⁺ |
|---|---|---|---|---|
| 5/1 | 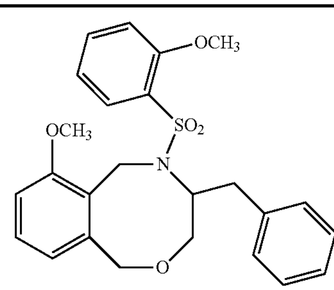 | 3/1 | 453.6 | 454 |
| 5/2 | 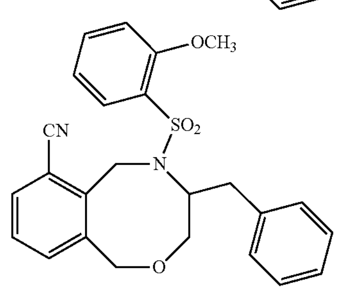 | 3/1 | 448.5 | 449 |

| # | Structure | SM # | MW (g/mol) | Measured m/z of [M + H]+ |
|---|-----------|------|------------|--------------------------|
| 5/3 | 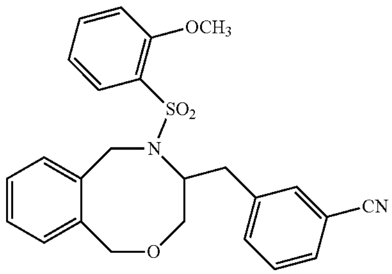 [SMILES: COc1ccccc1S(=O)(=O)N1Cc2ccccc2COCC1Cc1cccc(C#N)c1] | 3/2 | 448.5 | 449 |
| 5/4 | 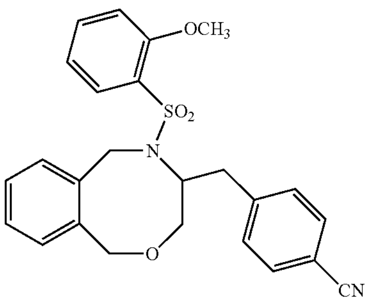 [SMILES: COc1ccccc1S(=O)(=O)N1Cc2ccccc2COCC1Cc1ccc(C#N)cc1] | 3 | 448.5 | 449 |
| 5/5 | 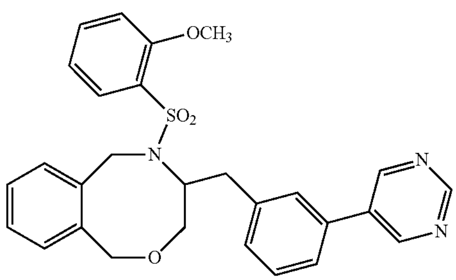 [SMILES: COc1ccccc1S(=O)(=O)N1Cc2ccccc2COCC1Cc1cccc(-c2cncnc2)c1] | 3/2 | 501.6 | 502 |
| 5/6 | 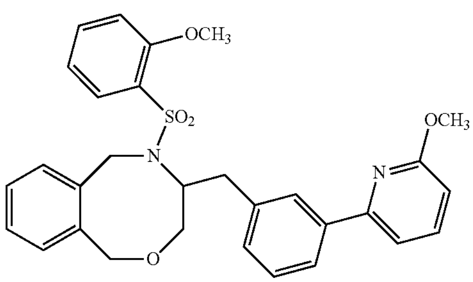 [SMILES: COc1cccc(-c2cccc(CC3COCc4ccccc4CN3S(=O)(=O)c3ccccc3OC)c2)n1] | 3/2 | 530.6 | 531 |
Preparative Example 6
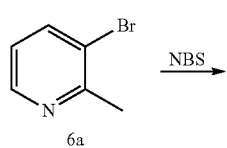
 NBS →
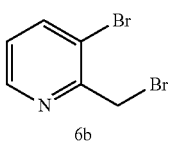
-continued
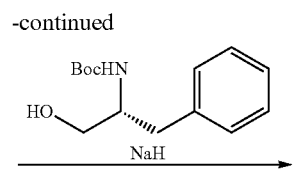

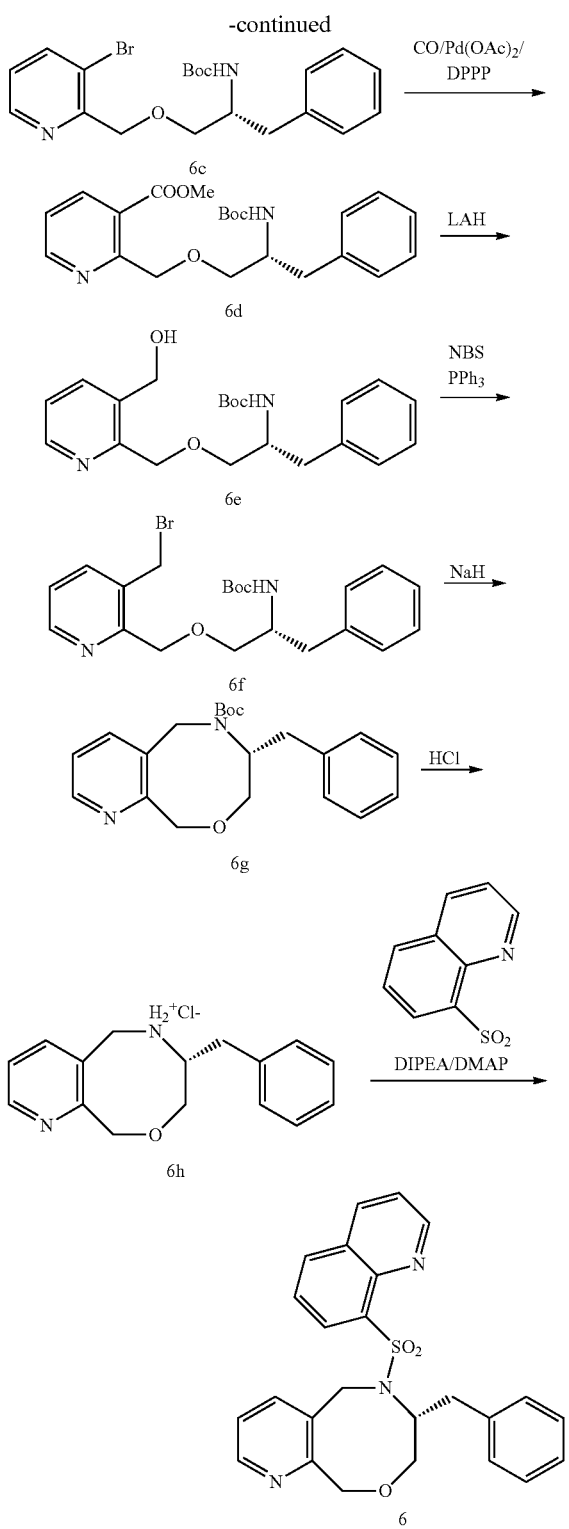

filtered and concentrated under reduced pressure. The residue was purified by CC on silica gel, eluting with PE:EA=15:1 to afford 6b (1.1 g, 78% yield) as a yellow oil.

Step 2: Compound 6c

To a solution of (R)-tert-butyl-1-hydroxy-3-phenylpropan-2-yl carbamate (200 mg, 0.8 mmol) in DMF (8 mL) at 0° C. was added NaH (29 mg, 1.2 mmol) in portions. The reaction mixture was stirred at rt for 10 min and 6b (200 mg, 0.8 mmol) was added. The mixture was stirred at rt for 16 h, quenched with H₂O and extracted with EA (3×30 mL). The combined organic layers were dried over Na₂SO₄, filtered and concentrated under reduced pressure. The crude product was purified by Prep-TLC to afford 6c (70 mg, 21% yield) as a colorless oil.

Step 3: Compound 6d

A mixture of 6c (1.3 g, 3 mmol), palladium acetate (106 mg, 0.5 mmol), 1,3-bis(diphenylphosphino)propane (635 mg, 1.54 mmol) and triethylamine (939 mg, 9.3 mmol) in MeOH (30 mL) was stirred at 120° C. under a carbon monoxide atmosphere (10 bar) for 30 h. The reaction mixture was cooled to rt and concentrated under reduced pressure. The crude product was purified by CC on silica gel, eluted with PE/EA=5:1 to afford 6d (840 mg, 68% yield) as a colorless oil.

Step 4: Compound 6e

To a solution of 6d (200 mg, 0.5 mmol) in diethylether (10 mL) at 0° C. was added LiAlH₄ (76 mg, 2 mmol). The reaction mixture was stirred at rt for 0.5 h and quenched with H₂O. The mixture was diluted with EA, dried over Na₂SO₄, filtered and concentrated under reduced pressure. The residue was purified by CC on silica gel, eluted with PE/EA=5:1 to afford 6e (181 mg, 97% yield) as a colorless oil.

Step 5: Compound 6f

To a solution of 6e (65 mg, 0.18 mmol) in THF at 0° C. was added NBS (78 mg, 0.44 mmol) followed by PPh₃ (115 mg, 0.44 mmol). The reaction mixture was stirred at rt for 2 h and concentrated under reduced pressure. The residue was purified by CC on silica gel, eluted with PE/EA=5:1 to afford 6f (28 mg, 37% yield) as a colorless oil.

Step 6: Compound 6g

To a solution of 6f (133 mg, 0.31 mmol) in DMF (40 mL) at 0° C. was added NaH (60%, 42 mg, 0.62 mmol) in portions. The reaction mixture was stirred at rt for 24 h, quenched with H₂O and extracted with EA (3×30 mL). The combined organic layers were dried over Na₂SO₄, filtered and concentrated under reduced pressure. The residue was purified by Prep-HPLC, eluted with PE/EA=5:1 to afford 6g (79 mg, 72% yield) as a colorless oil.

Step 7: Compound 6h

A solution of 6g (109 mg, 0.31 mmol) in EA-HCl (3 mL) was stirred at rt for 1 h and concentrated under reduced pressure to afford 6h (130 mg, 100%) as a white solid.

Step 8: (R)-7-Benzyl-6-(quinolin-8-ylsulfonyl)-6,7,8,10-tetrahydro-5H-pyrido[3,2-f][1,4]oxazocine (6)

To a solution of 6h (79 mg, 0.31 mmol) and DIPEA (120 mg, 0.93 mmol) in DCM (3 mL) at 0° C. was added quinoline- Step 1: Compound 6b A mixture of 6a (1 g, 5.8 mmol), benzoylperoxide (101 mg, 0.4 mmol) and NBS (1.1 g, 6.39 mmol) in CCl₄ (58 mL) was heated under reflux for 4 h. The reaction mixture was cooled to rt, quenched with H₂O and extracted with DCM (3×30 mL). The combined organic layers were dried over Na₂SO₄, 8-sulfonyl chloride (71 mg, 0.31 mmol) followed by DMAP (8 mg, 0.07 mmol). The reaction mixture was stirred at rt for 24 h and concentrated under reduced pressure. The residue was purified by CC on silica gel, eluted with PE/EA=5:1 to afford 6 (54 mg, 39%) as a white solid. $^1$H NMR (400 MHz, CDCl$_3$) δ 9.08 (s, 1H), 8.57 (d, J=8.0 Hz, 1H), 8.34-8.33 (m, 1H), 8.21 (d, 1H, J=8.0 Hz), 8.04 (d, 1H, J=8.0 Hz), 7.81 (d, 1H, J=8.0 Hz), 7.69 (t, 1H, J=8.0 Hz), 7.51-7.48 (m, 1H), 7.22-7.12 (m, 3H), 7.03-6.96 (m, 3H), 5.47 (d, 1H, J=16.0 Hz), 5.20-5.14 (m, 2H), 4.79 (d, 1H, J=16.0 Hz), 4.34 (m, 1H), 3.98 (d, 1H, J=8.4 Hz), 3.57-3.51 (m, 1H), 3.12 (m, 1H), 2.22 (m, 1H). MS (ESI+) m/z: 446.5 [M+H]$^+$.

Preparative Examples 6/1 to 6/5

Following similar procedures as described in the Preparative Example 6 the following compounds were prepared.

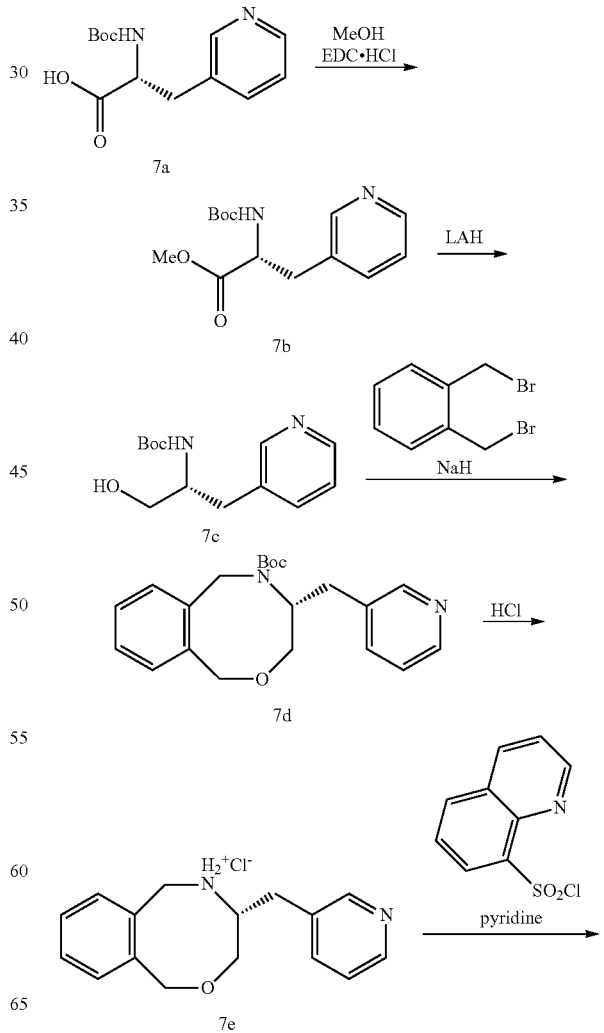

Preparative Example 7

-continued

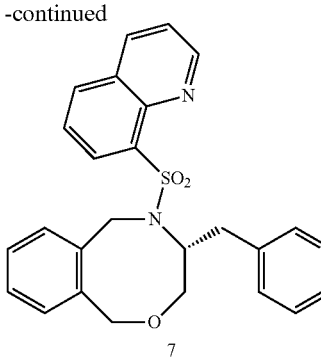

Step 1: Compound 7b

To a solution of 7a (110 mg, 0.41 mmol) and Et₃N (83 mg, 0.82 mmol) in MeOH (4 mL) was added EDC.HCl (118.5 mg, 0.62 mmol). The reaction mixture was stirred at rt for 3 h and concentrated under reduced pressure. The residue was partitioned between water and EA. The organic layer was dried over Na₂SO₄, filtered and concentrated under reduced pressure. The residue was purified by CC on silica gel, eluting with PE/EA=3:1 to 1:2 to afford 7b (89 mg, 77% yield) as a white solid.

Step 2: Compound 7c

To a solution of 7b (4.18 g, 15 mmol) in Et₂O (100 mL) at rt was slowly added LiAlH₄ (567 mg, 30 mmol). The reaction mixture was stirred for 0.5 h, quenched with H₂O and diluted with EA. The mixture was dried over Na₂SO₄, filtered and concentrated under reduced pressure to afford 7c (3.52 g, 93% yield) as a pale yellow oil.

Step 3: Compound 7d

To a solution of 7c (418 mg, 1.66 mmol) and 1,2-bis(bromomethyl)benzene (480 mg, 1.83 mmol) in dry DMF (3 mL) at 0° C. was added NaH (166 mg, 4.15 mmol). The reaction mixture was stirred at 0° C. for 1.5 h, quenched with H₂O and extracted with EA (10 mL). The organic layer was dried over Na₂SO₄, filtered and concentrated under reduced pressure. The residue was purified by CC on silica gel, eluting with PE/EA=5:1 to 1:1 to give 7d (92 mg, 15% yield).

Step 4: Compound 7e

A solution of 7d (92 mg, 0.26 mmol) in EA-HCl (3 mL) was stirred at rt for 1 h and filtered to afford 7e (73 mg, 100% yield) as a white solid.

Step 5: (R)-4-(Pyridin-3-ylmethyl)-5-(quinolin-8-ylsulfonyl)-3,4,5,6-tetrahydro-1H-benzo[f][1,4]oxazocine (7)

To a solution of 7e (73 mg, 0.25 mmol) in dry pyridine (2.5 mL) at rt was added quinoline-8-sulfonyl chloride (86 mg, 0.38 mmol). The reaction mixture was stirred at rt for 16 h and concentrated under reduced pressure. The residue was purified by Prep-TLC to give 7 (13 mg, 11%). ¹H NMR (400 MHz, CDCl₃) δ 8.89-8.87 (m, 1H), 8.56 (d, 1H, J=8.0 Hz), 8.45-8.40 (m, 2H), 8.16 (d, 1H, J=8.0 Hz), 8.00 (d, 2H, J=8.0 Hz), 7.62-7.58 (m, 2H), 7.45-7.42 (m, 1H), 7.20-7.17 (m, 2H), 7.02 (t, 1H, J=7.6 Hz), 6.93-6.86 (m, 3H), 5.10-5.01 (m, 3H), 4.62-4.57 (m, 2H), 3.82 (d, 1H, J=8.0 Hz), 3.79 (d, 1H, J=8.0 Hz), 3.15-3.09 (m, 1H), 2.63-2.60 (m, 1H). MS (ESI+) m/z: 446.2 [m+H]⁺.

Preparative Examples 8 and 9

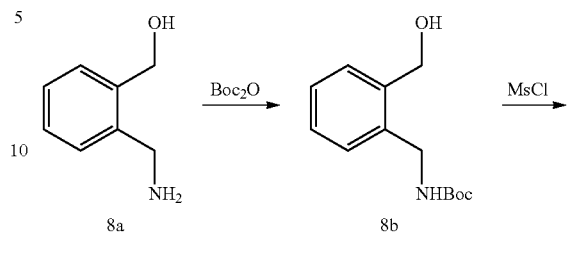

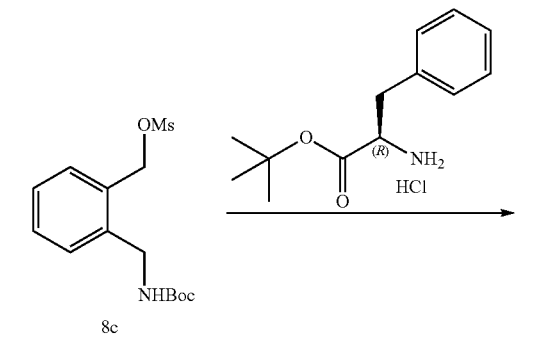

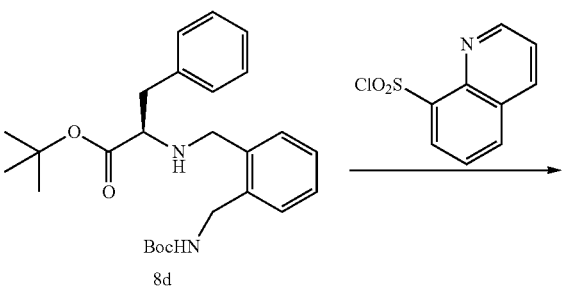

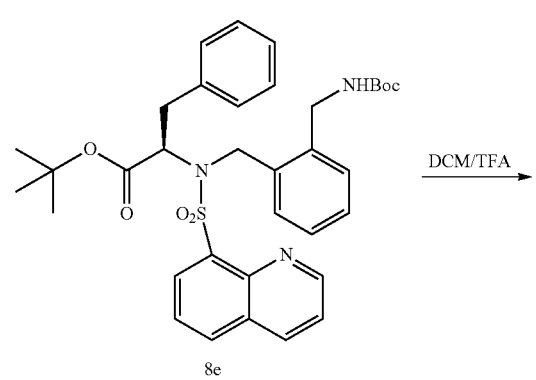

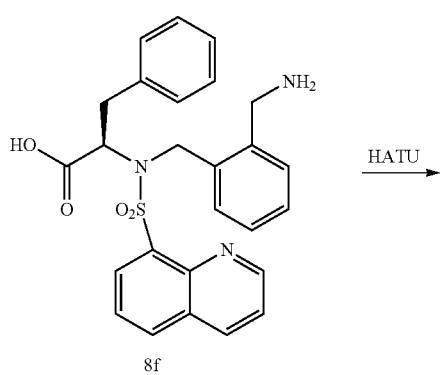

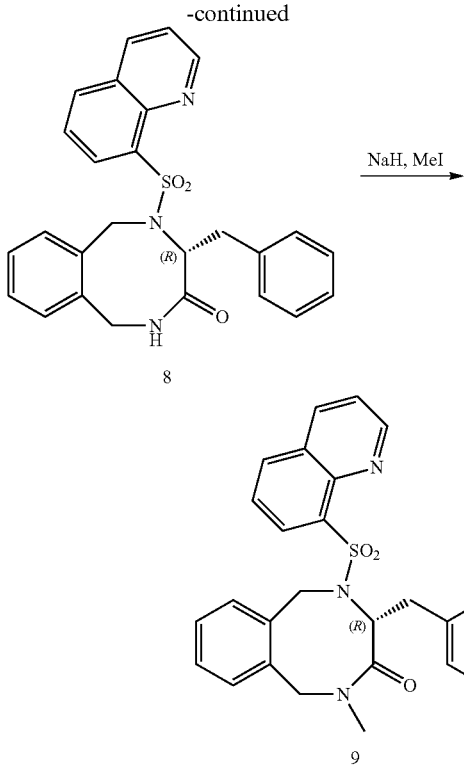

Step 1: Compound 8b

To a solution of 8a (4 g, 29.2 mmol) in DCM (20 mL) and MeOH (10 mL) was added Boc$_2$O (6.4 g, 29.2 mmol). The reaction mixture was stirred at rt for 24 h and concentrated under reduce pressure. The residue was purified by CC on silica gel, eluting with PE/EA=10:1 to 5:1 to give 8b (3.2 g, 46% yield) as a white solid.

Step 2: Compound 8c

To a solution of 8b (1 g, 4.21 mmol) in DCM (10 mL) at rt was added DIPEA (1.6 g, 12.4 mmol) followed by methanesulfonyl chloride. The mixture was stirred at rt for 3 h and concentrated under reduced pressure to give crude 8c (1.2 g, 100% yield) as a yellow oil.

Step 3: Compound 8d

To a solution of (R)-tert-butyl 2-amino-3-phenylpropanoate hydrochloride (1.08 g, 4.21 mmol) in dioxane (15 mL) was added DIPEA (1.6 g, 12.4 mmol) followed by 8c (1.2 g, 4.21 mmol). The mixture was heated under reflux for 14 h, cooled to rt and concentrated under reduced pressure. The residue was partitioned between EA (100 mL) and H$_2$O (50 mL). The organic layer was separated, washed with brine (50 mL), dried over Na$_2$SO$_4$, filtered and concentrated under reduced pressure. The residue was purified by CC on silica gel, eluting with PE/EA=10:1 to 2:1 to give 8d (1 g, 54% yield) as a pale yellow oil.

Step 4: Compound 8e

To a solution of 8d (1 g, 2.27 mmol) in pyridine (10 mL) at rt was added quinoline-8-sulfonyl chloride (0.517 g, 2.27 mmol). The mixture was stirred for 16 h and concentrated under reduced pressure. The residue was partitioned between EA (100 mL) and H$_2$O (50 mL). The organic layer was separated, washed with brine (30 mL), dried over Na$_2$SO$_4$, filtered and concentrated under reduced pressure. The residue was purified by CC on silica gel, eluting with PE/EA=5:1 to 1:1 to give 8e (620 mg, 44% yield) as a pale yellow oil.

Step 5: Compound 8f

A mixture of 8e (620 mg, 0.98 mmol) in DCM (2 mL) and TFA (5 mL) was stirred at rt for 4 h and concentrated under reduced pressure. The residue was partitioned between EA (100 mL) and sat. aq. NaHCO$_3$ (50 mL). The organic layer was separated, washed with brine (30 mL), dried over Na$_2$SO$_4$, filtered and concentrated under reduced pressure. The residue was purified by CC on silica gel, eluting with DCM/MeOH=20:1 to 8:1 to give 8f (400 mg, 86% yield) as a pale yellow oil.

Step 6: (R)-4-Benzyl-5-(quinolin-8-ylsulfonyl)-1,2,5,6-tetrahydrobenzo[f][1,4]diazocin-3(4H)-one (8)

To a solution of 8f (400 mg, 0.84 mmol) in DMF (5 mL) at rt was added HATU (479 mg, 1.26 mmol). The reaction mixture was stirred for 16 h, diluted with EA (20 mL) and washed with H$_2$O (20 mL) and brine (10 mL). The organic solution was dried over Na$_2$SO$_4$, filtered and concentrated under reduced pressure. The residue was purified by CC on silica gel, eluting with DCM-EA (10:1 to 2:1) to give crude product (200 mg), which was purified by Prep-TLC and crystallization from diethyl ether to give 8 (50 mg, 13% yield) as a white solid. $^1$H-NMR (400 MHz, CDCl$_3$) δ 9.01-8.99 (m, 1H), 8.24 (d, J=7.2 Hz, 1H), 8.18 (d, J=8.0 Hz, 1H), 7.93 (d, J=8.0 Hz, 1H), 7.51-7.40 (m, 2H), 7.30-7.20 (m, 2H), 7.12 (t, J=7.6 Hz, 1H), 7.10-6.95 (m, 5H), 6.81 (d, J=7.2 Hz, 1H), 5.96 (t, J=6.8 Hz, 1H), 5.45-5.36 (m, 2H), 5.08-5.03 (m, 1H), 4.45 (d, J=16.8 Hz, 1H), 3.77-3.71 (m, 1H), 3.32-3.25 (m, 1H), 2.90-2.87 (m, 1H); MS (ESI+) m/z: 458 [M+H]$^+$.

Step 7: (R)-4-Benzyl-2-methyl-5-(quinolin-8-ylsulfonyl)-1,2,5,6-tetrahydrobenzo[f][1,4]diazocin-3(4H)-one (9)

To a solution of 8 (50 mg, 0.11 mmol) in THF (3 mL) at −10° C. was slowly added NaH (5.2 mg, 0.12 mmol). The mixture was warmed to rt and stirred for 1 h. To it was added CH$_3$I (50 mg, 0.33 mmol). The reaction mixture was stirred at rt for 16 h, diluted with H$_2$O (10 mL) and extracted with EA (2×20 mL). The combined organic layers were dried over Na$_2$SO$_4$, filtered and concentrated under reduced pressure. The residue was purified by Prep-TLC to give 9 (50 mg, 96% yield) as a white solid. $^1$H-NMR (400 MHz, CDCl$_3$) δ 9.14-9.11 (m, 1H), 8.24-8.19 (m, 2H), 7.92 (d, J=8.0 Hz, 1H), 7.59-7.54 (m, 1H), 7.44-7.36 (m, 3H), 7.22-7.13 (m, 5H), 7.08-7.04 (m, 1H), 6.72 (d, J=7.2 Hz, 1H), 5.80-5.76 (m, 1H), 5.43-5.30 (m, 2H), 4.20 (d, J=16.8 Hz, 1H), 3.46-3.30 (m, 2H), 3.06-3.00 (m, 1H), 2.75 (s, 3H); MS (ESI+) m/z: 472 [M+H]$^+$.

Preparative Example 10 and 11

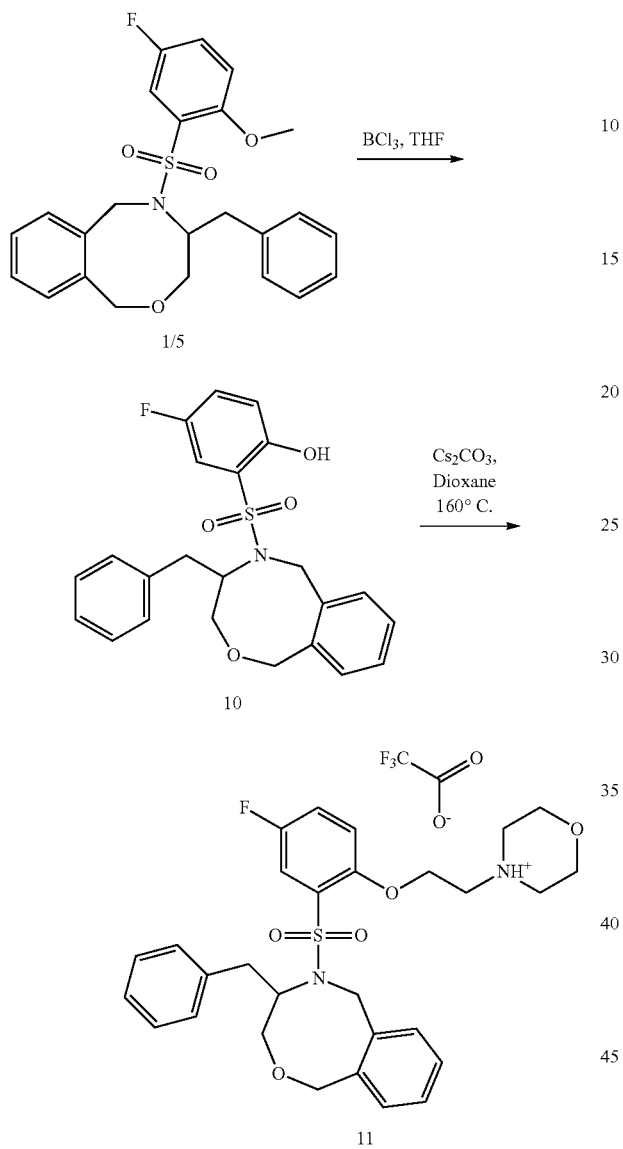

Step 1: 2-(4-Benzyl-3,4-dihydro-1H-benzo[f][1,4]oxazocin-5(6H)-ylsulfonyl)-4-fluorophenol (10)

To a mixture of compound Example 1/5 (441 mg, 1 mmol) in THF (10 mL), was added $BCl_3$ (234 mg, 2 mmol) at −78° C. and stirred overnight at rt. The solvent was evaporated in vacuo and purified by CC to give compound 10 as a white solid (400 mg, 90% yield).

Step 2: (R)-4-Benzyl-5-(quinolin-8-ylsulfonyl)-1,2,5,6-tetrahydrobenzo[f][1,4]diazocin-3(4H)-one (11)

A mixture of 10 (43 mg, 0.1 mmol), cesium carbonate (130 mg, 0.4 mmol) and 4-(2-chloroethyl)-morpholine (45 mg, 0.3 mmol) in 1,4-dioxane (3 mL) was heated in a microwave oven at 160° C. for 2 h. The reaction mixture was filtrated and the solvent was removed at reduced pressure. The residue was purified by prep-HPLC to give compound 11 as a white solid (20 mg, 30% yield). $^1$H-NMR (400 MHz, $CDCl_3$) δ 7.65-7.60 (m, 1H), 7.37-7.02 (m, 9H), 6.83 (br s, 2H), 5.35-5.31 (m, 1H), 5.10-4.90 (m, 3H), 3.83-3.75 (m, 2H), 3.65-3.61 (m, 4H), 3.43-3.41 (m, 1H), 3.32-3.18 (m, 2H), 3.00-2.90 (m, 1H), 2.86-2.79 (m, 1H), 2.41-2.20 (m, 6H). MS (ESI+) m/z: 541.2 [M+H]$^+$.

Preparative Example 12

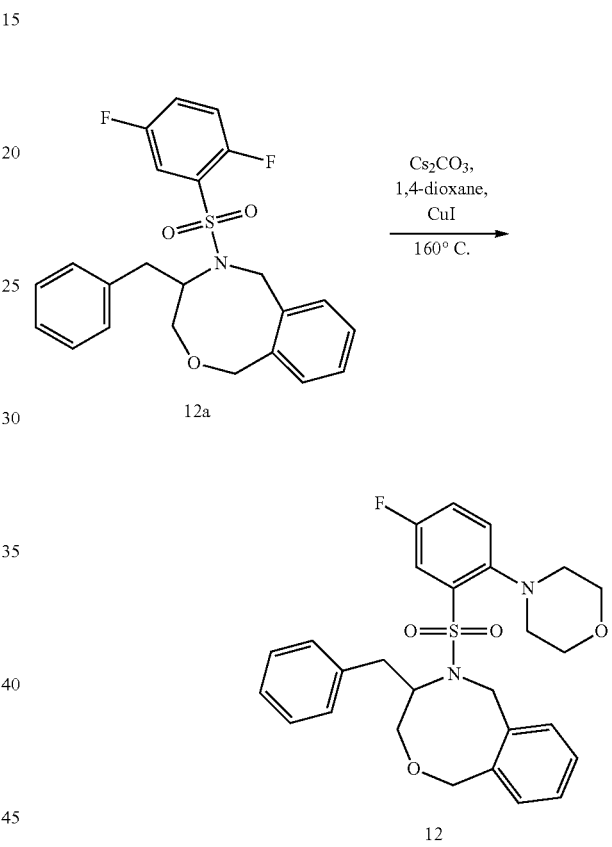

A mixture of 12a (prepared similar as Prep. Ex. 1; 43 mg, 0.1 mmol), cesium carbonate (130 mg, 0.4 mmol), CuI (10 mg, 0.05 mmol) and morpholine (35 mg, 0.4 mmol) in 1,4-dioxane (3 mL) was heated in a microwave oven at 160° C. for 2 h. After cooling to rt the reaction mixture was filtered and the solvent was removed under reduced pressure. The residue was purified by prep-HPLC to give 4-benzyl-5-(5-fluoro-2-morpholinophenylsulfonyl)-3,4,5,6-tetrahydro-1H-benzo[f][1,4]oxazocine (12) as a white solid (30 mg, 61% yield). $^1$H NMR (400 MHz, $CDCl_3$) δ 7.70-7.68 (m, 1H), 7.35-7.15 (m, 8H), 7.10 (d, J=6.4 Hz, 2H), 6.96 (d, J=6.5 Hz, 1H), 5.16 (d, J=12.5 Hz, 1H), 5.04 (d, J=12.5 Hz, 1H), 4.89 (d, J=12.5 Hz, 1H), 4.65 (d, J=12.5 Hz, 1H), 4.25-4.21 (m, 1H), 3.91-3.85 (m, 2H), 3.79-3.65 (m, 3H), 3.51-3.46 (m, 1H), 3.32-3.25 (m, 1H), 3.14 (t, J=10 Hz, 1H), 2.58-2.50 (m, 2H), 2.38-2.31 (m, 1H), MS (ESI+) m/z: 497.0 [M+H]$^+$.

Preparative Example 13

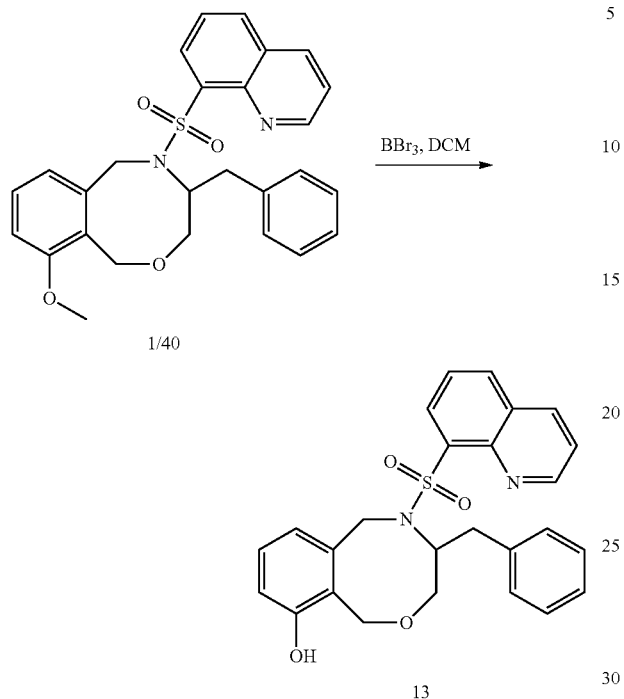

To Preparative Example 1/40 (474 mg, 1 mmol) in dry DCM (10 mL) at −78° C. was added BBr₃ (1 mL, 2M in DCM, 2 mol) and the mixture was stirred at −78° C. for 2 h. Saturated aq. NH₄Cl (5 mL) was added to quench the reaction. The organic layer was separated and the aqueous layer was extracted with DCM. The organic layer was washed with brine and dried over anhydrous Na₂SO₄. The solvent was removed under reduced pressure and the residue was purified by CC to give 4-benzyl-5-(quinolin-8-ylsulfonyl)-3,4,5,6-tetrahydro-1H-benzo[f][1,4]oxazocin-10-ol (13) as a white solid (312 mg, 68% yield). MS (ESI+) m/z: 461.1 [M+H]⁺.

Preparative Example 14, 15 and 16

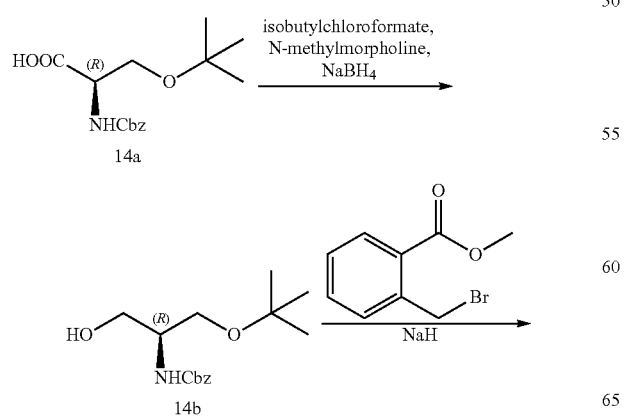

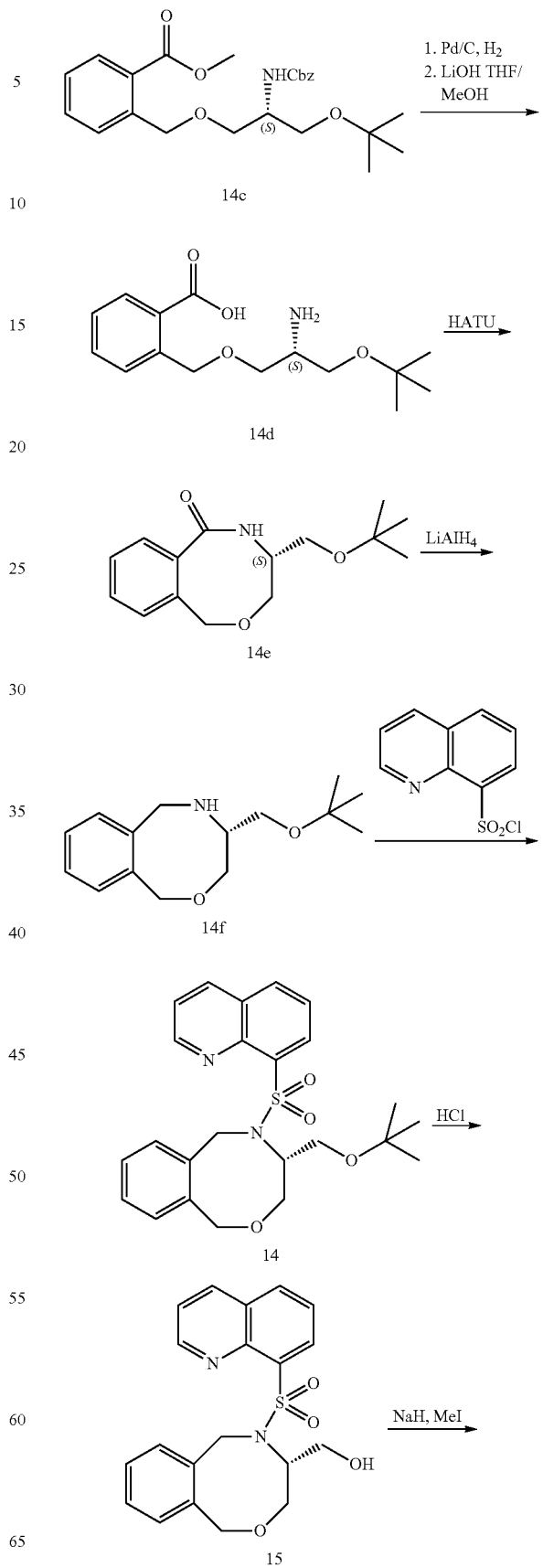

-continued

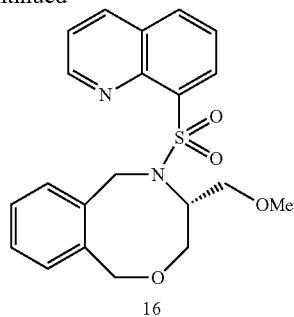

16

Step 1: (S)-Benzyl (1-(tert-butoxy)-3-hydroxypropan-2-yl)carbamate (14b)

To a solution of compound 14a (5 g, 17 mmol) and isobutyl chloroformate (2.79 g, 20.4 mmol) in THF (60 mL) at −20° C. was added N-methylmorpholine (2.06 g, 20.4 mmol). The reaction mixture was stirred for 10 min and filtered. The filtrate was cooled to −20° C. and to it was added NaBH$_4$ (969 mg, 25.5 mmol) followed by H$_2$O (40 mL). The mixture was stirred for 30 min, poured into H$_2$O and extracted with EA (150 mL). The organic layer was dried over Na$_2$SO$_4$, filtered and concentrated under reduced pressure to give compound 14b (4.14 g, 87% yield) as an oil.

Step 2: (S)-Methyl 2-((2-(((benzyloxy)carbonyl)amino)-3-(tert-butoxy)propoxy)methyl)benzoate (14c)

To a solution of compound 14b (562 mg, 2.0 mmol) in DMF (10 mL) at 0° C. was added NaH (200 mg, 5.0 mmol). The reaction was stirred for 30 min and to it was added methyl 2-(bromomethyl)benzoate (366 mg, 1.6 mmol). The reaction mixture was stirred for 3 h, poured into H$_2$O and extracted with EA (10 mL). The organic layer was dried over Na$_2$SO$_4$, filtered and concentrated under reduced pressure. The residue was purified by Prep-TLC to give compound 14c (275 mg, 40% yield) as an oil.

Step 3: (S)-2-((2-Amino-3-(tert-butoxy)propoxy)methyl)benzoic acid (14d)

A mixture of compound 14c (1.4 g, 3.3 mmol) and Pd-C (37 mg) in MeOH (20 mL) was stirred under a H$_2$ atmosphere (1 atm) at rt for 16 h. The reaction mixture was filtered and concentrated under reduced pressure. The residue was purified by CC on silica gel to give the ester (900 mg, 92% yield) as an oil. To a solution of this ester (900 mg, 3.05 mmol) in THF (10 mL) at 0° C. was added a solution of LiOH (513 mg, 12.2 mmol) in H$_2$O (3 mL). The reaction mixture was stirred at rt for 16 h, acidified with 1N HCl to pH=3 and extracted with EA (3×15 mL). The combined organic layers were dried over Na$_2$SO$_4$, filtered and concentrated under reduced pressure to give compound 14d (720 mg, 84% yield) as a white solid.

Step 4: (S)-4-(tert-Butoxymethyl)-4,5-dihydro-1H-benzo[f][1,4]oxazocin-6(3H)-one (14e)

To a solution of compound 14d (394 mg, 1.4 mmol) and HATU (639 mg, 1.68 mmol) in DMF (20 mL) at rt was added DIPEA (1 mL). The reaction mixture is stirred for 16 h, quenched with H$_2$O and extracted with EA (100 mL). The organic layer was dried over Na$_2$SO$_4$, filtered and concentrated under reduced pressure. The residue was purified by CC on silica gel, eluting with PE/EA=4:1 to give compound 14e (171 mg, 46% yield) as a yellow solid.

Step 5: (S)-4-(tert-Butoxymethyl)-3,4,5,6-tetrahydro-1H-benzo[f][1,4]oxazocine (14f)

To a solution of compound 14e (171 mg, 0.65 mmol) in THF (6 mL) at 0° C. was added LiAlH$_4$ (247 mg, 6.5 mmol). The reaction mixture was heated under reflux for 16 h, cooled to rt, quenched with H$_2$O and filtered. The mixture was extracted with CHCl$_3$ (10 mL), washed with brine, dried over Na$_2$SO$_4$, filtered and concentrated under reduced pressure. The residue was washed with hexanes to give compound 14f (129 mg), which was used in the next step without further purification.

Step 6: (S)-4-(tert-Butoxymethyl)-5-(quinolin-8-ylsulfonyl)-3,4,5,6-tetrahydro-1H-benzo[f][1,4]oxazocine (14)

To a mixture of compound 14f (crude, 129 mg, 0.5 mmol) in pyridine (4 mL) at rt was added quinoline-8-sulfonyl chloride (142 mg, 0.6 mmol). The reaction mixture was stirred for 16 h and concentrated under reduced pressure. The residue was partitioned between CHCl$_3$ and H$_2$O. The organic layer was washed with brine, dried over Na$_2$SO$_4$, filtered and concentrated under reduced pressure. The residue was purified by Prep-TLC to give compound 14 (100 mg, 44% yield). $^1$H NMR (400 MHz, CDCl$_3$) δ 8.97 (s, 1H), 8.49 (d, 1H, J=8.0 Hz), 8.17 (d, 1H, J=8.0 Hz), 7.97 (d, 1H, J=8.0 Hz), 7.56 (t, 1H, J=8.0 Hz), 7.47-7.44 (m, 1H), 7.21 (d, 1H, J=8.0 Hz), 7.02-7.00 (m, 1H), 6.94-6.93 (m, 1H), 6.87 (d, 1H, J=8.0 Hz), 5.17 (d, 1H, J=8.0 Hz), 4.98-4.93 (m, 2H), 4.66 (d, 1H, J=8.0 Hz), 4.51 (s, 1H), 4.27 (d, 1H, J=8.0 Hz), 3.78 (d, 1H, J=8.0 Hz), 3.53 (t, 1H, J=7.2 Hz), 3.21-3.18 (m, 1H), 1.00 (s, 9H). MS (ESI) calcd for [C$_{24}$H$_{28}$N$_2$O$_4$S+H]$^+$ (m/z): 441.56. found: 441.3.

Step 7: (R)-(5-(Quinolin-5-ylsulfonyl)-3,4,5,6-tetrahydro-1H-benzo[f][1,4]oxazocin-4-yl)methanol (15)

A solution of compound 14 (58 mg, 0.13 mmol) in HCl-MeOH (1M, 5 mL) was stirred at rt for 24 h. The solvent was removed under reduced pressure to give compound 15 (45 mg, 89% yield) as a solid. $^1$H NMR (400 MHz, CDCl$_3$) δ 8.94-8.93 (m, 1H), 8.59 (d, 1H, J=8.0 Hz), 8.22 (d, 1H, J=8.0 Hz), 8.03 (d, 1H, J=8.0 Hz), 7.63 (t, 1H, J=8.0 Hz), 7.51-7.47 (m, 1H), 7.03 (t, 2H, J=8.0 Hz), 6.94-6.87 (m, 2H), 4.94 (d, 2H, J=8.0 Hz), 4.85-4.80 (m, 2H), 4.60 (d, 1H, J=8.0 Hz), 4.24-4.19 (m, 1H), 3.82 (d, 1H, J=8.0 Hz), 3.73-3.71 (t, 2H), 2.79-2.76 (m, 1H). MS (ESI) calcd for [C$_{20}$H$_{20}$N$_2$O$_4$S+H]$^+$ (m/z): 385.45. found: 384.8.

Step 8: (R)-4-(Methoxymethyl)-5-(quinolin-8-ylsulfonyl)-3,4,5,6-tetrahydro-1H-benzo[f][1,4]oxazocine (16)

To a solution of compound 15 (40 mg, 0.1 mmol) in DMF (3 mL) at 0° C. was added NaH (168 mg, 0.4 mmol). The mixture was stirred at rt for 0.5 h and to it was added MeI (22 mg, 0.16 mmol). The reaction was stirred at rt for 2.5 h, quenched with H$_2$O and extracted with EA (3×10 mL). The combined organic layers were washed with brine, dried over Na₂SO₄, filtered and concentrated under reduced pressure. The residue was purified by Prep-TLC to give compound 16 (22 mg, 53% yield) as a solid. ¹H NMR (400 MHz, CDCl₃) δ 8.93 (s, 1H), 8.51 (d, 1H, J=8.0 Hz), 8.16 (d, 1H, J=8.0 Hz), 7.97 (d, 1H, J=8.0 Hz), 7.60 (t, 1H, J=8.0 Hz), 7.46-7.43 (m, 1H), 7.18 (d, 1H, J=8.0 Hz), 7.00 (d, 1H, J=7.6 Hz), 6.91-6.82 (m, 2H), 5.12 (d, 1H, J=8.0 Hz), 4.99-4.90 (m, 2H), 4.72 (s, 1H), 4.62-4.59 (d, 1H), 4.23 (d, 1H, J=8.0 Hz), 3.76 (d, 1H, J=8.8 Hz), 3.60 (t, 1H, J=8.0 Hz), 3.33-3.29 (m, 1H), 3.17 (s, 3H). MS (ESI) calcd for $[C_{21}H_{22}N_2O_4S+H]^+$ (m/z): 399.48. found: 399.2.

Preparative Examples 16/1 to 16/4

Following similar procedures as described in the Preparative Example 14 to 16, Step 8 the following compounds were prepared.

| # | Structure | MW (g/mol) | Measured m/z of [M + H]⁺ |
|---|-----------|------------|--------------------------|
| 16/1 | 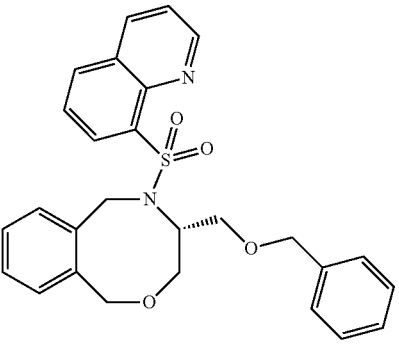 [SMILES: O=S(=O)(c1cccc2cccnc12)N1Cc2ccccc2COC[C@H]1COCc1ccccc1] | 474.6 | 475.2 |
| 16/2 | 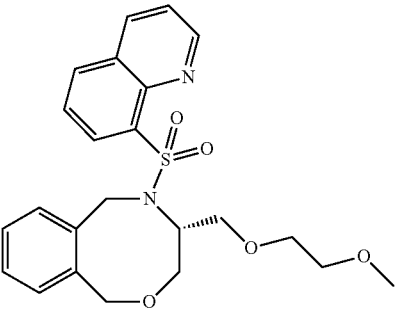 [SMILES: COCCOC[C@@H]1COCc2ccccc2CN1S(=O)(=O)c1cccc2cccnc12] | 442.5 | 443.0 |
| 16/3 | 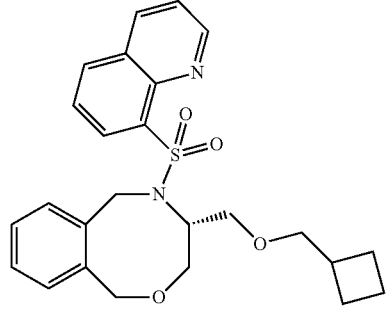 [SMILES: O=S(=O)(c1cccc2cccnc12)N1Cc2ccccc2COC[C@H]1COCC1CCC1] | 452.6 | 453.3 |
| 16/4 | 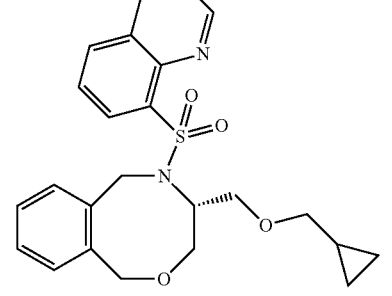 | 438.5 | 439.2 |

Preparative Example 17

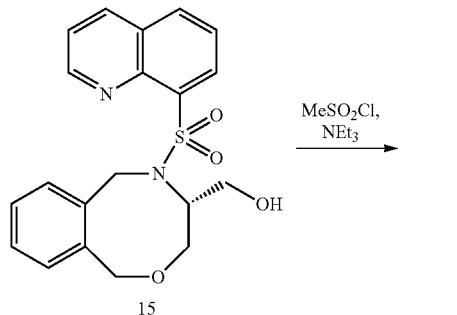

15

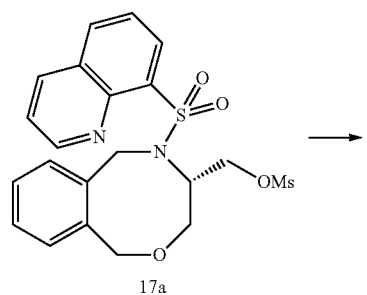

17a

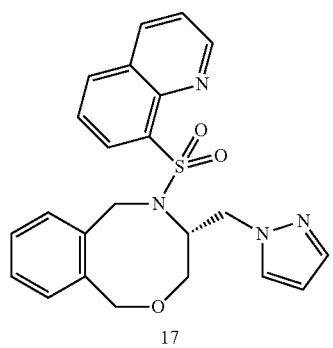

17

Step 1: (S)-(5-(Quinolin-8-ylsulfonyl)-3,4,5,6-tetrahydro-1H-benzo[f][1,4]oxazocin-4-yl)methyl methanesulfonate (17a)

To the mixture of compound 15 (200 mg, 0.52 mmol) and TEA (0.2 mL, 1.5 mmol) in THF (25 mL) at rt, methanesulfonyl chloride (71 mg, 0.62 mmol) was added. The resulting mixture was stirred at rt for overnight. The reaction mixture was poured in ice water (100 mL), extracted with EA (3×100 mL). The combined organic layer was washed with water (100 mL) and brine (100 mL), dried over anhydrous $Na_2SO_4$. Concentration in vacuo and purified by CC, eluting with PE:EA=2:1 afforded compound 17a as white solid (210 mg, 87% yield).

Step 2: (R)-4-((1H-Pyrazol-1-yl)methyl)-5-(quinolin-8-ylsulfonyl)-3,4,5,6-tetrahydro-1H-benzo[f][1,4]oxazocine (17)

Compound 17a (100 mg, 0.21 mmol) was added to DMSO (1 mL) and $Cs_2CO_3$ (500 mg, 1.5 mmol). 1H-Pyrazole (70 mg, 1.0 mmol) was added in the mixture and sealed in a microwave tube. The mixture was heated to 110° C. for 30 min under microwave irradiation. The reaction mixture was poured into ice/water (50 mL) and extracted with EA (3×50 mL) and washed with brine (2×50 mL) and dried over anhydrous $Na_2SO_4$. The residue was purified by CC eluting with PE:EA=3:1 to give compound 17 as white solid (30 mg, 32% yield). $^1$H-NMR (400 MHz, $CD_3OD$) δ: 8.73 (d, J=1.6 Hz, 1H), 8.33 (d, J=7.2 Hz, 1H), 8.20 (d, 1H), 7.97 (d, 1H), 7.52-7.50 (m, 2H), 7.40-7.38 (m, 2H), 6.80 (d, 1H), 6.70 (t, 1H), 6.14 (s, 1H), 5.10 (m, 1H), 4.92 (d, J=14.4 Hz, 1H), 4.80 (m, 2H), 4.43 (d, J=14.4 Hz, 1H), 4.35 (q, 1H), 4.22 (q, 1H), 3.76 (d, 1H), 3.66 (d, 1H). MS (ESI+) m/z: 435.0 $[M+H]^+$.

Preparative Examples 17/1 to 17/5

Following similar procedures as described in the Preparative Example 17, Step 2 the following compounds were prepared.

| # | Structure | MW (g/mol) | Measured m/z of $[M + H]^+$ |
|---|---|---|---|
| 17/1 | 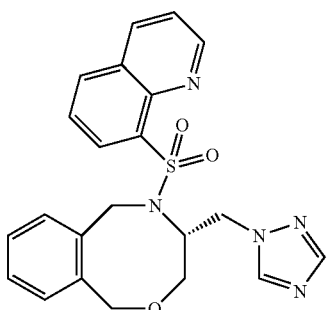 | 435.5 | 436.2 |

-continued
| # | Structure | MW (g/mol) | Measured m/z of [M + H]+ |
|---|---|---|---|
| 17/2 | 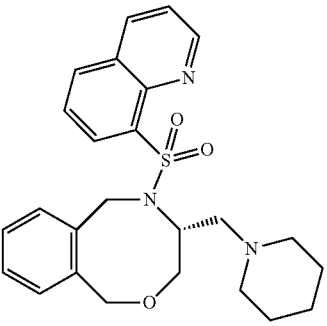 [SMILES: O=S(=O)(c1cccc2cccnc12)N1Cc2ccccc2COC[C@H]1CN1CCCCC1] | 451.6 | 452.4 |
| 17/3 | 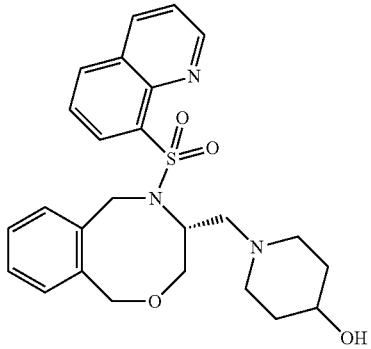 [SMILES: O=S(=O)(c1cccc2cccnc12)N1Cc2ccccc2COC[C@H]1CN1CCC(O)CC1] | 467.6 | 468.3 |
| 17/4 | 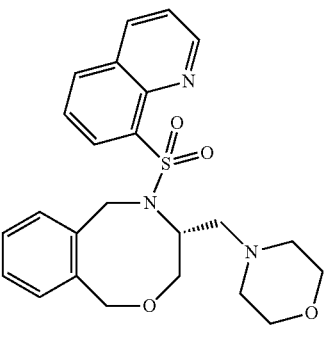 [SMILES: O=S(=O)(c1cccc2cccnc12)N1Cc2ccccc2COC[C@H]1CN1CCOCC1] | 453.6 | 454.4 |
| 17/5 | 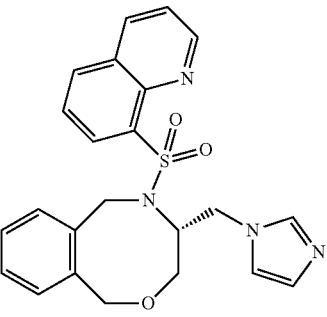 [SMILES: O=S(=O)(c1cccc2cccnc12)N1Cc2ccccc2COC[C@H]1Cn1ccnc1] | 434.5 | 435.4 |

Preparative Example 18

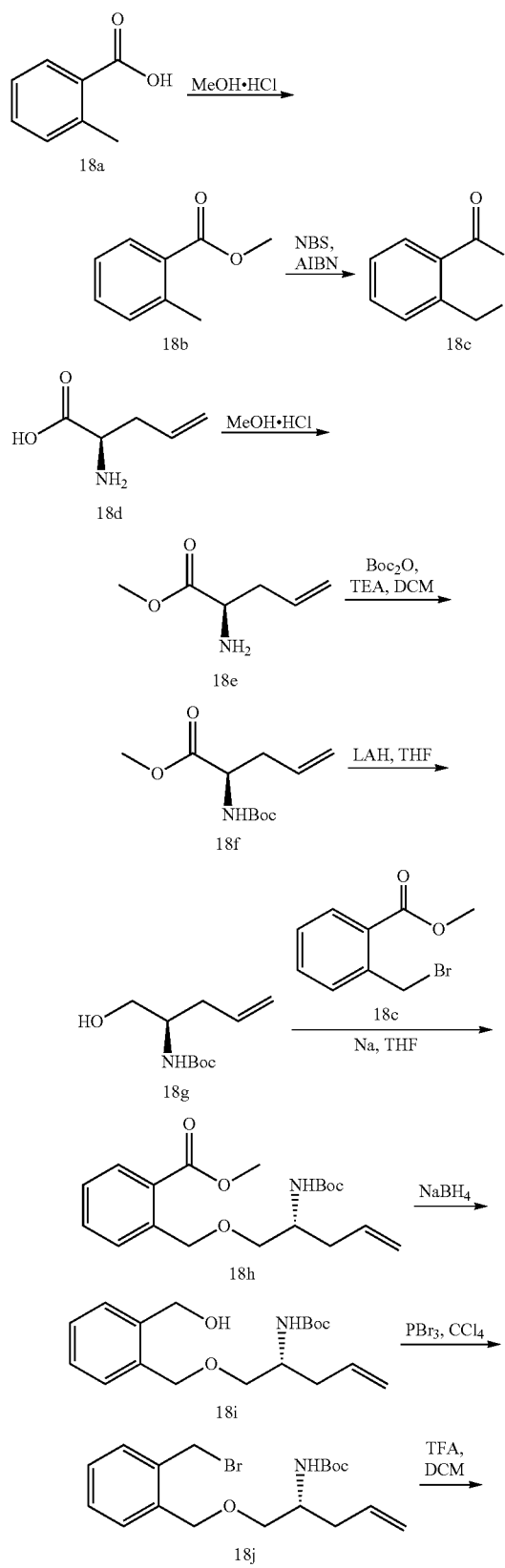

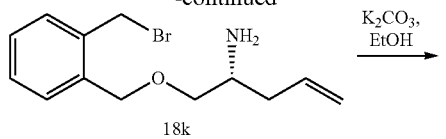

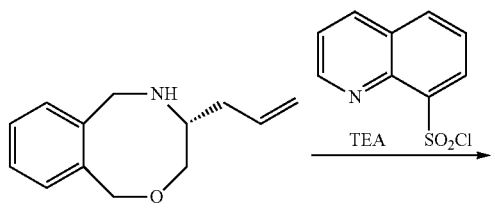

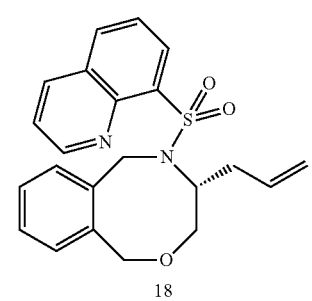

Step 1: Methyl 2-methylbenzoate (18b)

A solution of 2-methylbenzoic acid (18a) (5 g, 36.8 mmol) in MeOH.HCl (2.4M, 50 mL) was stirred at 70° C. overnight. The mixture was concentrated under reduced pressure to give compound 18b (4.5 g, 82% yield), which was used without purification.

Step 2: Methyl 2-(bromomethyl)benzoate (18c)

A solution of compound 18b (4.5 g, 30 mmol), NBS (5.9 g, 33 mmol) and AIBN (0.5 g, 3 mmol) in CCl$_4$ (20 mL) was refluxed overnight. The mixture was taken up in H$_2$O (20 mL) and extracted with DCM (100 mL). The organic layer was washed with brine, dried over Na$_2$SO$_4$, filtered and concentrated. The crude product was purified by CC to give the compound 18c (5.5 g, 80% yield).

Step 3: (R)-Methyl 2-aminopent-4-enoate (18e)

A solution of (R)-2-aminopent-4-enoic acid (18d) (5 g, 43.5 mmol) in MeOH.HCl (2.4M, 50 mL) was stirred at 70° C. overnight. The mixture was concentrated under reduced pressure to give compound 18e (5.5 g, 98% yield), which was used without purification.

Step 4: (R)-Methyl 2-((tert-butoxycarbonyl)amino) pent-4-enoate (18f)

A solution of compound 18e (5.5 g, 42.6 mmol) in DCM (50 mL) containing Boc$_2$O (12.1 g, 55.4 mmol) and TEA (9.4 g, 85.2 mmol) was stirred at rt for 1 hr. The mixture was concentrated under reduced pressure to give compound 18f (9.5 g, 98% yield), which was used without purification.

Step 5: (R)-tert-Butyl(1-hydroxypent-4-en-2-yl)carbamate (18g)

A solution of compound 18f (9.5 g, 41.5 mmol) in THF (50 mL) was cooled in an ice bath under argon. To this mixture was added LAH (3.9 g, 104 mmol) portionwise, and then the ice bath was removed and the reaction mixture was allowed to stir at rt for 2 h and then quenched with water (30 mL). The aqueous layer was extracted with EA (3×50 mL). The combined extracts were washed with brine, dried over $Na_2SO_4$, filtered, concentrated and purified by CC to give compound 18g (6.2 g, 75% yield) as yellow oil.

Step 6: (R)-Methyl 2-(((2-((tert-butoxycarbonyl)amino)pent-4-en-1-yl)oxy)methyl)benzoate (18h)

A solution of compound 18g (6.2 g, 30.8 mmol) and compound 18c (8.5 g, 36.9 mmol) in THF (30 mL) was cooled in an ice bath under argon. To this mixture was added NaH (2.5 g, 61.6 mmol, 60% wt in oil) portionwise. The ice bath was removed and the reaction mixture was allowed to stir at rt for 2 h and then quenched with MeOH (10 mL). The mixture was concentrated under reduced pressure and the residue was purified by CC to give the desired compound 18h (4.2 g, 39% yield) as a yellow oil. LCMS (m/z): 350.2 (MH+).

Step 7: (R)-tert-Butyl(1-((2-(hydroxymethyl)benzyl)oxy)pent-4-en-2-yl)carbamate (18i)

A solution of compound 18h (4.2 g, 12.0 mmol) in EtOH/THF (30 mL, v/v=1/1) was treated with $CaCl_2$ (5.3 g, 48.0 mmol) and the resulting slurry was cooled under argon in an ice bath. To this mixture was added $NaBH_4$ (3.6 g, 96 mmol) portionwise. After 1 h the ice bath was removed and the reaction mixture was allowed to stir at rt for 16 hr. The mixture was quenched with 10% aq. $Na_2CO_3$ and water and the resulting thick, white slurry was extracted with EtOAc (3×50 mL). The combined organic layers were washed with brine, dried over $Na_2SO_4$ and concentrated. The crude product was purified by CC to give the desired compound 18i (3.0 g, 78% yield) as yellow oil. LCMS (m/z): 322.1 (MH+).

Step 8: (R)-tert-Butyl(1-((2-(bromomethyl)benzyl)oxy)pent-4-en-2-yl)carbamate (18j)

A solution of compound 18i (3.0 g, 9 mmol) in $CCl_4$ (10 mL) was cooled in an ice bath. To this mixture was added $PBr_3$ (1.0 g, 4.5 mmol) dropwise and the mixture was stirred at 0° C. for 2 hr. The mixture was quenched with water and extracted with DCM (3×50 mL). The combined organic layers were washed with brine and concentrated. The crude compound 18j (2.8 g, 80% yield) was used in the next step without purification. LCMS (m/z): 385.1 (MH+).

Step 9: (R)-1-((2-(Bromomethyl)benzyl)oxy)pent-4-en-2-amine (18k)

A solution of compound 18j (2.8 g, 7.3 mmol) in TFA/DCM (25 mL, v/v=1/4) was stirred at rt for 1 hr. The mixture was concentrated under reduced pressure to give compound 18k (2.0 g, 98% yield), which was used without purification. LCMS (m/z): 285.1 (MH+).

Step 10: (R)-4-Allyl-3,4,5,6-tetrahydro-1H-benzo[f][1,4]oxazocine (18l)

To a solution of compound 18k (2.0 g, 7.0 mmol) in EtOH (20 mL) was added $K_2CO_3$ (4.8 g, 35.0 mmol) portionwise. The mixture was heated to reflux for 2 h to complete the reaction. The reaction mixture was cooled down to rt and concentrated under reduced pressure to give compound 18l (1.2 g, 84% yield), which was used without purification. LCMS (m/z): 204.1 (MH+).

Step 11: (R)-4-Allyl-5-(quinolin-8-ylsulfonyl)-3,4,5,6-tetrahydro-1H-benzo[f][1,4]oxazocine (18)

A solution of compound 18l (1.2 g, 5.9 mmol), quinoline-8-sulfonyl chloride (1.5 g, 6.5 mmol), TEA (1.8 g, 17.7 mmol) and DMAP (366 mg, 3 mmol) in 20 mL of DCM was stirred at rt overnight. The mixture was concentrated and the residue was purified by CC to give the desired compound 18 (1.3 g, 56% yield) as a white solid. $^1$H NMR (500 MHz, $CDCl_3$) δ 8.94 (m, 1H), 8.46 (d, J=7.5 Hz, 1H), 8.13 (d, J=8.5 Hz, 1H), 7.93 (d, J=8.0 Hz, 1H), 7.54 (t, J=8.0 Hz, 1H), 7.43 (dd, J=4.0, 8.0 Hz, 1H), 7.20 (d, J=7.5 Hz, 1H), 6.98 (m, 1H), 6.91 (m, 1H), 6.80 (d, J=7.5 Hz, 1H), 5.69 (m, 1H), 5.07-4.86 (m, 5H), 4.58 (d, J=15.0 Hz, 1H), 4.54 (m, 1H), 4.01 (d, J=12.5 Hz, 1H), 3.68 (d, J=12.5 Hz, 1H), 2.47 (m, 1H), 2.09 (m, 1H). LCMS (m/z): 395.5 (MH+).

Preparative Example 20

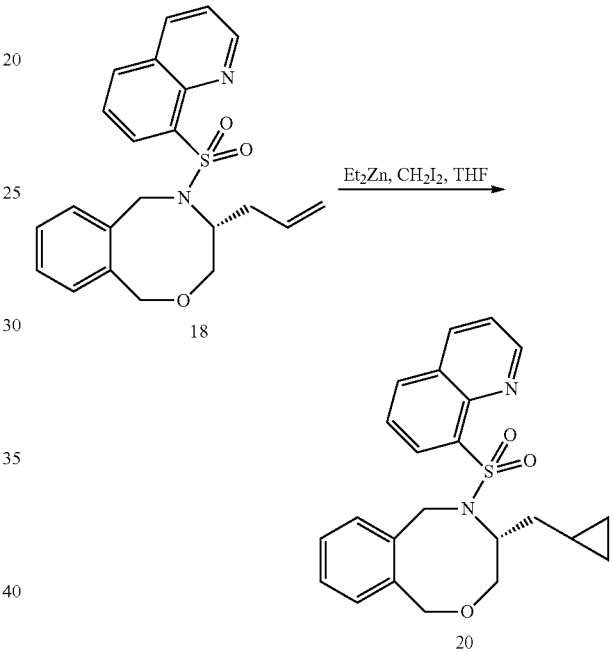

Step 1: (R)-4-(Cyclopropylmethyl)-5-(quinolin-8-ylsulfonyl)-3,4,5,6-tetrahydro-1H-benzo[f][1,4]oxazocine (20)

To a stirred solution of compound 18 (100 mg, 0.25 mmol) in dry THF (5 mL) was added diethyl zinc (1M solution in hexane, 2.5 mL) at 0° C. under nitrogen atmosphere followed by diiodomethane (667 mg, 2.5 mmol). The reaction was stirred at 0° C. for 6 h and poured over cold aqueous solution of ammonium chloride. The organic layer was separated and the aqueous layer extracted repeatedly with EA. The combined organic layer was washed with brine, dried over $Na_2SO_4$, filtered and concentrated. The crude product was purified by Prep-TLC to afford the compound 20 (32 mg, 31% yield). $^1$H NMR (500 MHz, $CDCl_3$) δ 8.94 (m, 1H), 8.47 (d, J=7.5 Hz, 1H), 8.13 (d, J=8.0 Hz, 1H), 7.93 (d, J=8.5 Hz, 1H), 7.55 (t, J=8.0 Hz, 1H), 7.43 (dd, J=8.0 Hz, 4.0 Hz 1H), 7.17 (d, J=7.5 Hz, 1H), 6.98 (t, J=7.5 Hz, 1H), 6.89 (m, 1H), 6.80 (d, J=7.5 Hz, 1H), 5.07 (d, J=15.5 Hz, 1H), 4.95 (d, J=15.0 Hz, 1H), 4.86 (d, J=15.5 Hz, 1H), 4.60 (d, J=15.0 Hz, 1H), 4.49 (m, 1H), 4.14 (d, J=12.0 Hz, 1H), 3.75 (d, J=12.0 Hz, 1H), 1.71 (m, 1H), 1.10 (m, 1H), 0.63 (m, 1H), 0.33 (m, 2H), −0.11 (m, 2H). MS (ESI+) m/z: 409 [M+H]$^+$. LCMS (m/z): 409.2 (MH+).

Preparative Example 21 and 22

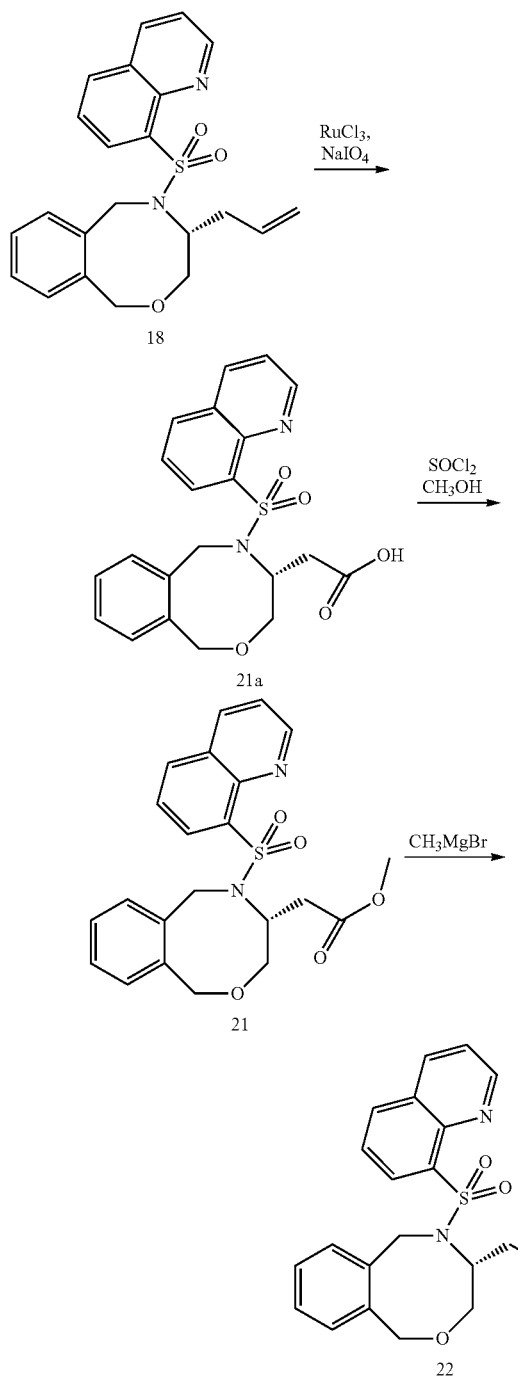

Step 1: (R)-2-(5-(Quinolin-8-ylsulfonyl)-3,4,5,6-tetrahydro-1H-benzo[f][1,4]oxazocin-4-yl)acetic acid (21a)

A solution of compound 18 (1.0 g, 2.5 mmol) and $NaIO_4$ (2.1 g, 10 mmol) in $CCl_4/CH_3CN/H_2O$ (10 mL, v/v/v=1:1:1.5) was added $RuCl_3$ (11 mg, 0.05 mmol). The resulting solution was stirred at rt for 16 hr. The reaction mixture was diluted with DCM and the aqueous layer was further extracted with DCM. The combined organic extracts were washed with brine, dried over $Na_2SO_4$ and concentrated. The crude product was purified by CC to give the compound 21a (800 mg, 77% yield) as a white solid. LCMS (m/z): 413.2 (MH+).

Step 2: (R)-Methyl 2-(5-(quinolin-8-ylsulfonyl)-3,4,5,6-tetrahydro-1H-benzo[f][1,4]oxazocin-4-yl)acetate (21)

A solution of compound 19 (200 mg, 0.48 mmol) in $SOCl_2$ (5 mL) was stirred at rt for 0.5 hr, and $CH_3OH$ (10 mL) was added after the reaction mixture was cooled to 0° C. The mixture was stirred for another 0.5 h and the solvent was removed. The residue was diluted with DCM and washed with water and brine, the organic layers were concentrated to get the desired compound 21 (160 mg, 78% yield) without purification. LCMS (m/z): 427.2 (MH+).

Step 3: (R)-2-Methyl-1-(5-(quinolin-8-ylsulfonyl)-3,4,5,6-tetrahydro-1H-benzo[f][1,4]oxazocin-4-yl)propan-2-ol (22)

Compound 21 (160 mg, 0.37 mmol) was dissolved in anhydrous THF (5 mL) and the solution was cooled in an ice-water bath. A solution of 3M methylmagnesium bromide in THF (0.25 mL, 0.74 mmol) was added dropwise via syringe and the stirred reaction mixture was allowed to warm to it and react for 2 hr. The reaction mixture was quenched with $NH_4Cl$ solution and extracted with EA. The organic extracts were dried over anhydrous $Na_2SO_4$, filtered and concentrated. The crude product was purified by Prep-TLC to give the desired compound 22 (35 mg, 22% yield). LCMS (m/z): 427.2 (MH+).

Preparative Example 23, 24 and 25

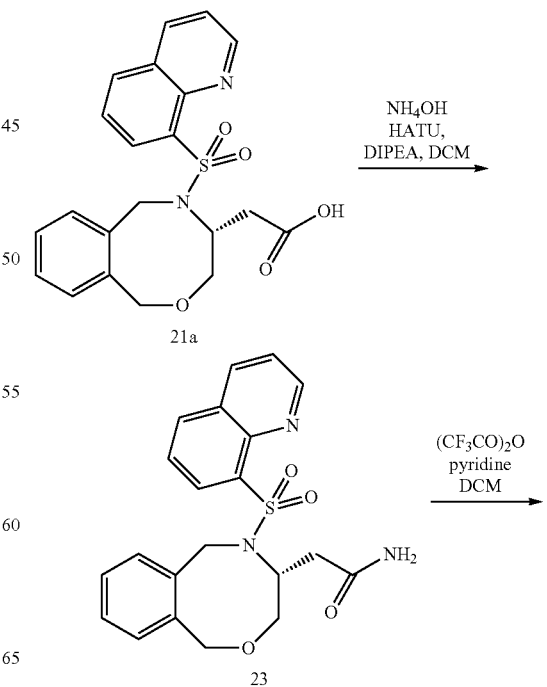

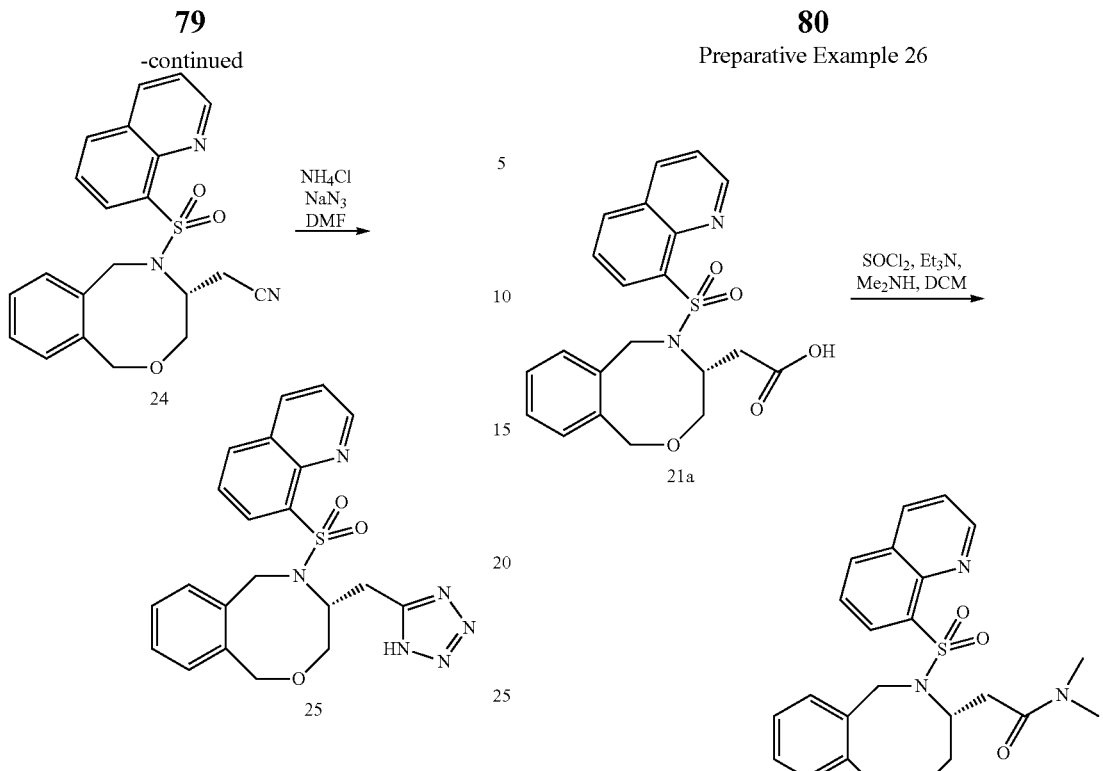

Preparative Example 26

Step 1: (R)—N,N-Dimethyl-2-(5-(quinolin-8-ylsulfonyl)-3,4,5,6-tetrahydro-1H-benzo[f][1,4]oxazocin-4-yl)acetamide (26)

A solution of compound 21a (100 mg, 0.24 mmol) in SOCl$_2$ (3 mL) was stirred at rt for 1 h and concentrated. Dimethylamine (32.8 mg, 0.4 mmol) and triethylamine (81 mg, 0.81 mmol) in DCM (5 mL) were added to the above residue. The mixture was stirred at rt for 1 h. The mixture was taken up in H$_2$O (10 mL) and extracted with DCM (30 mL). The organic layers were dried over Na$_2$SO$_4$ and concentrated. The crude product was purified Prep-TLC to give the pure compound 26 (40 mg, 38% yield). LCMS (m/z): 440.1 (MH+).

Preparative Example 27

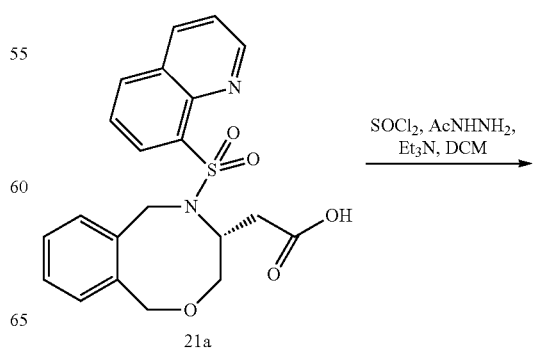

Step 1: (R)-2-(5-(Quinolin-8-ylsulfonyl)-3,4,5,6-tetrahydro-1H-benzo[f][1,4]oxazocin-4-yl)acetamide (23)

A solution of compound 21a (100 mg, 0.24 mmol), HATU (137 mg, 0.36 mmol), DIPEA (77 mg, 0.6 mmol) in DCM (5 mL) was stirred at it for 0.5 hr. Ammonium hydroxide (12 mg, 0.36 mmol) was added and the mixture was stirred at it for 2 hr. The reaction mixture was quenched with water and extracted with DCM. The organic extracts were dried over anhydrous Na$_2$SO$_4$, filtered and concentrated. The crude product was purified by Prep-TLC to give the desired compound 23 (32 mg, 32% yield). LCMS (m/z): 412.2 (MH+).

Step 2: (R)-2-(5-(Quinolin-8-ylsulfonyl)-3,4,5,6-tetrahydro-1H-benzo[f][1,4]oxazocin-4-yl)acetonitrile (24)

A solution of compound 23 (100 mg, 0.24 mmol), pyridine (47 mg, 0.6 mmol) and (CF$_3$CO)$_2$O (76 mg, 0.36 mmol) in DCM (5 mL) was stirred at it for 2 hr. The reaction mixture was quenched with water and extracted with DCM. The organic extracts were dried over anhydrous Na$_2$SO$_4$, filtered and concentrated. The crude product was purified by Prep-TLC to give the desired compound 24 (34 mg, 36% yield). LCMS (m/z): 394.2 (MH+).

Step 3: (R)-4-((1H-Tetrazol-5-yl)methyl)-5-(quinolin-8-ylsulfonyl)-3,4,5,6-tetrahydro-1H-benzo[f][1,4]oxazocine (25)

To the mixture of sodium azide (48 mg, 0.75 mmol) and ammonium chloride (40 mg, 0.75 mmol) in dry DMF (5 mL) was added compound 24 (100 mg, 0.25 mmol) under a nitrogen atmosphere. The mixture was stirred at 125° C. for 48 hr. The cooled reaction was poured into ice water and acidified to pH=1 with 1N HCl. The mixture was concentrated in vacuo and purified by Prep-HPLC to obtain compound 25 (30 mg, 27% yield). LCMS (m/z): 437.2 (MH+).

-continued

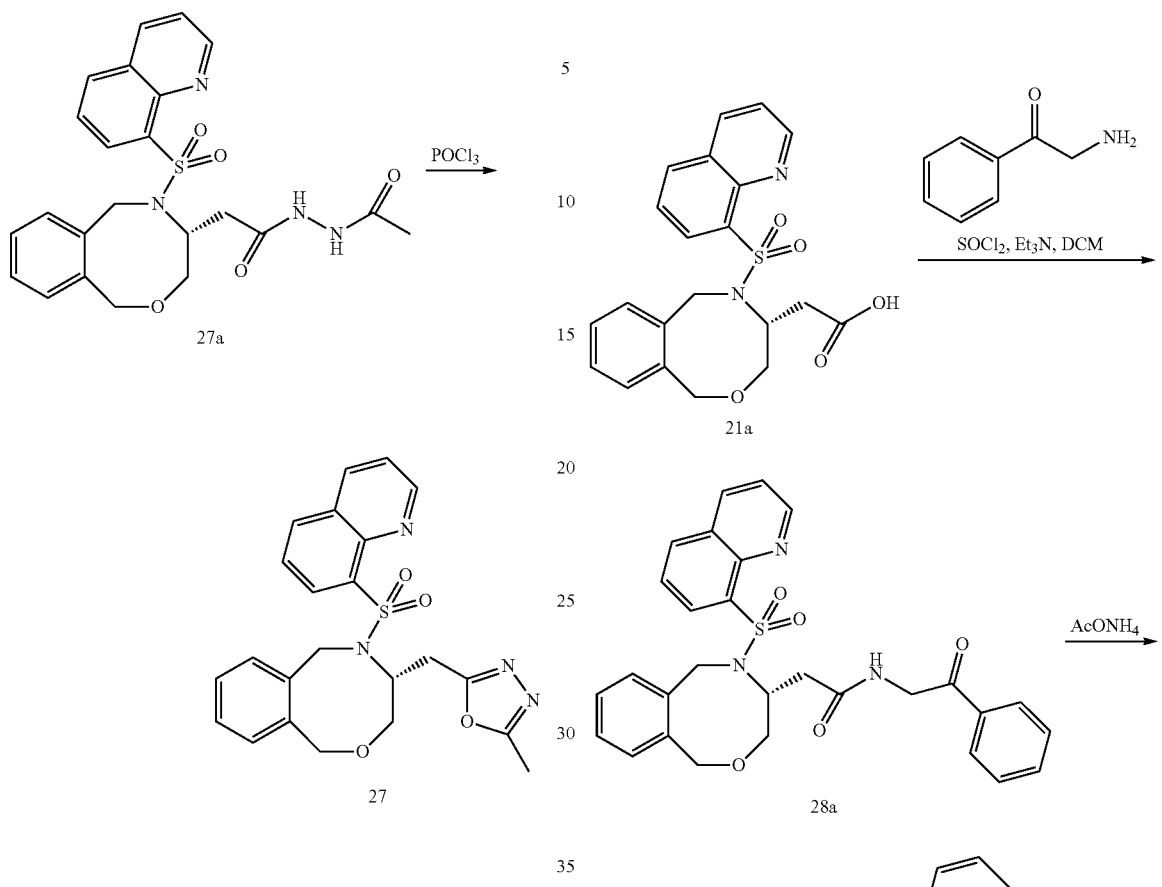

Step 1: (R)—N'-Acetyl-2-(5-(quinolin-8-ylsulfonyl)-3,4,5,6-tetrahydro-1H-benzo[f][1,4]oxazocin-4-yl)acetohydrazide (27a)

A solution of compound 21a (412 mg, 1 mmol) in SOCl₂ (3 mL) was stirred for 1 h at rt and concentrated. Acetohydrazide (148 mg, 2 mmol) and triethylamine (303 mg, 3 mmol) in DCM (5 mL) were added to the above residue. The mixture was stirred at rt for 1 h. The reaction was taken up in H₂O (10 mL) and extracted with DCM (30 mL). The combined organic layers were dried over Na₂SO₄ and concentrated. The crude product was purified by CC to give the compound 27a (400 mg, 85% yield).

Step 2: (R)-4-((5-Methyl-1,3,4-oxadiazol-2-yl)methyl)-5-(quinolin-8-ylsulfonyl)-3,4,5,6-tetrahydro-1H-benzo[f][1,4]oxazocine (27)

A mixture of compound 27a (100 mg, 0.21 mmol) and POCl₃ (3 mL) was stirred at 110° C. for 3 h. The mixture was taken up in H₂O (10 mL) and extracted with DCM (30 mL). The combined organic layers were dried over Na₂SO₄, filtered and concentrated. The crude product was purified by Prep-TLC to give the pure compound 27 (40 mg, 42% yield). LCMS (m/z): 451.1 (MH+).

Preparative Example 28

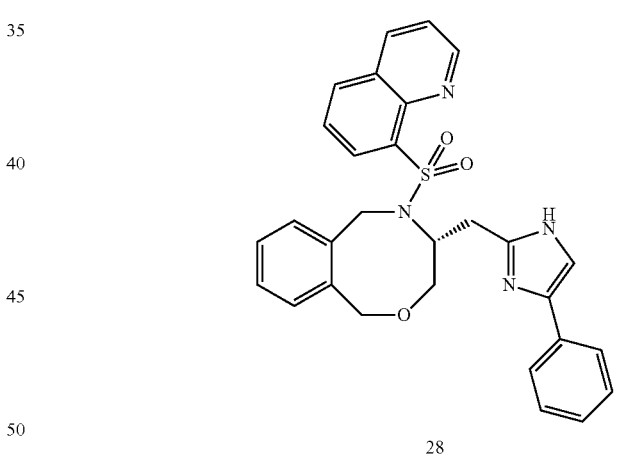

Step 1: (R)—N-(2-Oxo-2-phenylethyl)-2-(5-(quinolin-8-ylsulfonyl)-3,4,5,6-tetrahydro-1H-benzo[f][1,4]oxazocin-4-yl) acetamide (28a)

A mixture of compound 21a (412 mg, 1 mmol) and SOCl₂ (3 mL) was stirred at rt for 1 h and concentrated. 2-Amino-1-phenylethanone (342 mg, 2 mmol) and triethylamine (303 mg, 3 mmol) in DCM (5 mL) were added to the above residue. The mixture was stirred at rt for 1 h. The reaction was taken up in H₂O (10 mL) and extracted with DCM (30 mL). The combined organic layers were dried over Na₂SO₄, filtered and concentrated. The crude product was purified by CC to give compound 28a (400 mg, 75% yield).

Step 2: (R)-4-((4-Phenyl-1H-imidazol-2-yl)methyl)-5-(Quinolin-8-ylsulfonyl)-3,4,5,6-tetrahydro-1H-benzo[f][1,4]oxazocine (28)

A microwave tube was charged with compound 28a (100 mg, 0.19 mmol), AcONH$_4$ (44 mg, 0.57 mmol) and DMF (3 mL), and then was sealed and heated to 150° C. for 1 h under microwave irradiation. The mixture was taken up in H$_2$O (10 mL) and extracted with DCM (30 mL). The combined organic layers were dried over Na$_2$SO$_4$, filtered and concentrated. The crude product was purified by Prep-TLC to give compound 28 (30 mg, 30% yield). LCMS (m/z): 511.1 (MH+).

Preparative Example 29

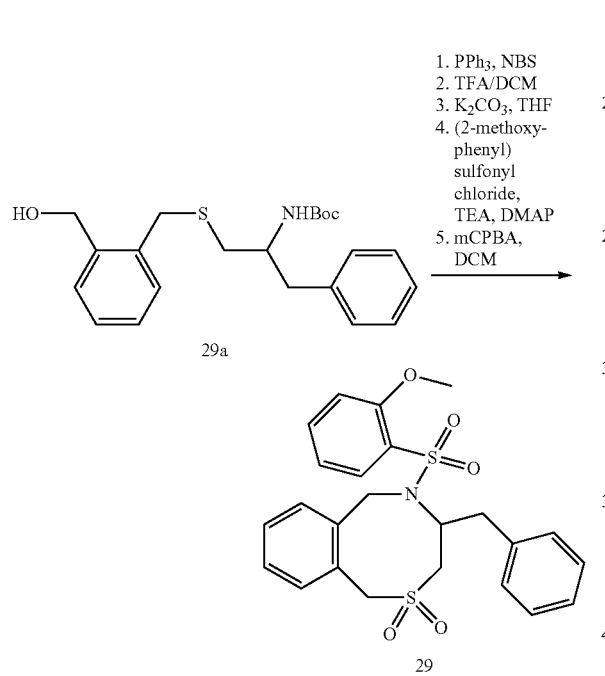

Step 1: To a solution of compound 29a (2.2 g, 6.7 mmol) in dry THF (30 mL) was added NBS (1.8 g, 10 mmol) and PPh$_3$ (2.6 g, 10 mmol) at 0° C. The mixture was stirred at 0° C. for 30 min. Then the mixture was allowed to stir at rt for 2 h. The solvent was removed under vacuum to give a white solid (2.44 g).

Step 2: To a solution of the white solid from Step 1 (2.44 g) in DCM (20 mL) was added slowly TFA (2 mL) at 0° C. The mixture was stirred at 0° C. for 2 h. The solvent was removed under vacuum to give a white solid (1.96 g).

Step 3: A mixture of the solid residue from Step 2 (1.96 g) and K$_2$CO$_3$ (1.96 g, 14.3 mmol) in dry THF (30 mL) was stirred at rt overnight. The reaction mixture was filtered and the filtrate was evaporated under vacuum to give a white solid (1.28 g).

Step 4: To a mixture of the solid residue from Step 3 (256 mg) and TEA (360 mg, 3.57 mmol) in ACN (20 mL) was added 2-methoxy-phenyl sulfonyl chloride (267 mg, 1.31 mmol) and a catalytic amount of DMAP. The reaction mixture was stirred at rt overnight. The solvent was evaporated in vacuo to give a white solid (384 mg).

Step 5: A mixture of the solid residue from Step 4 (38 mg) and mCPBA (70%, 68.8 mg, 0.28 mmol) in DCM (10 mL) was stirred at rt overnight. The solvent was evaporated in vacuo and purified by CC eluting with PE:EA=3:1 to give a white solid (40 mg). $^1$H NMR (400 MHz, DMSO-d$_6$) δ 8.03 (d, J=6.4 Hz, 1H), 7.74 (t, J=6.1 Hz, 1H), 7.45-7.42 (m, 2H), 7.26-7.24 (m, 2H), 7.23-7.18 (m, 5H), 6.85 (d, J=6.4 Hz, 2H), 5.45 (d, J=15.2 Hz, 1H), 5.35 (d, J=11.6 Hz, 1H), 4.82 (d, J=15.2 Hz, 1H), 4.42-4.32 (m, 2H), 4.03 (s, 3H), 3.47-3.37 (m, 1H), 2.89 (t, J=9.6 Hz, 1H), 2.45 (d, J=8.0 Hz, 1H), 2.22 (d, J=7.8 Hz, 1H); MS (ESI+) m/z: 472.0 [M+H]$^+$.

Preparative Example 30

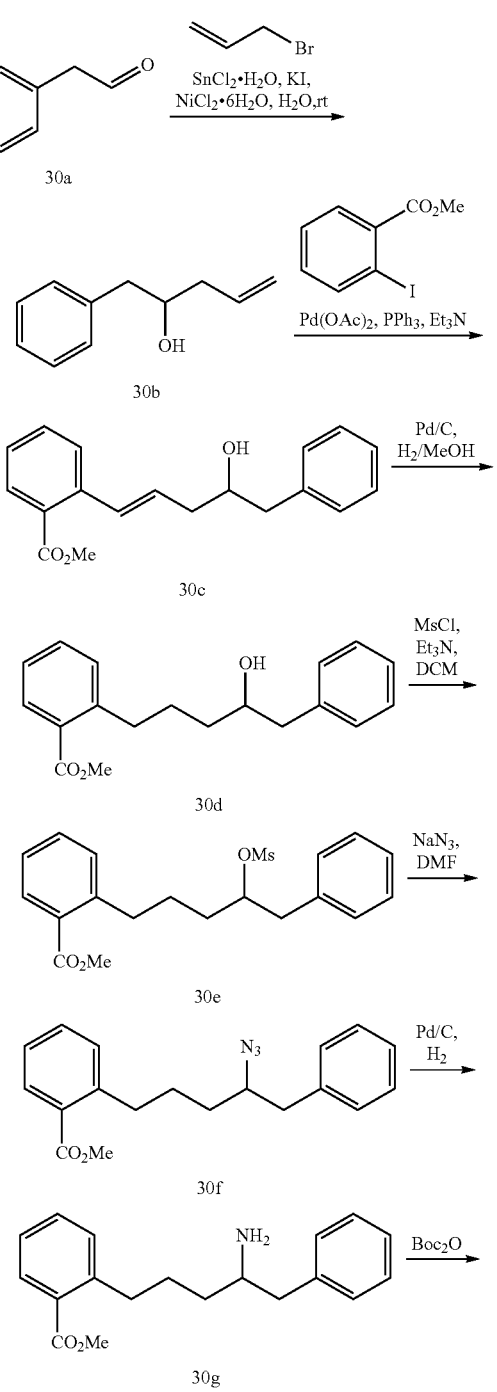

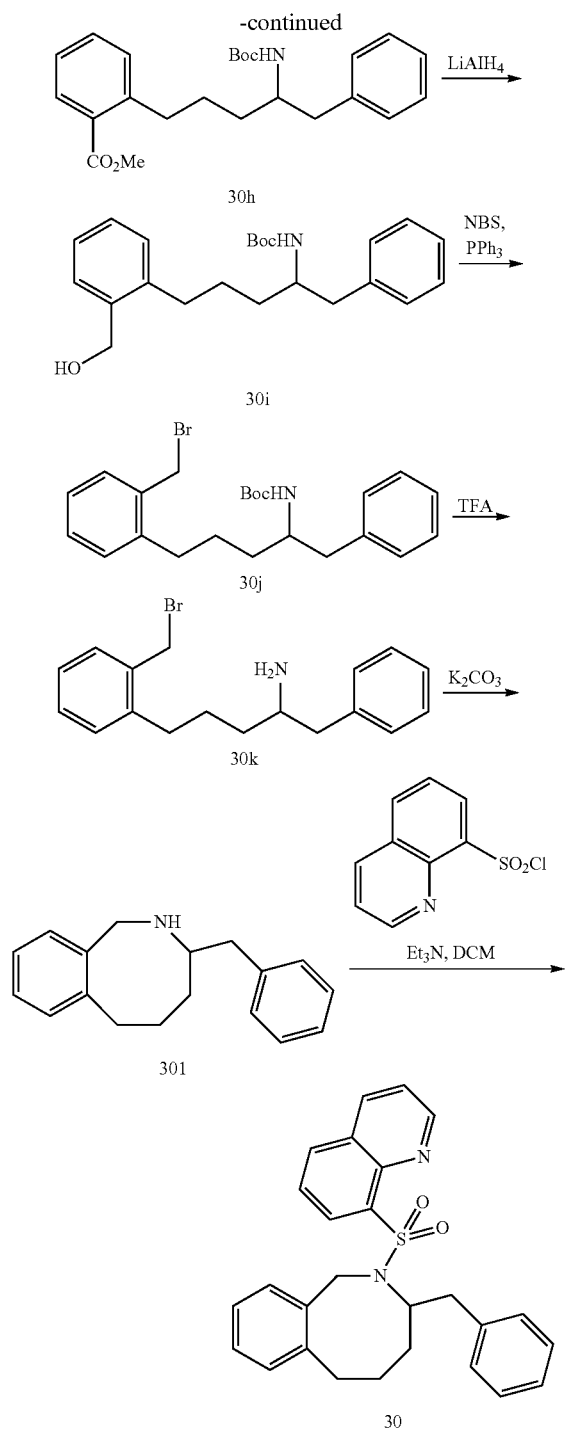

The residue was purified by CC using PE:EA=5:1 as mobile phase to give the desired product (5.75 g, 54% yield).

Step 2: (E)-Methyl 2-(4-hydroxy-5-phenylpent-1-en-1-yl)benzoate (30c)

A mixture of triethylamine (7.6 mL, 54.7 mmol), triphenylphosphine (0.778 g, 2.97 mmol) and palladium acetate (0.35 g, 1.56 mmol) in 1,4-dioxane (50 mL) was refluxed to form a homogeneous dark-red solution. The reaction temperature was then reduced to just below reflux. Compound 30b (4.56 g, 28 mmol), methyl 2-iodobenzoate (4.10 g, 15.6 mmol) and triethylamine (2.88 mL, 10.2 mmol) were added subsequently with stirring. The reaction mixture was then refluxed for about 30 min until TLC showed the SM had disappeared. The reaction mixture was filtered hot through celite, which was washed with 1,4-dioxane. The combined filtrate and washings were evaporated in vacuo to a small volume and purified by CC using PE:EA=5:1 as mobile phase to give the desired product (2.59 g, 56% yield).

Step 3: Methyl 2-(4-hydroxy-5-phenylpentyl)benzoate (30d)

A solution of 30c (2.59 g, 8.75 mmol) in MeOH (100 mL) was hydrogenated using 10% Pd/C (0.93 g, 0.88 mmol) as catalyst at atmospheric pressure overnight. The catalyst was removed by filtration, and the solution was evaporated at reduced pressure to afford the desired product (2.27 g, 97% yield).

Step 4: Methyl 2-(4-((methylsulfonyl)oxy)-5-phenylpentyl)benzoate (30e)

To a solution of 30d (2.27 g, 7.62 mmol) and Et$_3$N (2.12 mL, 15.2 mmol), MsCl (1.2 mL, 15.2 mmol) was added dropwise at 0° C. After addition was complete, the reaction was stirred at rt until LC-MS analysis indicated the total consumption of the SM. The solvent was removed and the residue was purified by CC using PE:EA=5:1 as mobile phase to afford the desired product (2.9 g, quant.)

Step 5: Methyl 2-(4-azido-5-phenylpentyl)benzoate (30f)

Sodium azide (1 g, 15.4 mmol) and 15-crown-5 (0.17 g, 0.77 mmol) were added to a stirred solution of 30e (2.9 g, 7.7 mmol) in DMF (60 mL). The mixture was heated at 85° C. for 24 h under argon atmosphere. Then DCM (300 mL) was added, the solution was washed with a saturated NaHCO$_3$ solution (2×150 mL) and brine (3×200 mL), and dried over Na$_2$SO$_4$. After removal of the solvent under reduced pressure, the desired product was obtained as yellow oil, which was used without further purification in the next step.

Step 6: Methyl 2-(4-amino-5-phenylpentyl)benzoate (30g)

A solution of 30f (crude 7.7 mmol) in MeOH (40 mL) was hydrogenated using 10% Pd/C (817 mg, 0.77 mmol) as catalyst at atmospheric pressure overnight. The catalyst was removed by filtration, and the solution was evaporated at reduced pressure to afford the crude desired product as yellow oil, which was used without further purification in the next step.

Step 1: 1-Phenylpent-4-en-2-ol (30b)

To a mixture of phenylacetaldehyde 30a (7.84 g, 65.3 mmol) and 3-bromoprop-1-ene (11.1 g, 91.5 mmol) in water (50 mL), KI (3.25 g, 19.6 mmol) and NiCl$_2$.6H$_2$O (3.1 g, 13 mmol) were added. After the mixture was stirred for several minutes, SnCl$_2$.H$_2$O (29.5 g, 13 mmol) was added. The mixture was vigorously stirred at rt overnight and then extracted with EA. The combined organic layer was washed by brine, dried over anhydrous sodium sulfate, evaporated in vacuo.

Step 7: Methyl 2-(4-((tert-butoxycarbonyl)amino)-5-phenylpentyl)benzoate (30h)

To a solution of 30g (2.42 g 8.17 mmol) and Et₃N (2.27 mL, 16.4 mmol) in DCM (60 mL), (Boc)₂O (3.56 g, 16.4 mmol) was added dropwise at 0° C. The mixture was stirred at rt until TLC analysis indicated the total consumption of the SM. The solvent was removed and the residue was purified by CC using PE:EA=5:1 as mobile phase to afford the desired product (2.2 g, 68% yield over three steps).

Step 8: tert-Butyl(5-(2-(hydroxymethyl)phenyl)-1-phenylpentan-2-yl)carbamate (30i)

30h (1.8 g, 4.55 mmol) in THF (5 mL) was added dropwise to a stirred solution of LiAlH₄ (0.35 g, 9.1 mmol) in THF (25 mL) at 0° C. Then the mixture was stirred at rt until TLC analysis indicated the total consumption of the SM. The reaction was quenched carefully by the slow addition of water (10 mL), and then the liquid was decanted away from the precipitate. The precipitate was washed with DCM (3×50 mL) and the organic layers were combined and dried over Na₂SO₄. The solvent was removed and the residue was purified by CC using PE:EA=5:1 as mobile phase to afford the desired product (1.3 g, 79% yield).

Step 9: tert-Butyl(5-(2-(bromomethyl)phenyl)-1-phenylpentan-2-yl)carbamate (30j)

To a mixture of NBS (550 mg, 3.65 mmol) and PPh₃ (978 mg, 3.65 mmol) in DCM (25 mL), the solution of 30I (900 mg, 2.44 mmol) in DCM (15 mL) was added at rt. The mixture was stirred at rt until TLC analysis indicated the total consumption of the SM. The solvent was evaporated and the residue was purified by CC using PE:EA=6:1 as mobile phase to afford the desired product (680 mg, 65% yield).

Step 10: 5-(2-(Bromomethyl)phenyl)-1-phenylpentan-2-amine (30k)

To a solution of 30j (680 mg, 1.58 mmol) in DCM (20 mL) was added CF₃COOH (1.79 g, 15.8 mmol). The solution was left to stir at rt until TLC analysis indicated the total consumption of the SM. Then the solvent was removed to get the crude desired product as yellow oil, which was used without further purification in the next step.

Step 11: 3-Benzyl-1,2,3,4,5,6-hexahydrobenzo[c]azocine (30l)

To a solution of 30k (crude 1.58 mmol) in THF (10 mL) was added K₂CO₃ (436 mg, 3.16 mmol). The mixture was left to stir at rt until LC-MS analysis indicated the total consumption of the SM. Then the solid was removed by filtration and the solution was concentrated under reduced pressure to obtain the crude desired product. It was used without further purification in the next step.

Step 12: 3-Benzyl-2-(quinolin-8-ylsulfonyl)-1,2,3,4,5,6-hexahydrobenzo[c]azocine (30)

To a solution of 30l (crude 1.58 mmol), Et₃N (0.33 mL, 2.4 mmol) and DMAP (39 mg, 0.32 mmol) in DCM (25 mL), quinoline-8-sulfonyl chloride (538 mg, 2.37 mmol) in DCM (5 mL) was added dropwise at 0° C. After addition was complete, the solution was left to stir at rt overnight. The mixture was washed with water (2×30 mL) and brine. The organic layer was combined, dried over Na₂SO₄, concentrated in vacuo. MeOH (10 mL) was added to the residue and the precipitation was filtered to give the desired product (60 mg, 81% over three steps). ¹H NMR (500 MHz, CDCl₃) δ: 9.07 (m, 1H), 8.51 (d, 1H), 8.13 (d, 1H), 7.93 (d, 1H), 7.57 (t, 1H), 7.44 (m, 1H), 7.29 (d, 1H), 7.12 (m, 2H), 6.98 (m, 1H), 6.90 (m, 3H), 6.59 (d, 2H), 5.76 (d, 1H), 5.53 (d, 1H), 4.34 (m, 1H), 3.61 (m, 1H), 2.59 (m, 1H), 2.27 (t, 1H), 2.07 (m, 1H), 1.88 (m, 1H), 1.60 (m, 1H), 1.34 (m, 1H), 1.24 (m, 1H). MS (ESI+) m/z: 443 [M+H]⁺.

Preparative Example 31

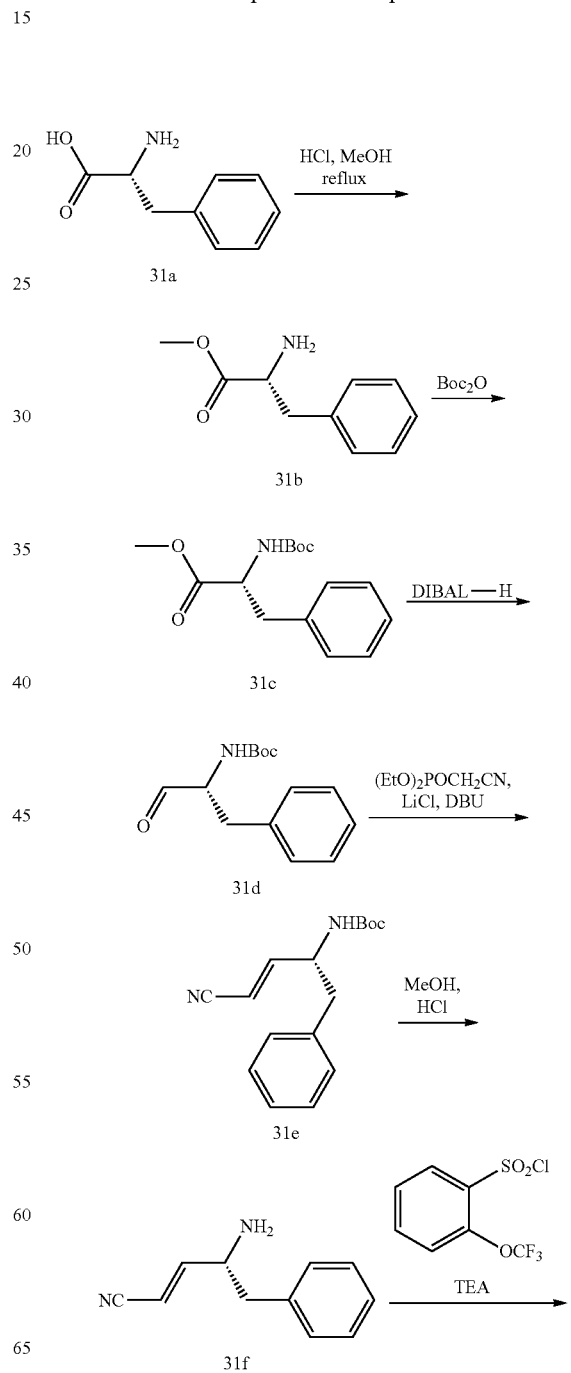

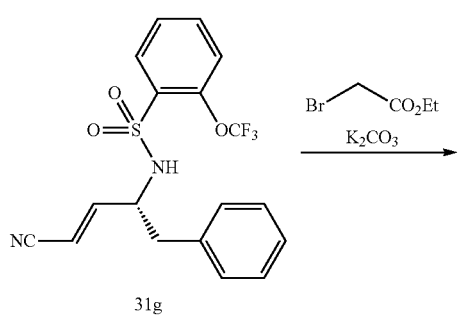
31g
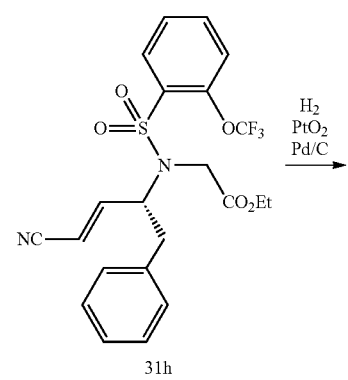
31h
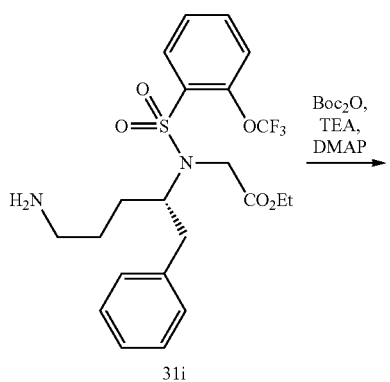
31i
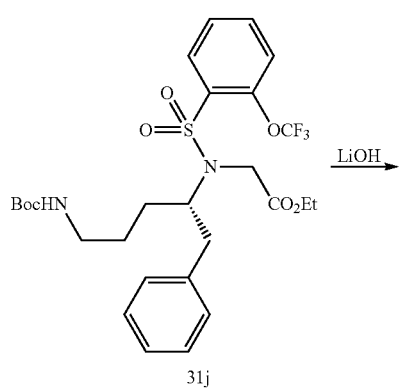
31j
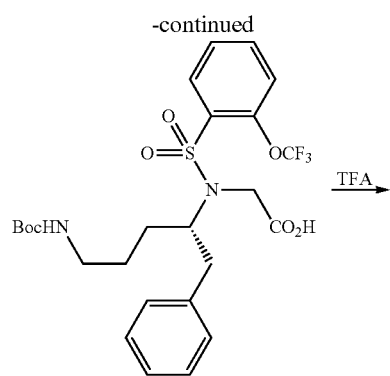
31k
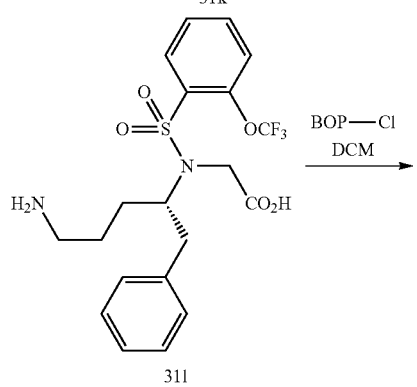
31l
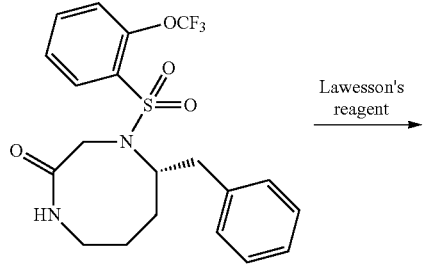
31m
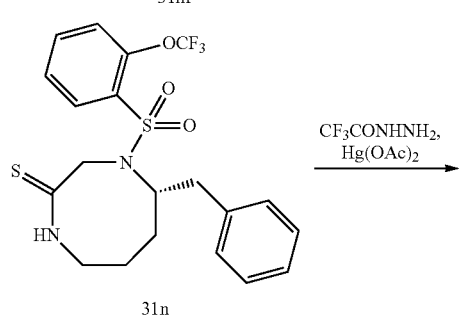
31n
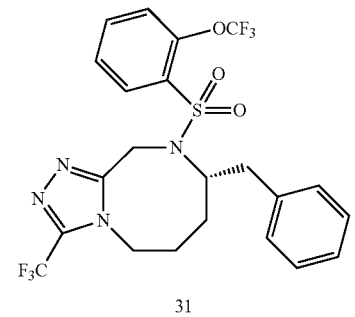
31

Step 1: (R)-Methyl 2-amino-3-phenylpropanoate (31b)

A mixture of compound 31a and 2M HCl/MeOH was refluxed for 4 h. The mixture was cooled to rt and concentrated in vacuo to obtain compound 31b.

Step 2: (R)-Methyl 2-((tert-butoxycarbonyl)amino)-3-phenylpropanoate (31c)

Saturated NaHCO$_3$ aqueous solution (125 mL) was added to a solution of compound 31b (50 g, 0.279 mol) and (Boc)$_2$O (133 g, 0.418 mol) in DCM and the resulting mixture was stirred at rt for 3 h. The reaction was complete as indicated by TLC. The organic layer was separated and the aqueous layer was extracted with DCM. The combined organic layers were dried (Na$_2$SO$_4$), concentrated and the residue was purified by CC (hexane/EA=6:1) to give compound 31c as a white solid (74 g, 95% yield).

Step 3: (R)-tert-Butyl(1-oxo-3-phenylpropan-2-yl)carbamate (31d)

To a stirred solution of compound 31c (25.0 g, 90 mmol) in toluene-DCM (4:1, 1000 mL) was added dropwise a solution of DIBAL-H in toluene (1.0 M, 179 mL, 179 mmol) at −78° C. under argon and the mixture was stirred for 1 h at this temperature. Methanol (200 mL) was added immediately to quench the reaction. The reaction mixture was poured into a solution of 200 mL of 20% sodium potassium tartrate (Rochelle salt) and stirred at rt until the two layers separated. The organic layer was concentrated in vacuo and the residue was purified by CC (hexane/EA=2:1) to give compound 31d as a white solid (19.9 g, 89% yield).

Step 4: (R,E)-tert-Butyl(4-cyano-1-phenylbut-3-en-2-yl)carbamate (31e)

To a stirred suspension of LiCl (1.0 g, 24 mmol) in dry ACN (200 mL) under nitrogen at rt, was added (EtO)$_2$POCH$_2$CN (4.2 g, 24 mmol), DBU (3.0 g, 20 mmol) and compound 31d (5.0 g, 20 mmol). Almost all of the salt soon dissolved and the reaction completed in 1.5 h. The reaction was quenched with citric acid, and the mixture was extracted with EA three times. The combined organic layers were washed with brine and dried over anhydrous Na$_2$SO$_4$. After filtration, the filtrate was evaporated and the residue was purified by CC (hexane/EAc=5:1) to give compound 31e (4.2 g, 77% yield).

Step 5: (R,E)-4-Amino-5-phenylpent-2-enenitrile (31f)

Compound 31e (4.0 g, 14.7 mmol) was treated with 2M HCl/MeOH (300 mL). After the reaction was over, the solvents were removed under reduced pressure to give a white solid. The product was directly used in the next reaction step without further purification.

Step 6: (R,E)-N-(4-Cyano-1-phenylbut-3-en-2-yl)-2-(trifluoromethoxy)benzenesulfonamide (31g)

To a solution of compound 31f (2.5 g, 14.5 mmol) in DCM (100 mL) was added 2-(trifluoromethoxy)benzene-1-sulfonyl chloride (4.2 g, 16.0 mmol) and TEA (4.4 g, 3.5 mmol). The mixture was stirred at rt for 12 h, then DCM (50 mL) and 2N HCl (20 mL) were added to the mixture. The organic layer was separated and washed with brine and dried over anhydrous Na$_2$SO$_4$. After filtration, the filtrate was evaporated and the residue was purified by CC (hexane/EA=5:1) to give compound 31g (4.2 g, 74% yield).

Step 7: (R,E)-Ethyl 2-(N-(4-cyano-1-phenylbut-3-en-2-yl)-2-(trifluoromethoxy)phenylsulfonamido)acetate (31h)

To a solution of compound 31g (4.2 g, 10.6 mmol) in DMF (100 mL) was added ethyl bromoacetate (2.1 g, 12.7 mmol) and K$_2$CO$_3$ (3.5 g, 25.4 mmol). The mixture was stirred at rt for 12 h, then water (100 mL) was added to the mixture. The mixture was extracted with EA three times and the combined organic layer was washed with brine and dried over anhydrous Na$_2$SO$_4$. After filtration, the filtrate was evaporated and the residue was purified by CC (hexane/EA=5:1) to give compound 31h (3.7 g, 73% yield).

Step 8: (S)-Ethyl 2-(N-(5-amino-1-phenylpentan-2-yl)-2-(trifluoromethoxy)phenylsulfonamido)acetate (31i)

To a solution of compound 31h (3.7 g, 7.7 mmol) in MeOH (200 mL) were added PtO$_2$ (0.1 g), Pt/C (0.3 g) and TFA (1.9 g). The mixture was hydrogenated in a Parr shaker at 48 psi for 12 h. The mixture was filtered and concentrated. The product was directly used in the next reaction step without further purification.

Step 9: (S)-Ethyl 2-(N-(5-((tert-butoxycarbonyl)amino)-1-phenylpentan-2-yl)-2-(trifluoromethoxy)phenylsulfonamido)acetate (31j)

To an ice-cooled solution of compound 31i (3.4 g, 7.0 mmol) in DCM (150 mL), TEA (2.1 g, 21.0 mmol) and DMAP (50 mg) were added, followed by the dropwise addition of a solution of di-tert-butyl dicarbonate (1.7 g, 7.7 mmol) in DCM (50 mL). The reaction mixture was stirred for 12 h at rt. The solvent was evaporated and the crude product was dissolved in EA. The organic layer was washed with water, 10% citric acid and brine, dried over anhydrous Na$_2$SO$_4$ and concentrated in vacuo. The resulting crude product was purified by CC (hexane/EA=4:1) to give compound 31j (3.3 g, 80% yield over two steps).

Step 10: (S)-2-(N-(5-((tert-Butoxycarbonyl)amino)-1-phenylpentan-2-yl)-2-(trifluoromethoxy)phenylsulfonamido)acetic acid (31k)

To a solution of compound 31j (3.3 g, 5.6 mmol) in MeOH/THF (1:1, 100 mL) was added LiOH (2N, 30 mL). The mixture was stirred at rt for 2 h. After the reaction was over, 2N HCl (30 mL) was added. The mixture was extracted with EA three times and the combined organic layer was washed with brine and dried over anhydrous Na$_2$SO$_4$. After filtration, the filtrate was evaporated and the residue was purified by CC (hexane/EA=1:1) to give compound 31k (2.8 g, 90% yield).

Step 11: (S)-2-(N-(5-Amino-1-phenylpentan-2-yl)-2-(trifluoromethoxy)phenylsulfonamido)acetic acid (31l)

To a solution of compound 31k (2.8 g, 5 mmol) in DCM (100 mL) was added TFA (20 mL). After the reaction was over, the solvents were removed by reduced pressure to give a white solid. The product was used in the next reaction step without further purification.

Step 12: (S)-5-Benzyl-4-((2-(trifluoromethoxy)phenyl)sulfonyl)-1,4-diazocan-2-one (31m)

To a solution of compound 31l (2.3 g, 5.0 mmol) in DCM (50 mL) was added DIPEA (2.6 g, 20 mmol) and BOP-Cl (1.5 g, 6.0 mmol). The reaction mixture was stirred at rt for 5 h under nitrogen, then 50 mL DCM and 10% citric acid were added to the mixture. The organic layer was separated, washed with brine and dried over anhydrous $Na_2SO_4$. After filtration, the filtrate was evaporated and the residue was purified by CC (hexane/EA=3:1) to give compound 31m (1.9 g, 88% yield).

Step 13: (S)-5-Benzyl-4-((2-(trifluoromethoxy)phenyl)sulfonyl)-1,4-diazocane-2-thione (31n)

A solution of compound 31m (500 mg, 1.13 mmol) in toluene (30 mL) was treated with 2,4-bis(4-methoxyphenyl)-1,3,2,4-dithiadiphosphetane 2,4-disulfide (Lawesson's reagent) (457 mg, 1.13 mmol), heated at 80° C. for 30 min, cooled to rt, treated with $NaHCO_3$ (95 mg, 1.13 mmol) and stirred for 10 min. The mixture was extracted with EA three times and the combined organic layer was washed with brine and dried over anhydrous $Na_2SO_4$. After filtration, the filtrate was evaporated and the residue was purified by CC (hexane/EA=4:1) to give compound 31n (491 mg, 95% yield).

Step 14: (S)-8-Benzyl-9-((2-(trifluoromethoxy)phenyl)sulfonyl)-3-(trifluoromethyl)-5,6,7,8,9,10-hexahydro-[1,2,4]triazolo[4,3-a][1,4]diazocine (31)

A solution of compound 31n (150 mg, 0.33 mmol) in THF (15 mL) was cooled to 0° C., treated with $Hg(OAc)_2$ (118 mg, 0.36 mmol) and $CF_3CONHNH_2$ (173 mg, 1.65 mmol), stirred for 2 h, diluted with $Et_2O$ (20 mL), filtered through Celite and evaporated. A solution of the residue in toluene/$H_2O$ (30:1, 15 mL) was treated with $TsOH.H_2O$ (250 mg, 1.32 mmol) and stirred at 75° C. for 12 h. The mixture was diluted with EA (30 mL) and washed with saturated $K_2CO_3$. The aqueous layer was extracted with EA (20 mL). The combined organic layers were dried over $Na_2SO_4$. After filtration, the filtrate was evaporated and the residue was purified by Preparative HPLC to give compound 31 as a white solid (113 mg, 64% yield). $^1H$ NMR (500 MHz, $CDCl_3$) δ 8.14 (d, J=7.5 Hz, 1H), 7.68 (t, J=8.5 Hz, 1H), 7.50 (t, J=7.5 Hz, 1H), 7.40 (d, J=8.5 Hz, 1H), 7.15-7.10 (m, 3H), 6.76-6.70 (m, 2H), 5.71 (d, J=18.0 Hz, 1H), 4.97 (m, 1H), 4.90 (d, J=8.0 Hz, 1H), 4.26 (dd, J=15.0, 8.0 Hz, 1H) 4.21 (m, 1H), 2.59 (dd, J=13.0, 10.5 Hz, 1H), 2.33 (dd, J=13.0, 5.0 Hz, 1H), 2.12-1.90 (m, 2H), 1.70-1.60 (m, 2H). MS (ESI+) m/z: 535 [M+H]$^+$.

Preparative Examples 31/1 to 31/2

Following similar procedures as described in the Preparative Example 31, Step 14 the following compounds were prepared.

| # | Structure | MW | Measured m/z |
|---|-----------|------|--------------|
| 31/1 | 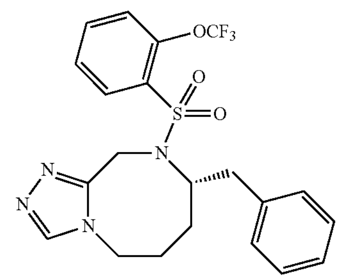 [SMILES: O=S(=O)(c1ccccc1OC(F)(F)F)N1Cc2nncn2CCC[C@H]1Cc1ccccc1] | 466.5 | 467.1 |
| 31/2 | 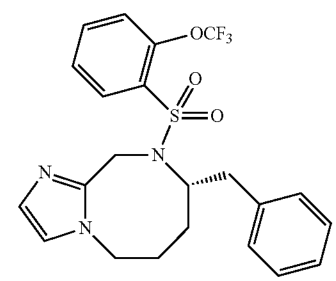 [SMILES: O=S(=O)(c1ccccc1OC(F)(F)F)N1Cc2nccn2CCC[C@H]1Cc1ccccc1] | 465.5 | 466.1 |

Protein Expression and Purification

Protein expression and purification was done as described in WO2010/049144.

TR-FRET Activity Assay

This method measures the ability of putative ligands to modulate the interaction between the purified bacterial expressed RORγ ligand binding domain (LBD) and synthetic N-terminally biotinylated peptides which are derived from nuclear receptor coactivator proteins such as but not limited to SRC1 (NcoA1), SRC2 (NcoA2, TIF2), SRC3 (NcoA3), PGC1α, PGC1β, CBP, GRIP1, TRAP220, RIP140. The peptides used are listed in Table 1 below:

TABLE 1

| Peptide Name (aa range) | DB entry Protein | DB entry DNA | Sequence |
|---|---|---|---|
| SRC1(676-700) | NP_003734 | NM_003743.4 | NH2-CPSSHSSLTERHKILHRLLQEGSPS-COOH |
| TRAP220(631-655) | NP_004765 | NM_004774.3 | NH2-PVSSMAGNTKNHPMLMNLLKDNPAQ-COOH |
| TIF2(628-651) | NP_006531 | NM_006540.2 | NH2-GQSRLHDSKGQTKLLQLLTTKSDQ-COOH |

The ligand-binding domain (LBD) of RORγ was expressed as fusion protein with GST in BL-21 (BL3) cells using the vector pDEST15. Cells were lysed by lysozyme-treatment and sonication, and the fusion proteins purified over glutathione sepharose (Pharmacia) according to the manufacturers instructions. For screening of compounds for their influence on the RORγ-peptide interaction, the LANCE technology (Perkin Elmer) was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection assays were done in a final volume of 25 µL in a 384 well plate, in a Tris-based buffer system (20 mM Tris-HCl pH6.8; 60 mM KCl, 1 mM DTT; 5 mM MgCl$_2$; 35 ng/µL BSA), containing 20-60 ng/well recombinantly expressed RORγ-LBD fused to GST, 200-600 nM N-terminally biotinylated peptide, 200 ng/well Streptavidin-xlAPC conjugate (Prozyme) and 6-10 ng/well Eu W1024—antiGST (Perkin Elmer). DMSO content of the samples was kept at 1%.

After generation of the Tris-based buffer system, the potentially RORγ modulating ligands were diluted. After his step, protein, peptide and fluorescent acceptor and donor solutions were mixed in the Tris-based buffer system and have been added to the compound dilutions, after this addition of 'detection mix', the assay was equilibrated for one hour in the dark at rt in FIA-plates black 384 well (Corning). The LANCE signal was detected by a Perkin Elmer EnVision™ Multilabel Counter. The results were visualized by plotting the ratio between the emitted light at 665 nm and 615 nm. A basal level of RORγ-peptide formation is observed in the absence of added ligand. Ligands that promote the complex formation induce a concentration-dependent increase in time-resolved fluorescent signal. Compounds which bind equally well to both monomeric RORγ and to the RORγ-peptide complex would be expected to give no change in signal, whereas ligands, which bind preferentially to the monomeric receptor would be expected to induce a concentration-dependent decrease in the observed signal.

To assess the antagonistic potential of the compounds, IC$_{50}$ values were determined using a Ligand Sensing Assay based on Time-resolved Fluorescence Energy Transfer (TR-FRET) as described above. The normalised TR-FRET assay values, using the following equation: 1000*665 nm measurement value/615 nm measurement value, were transferred to the program GraphPad Prism to generate graphs and dose response curves using the following equation:

Equation: Sigmoidal dose-response (variable slope)

$$Y=Bottom+(Top-Bottom)/(1+10\char`\^((Log\ EC50-X)*HillSlope))$$

X is the logarithm of the concentration. Y is the response. Y starts at Bottom and goes to Top with a sigmoidal shape.

This is identical to the "four parameter logistic equation". The IC$_{50}$ values are calculated using this equation. Preparative examples listed below do reduce the signal in the TR-FRET assay in a dose dependent manner. The Preparative Examples of the present invention usually have an inhibition activity (IC$_{50}$ FRET) ranging from below 100 nM to about 10 µM, and, typically, from about 100 nM to about 1 µM. The RORγ modulating compounds of the invention desirably have an inhibition in the TR-FRET Activity Assay ranging from below 100 nM to about 1 µM. Table 2 lists typical examples of compounds of the invention that have an RORγ activity in the TR-FRET Activity Assay lower than 500 nM (Group A), from about 500 nM to 2 µM (Group B) and above 2 µM (Group C).

TABLE 2

| Group | Preparative Example # |
|---|---|
| A | 1, 1/2, 1/3, 1/5, 1/6, 1/8, 1/9, 1/10, 1/12, 1/14, 1/18, 1/19, 1/22, 1/24, 1/38, 1/40, 1/43, 1/44, 3/2, 5/3, 6, 6/2, 14, 17/4, 20 |
| B | 1/11, 1/13, 1/17, 1/20, 1/23, 1/25, 1/28, 1/36, 1/37, 1/39, 1/41, 2, 4, 6/3, 6/5, 7, 16/1, 16/3, 16/4, 18, 30, 31/1, 31/2 |
| C | 1/2, 1/27, 1/29, 1/30, 1/31, 1/32, 1/33, 1/34, 1/35, 3, 3/1, 5/1, 5/2, 5/4, 5/5, 5/6, 6/1, 6/4, 9, 11, 12, 13, 16, 16/2, 17, 17/2, 22, 26, 27, 29, 31 |

RORγ Gal4 Reporter Gene Assay

Determination of a ligand mediated Gal4 promoter driven transactivation to quantify ligand binding to RORγ was performed as follows: DNA encoding three different RORγ protein fragments was cloned into vector pCMV-BD (Stratagene). Expression was under control of a CMV promoter and as fusion to the DNA-binding domain of the yeast protein GAL4. The amino acid boundaries of the three proteins and the respective database entries are listed in Table 3. Other vectors used were pFR-Luc (Stratagene) as regulated reporter plasmid. pFR-Luc contains a synthetic promoter with five tandem repeats of the yeast GAL4 binding sites that control expression of the *Photinus pyralis* (American firefly) luciferase gene. In order to improve experimental accuracy the plasmid pRL-CMV was cotransfected. pRL-CMV contains the constitutive CMV promoter, controlling the expression of the *Renilla reniformis* luciferase.

TABLE 3

| construct name | aa borders (RefSeq) | Ref sequence ID |
|---|---|---|
| hRORg-LBD | aa259-518 | NP_005051.2 |
| hRORgt | aa1-497 | NP_001001523 (RORg, t isoform, 497aa) |
| mRORg-LBD | aa264-516 | NP_035411 |

All Gal4 reporter gene assays were done in 293T cells (DSMZ (German Collection of Microorganisms and Cell Cultures), Braunschweig, Germany, ACC635) grown in Minimum Essential Medium (MEM) with Phenol Red. The medium is supplemented with 10% fetal bovine serum, 0.1 mM nonessential amino acids, 1 mM sodium pyruvate, 1% Glutamax and 100 units Penicillin/Streptavidin per mL at 37° C. in 5% CO$_2$.

For the assay, 5×10$^5$ cells were plated per well in 96 well plates in 100 µL per well, incubated over night at 37° C. in 5% CO$_2$. The following day, medium was discarded and the cells were transiently transfected using 20 µL per well of a Opti-MEM-PEI-based transfection-reagent (Sigma-Aldrich, 408727) including the three plasmids described above. About 4 h after addition of the transfection solution, fresh Minimal Essential Medium (MEM, same composition as used for plating cells, but without serum) was added. Then compound stocks, prediluted in MEM (same composition as used for plating cells) were added (final vehicle concentration not exceeding 0.1%).

Cells were incubated for additional 16 h before firefly (FF) and *renilla* (REN) luciferase activities were measured sequentially in the same cell extract using a Dual-Light-Luciferase-Assay system (Dyer et al., Anal. Biochem. 2000, 282:158). All experiments were done in triplicates.

Applying the Gal4 reporter gene assay as described above, the Preparative Examples of the present invention usually have an inhibition activity (IC$_{50}$ FF resp. IC$_{50}$ RENnorm) ranging from below 100 nM to about 10 µM, and typically, from about 100 nM to about 1 µM. The RORγ modulating compounds of the invention desirably have an inhibition in the Gal4 reporter gene assay ranging from below 100 nM to about 1 NM. Table 4 and 5 list typical examples of compounds of the invention that have an RORγ activity in the Gal4 reporter gene assay lower than 500 nM (Group A), from about 500 nM to 2 µM (Group B) and above 2 µM (Group C) for firefly (FF, Table 4) and *renilla* normalised (RENnorm, Table 5) luciferase measurements.

TABLE 4

| Group | Preparative Example # |
|---|---|
| A | 1, 1/2, 1/3, 1/4, 1/5, 1/6, 1/9, 1/10, 1/12, 1/14, 1/15, 1/18, 1/22, 1/37, 1/38, 1/44, 3/2, 5/2, 5/3, 6/2, 14, 16/3, 16/4, |
| B | 1/7, 1/13, 1/16, 1/17, 1/19, 1/20, 1/24, 1/26, 1/28, 1/29, 1/31, 1/34, 1/36, 1/39, 1/40, 1/43, 2, 3/1, 6, 6/3, 6/5, 16/1, 16/2, 17/2, 17/4, 17/5, 18, 20, 28, 30, 31/2 |
| C | 1/11, 1/21, 1/23, 1/25, 1/30, 1/35, 4, 5/6, 11, 12, 13, 17/1, 17/3, 23, 25, 31/1 |

TABLE 5

| Group | Preparative Example # |
|---|---|
| A | 1, 1/2, 1/3, 1/4, 1/5, 1/6, 1/9, 1/10, 1/12, 1/14, 1/18, 1/22, 1/38, 1/39, 1/44, 3/2, 5/3, 6/2, 14, 16/1, 16/3, 16/4, 18 |
| B | 1/7, 1/15, 1/16, 1/17, 1/19, 1/20, 1/21, 1/24, 1/25, 1/26, 1/28, 1/29, 1/31, 1/34, 1/36, 1/37, 1/40, 1/43, 2, 3/1, 5/2, 6, 6/3, 6/5, 16/2, 17/2, 17/4, 17/5, 20, 30, 31/2 |
| C | 1/11, 1/13, 1/23, 1/35, 4, 11, 12, 13, 17/1, 17/3, 22, 23, 24, 25, 28, 31/1 |

Peripheral Blood Mononuclear Cells (PBMCs) Stimulation and Cytokine Release Assays Cryopreserved human PBMCs were purchased from Cellular Technology Ltd. thawed and counted as outlined in the supplier's protocol using CTL-anti-Aggregate-Wash-Supplement. Cells were washed and plated in CTL's serum free medium to ~$10^5$ cells/well in anti-human CD3 coated 96 well T-cell activation plates (BD; Cat. No: 354725) together with anti-human CD28 antibody (BD; Cat. No: 555725) to a final concentration of 2 µg/mL. Samples were either treated with vehicle (0.1%) or small chemical molecules of the indicated concentrations.

For end point determination of cytokine production the cells were incubated for 72 h at 37° C. and 5% $CO_2$. Supernatants were harvested and stored frozen at −80° C. until further processing. The cells were assayed for viability by incubation for 15 min with fluoresceindiacetate (5 µg/mL in PBS) and subsequent measurement of fluorescein (485 nm/535 nm).

Cytokine concentrations in the supernatants were determined in bead-based multiplex ELISA assays using Procarta Cytokine Assay Kits (Panomics) following the manufacturers instructions. The samples were read in a Luminex100 device and analysed with the IS Luminex 2.3 Software using a 5 parameter non-linear regression curve-fitting model.

Figure 2B:
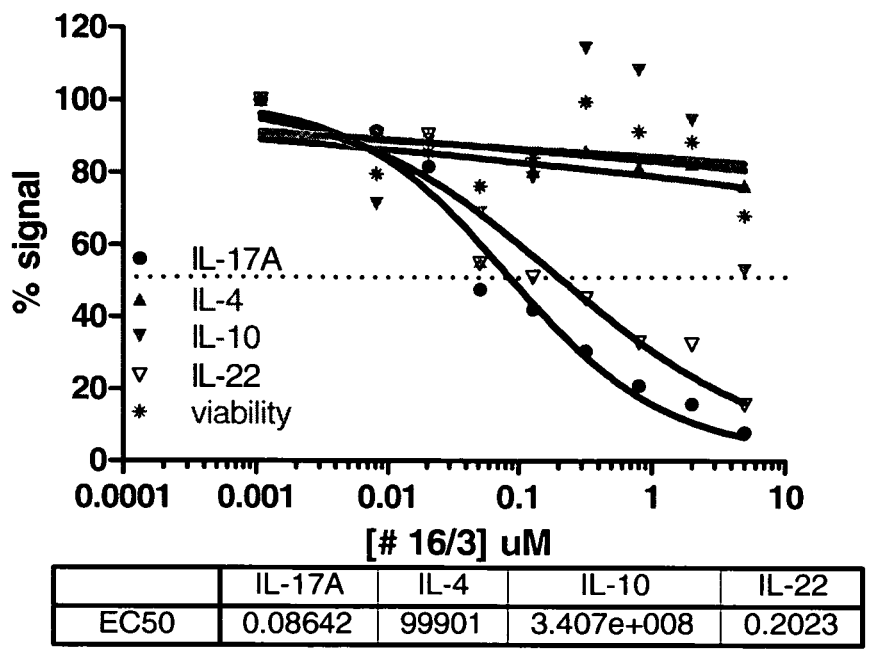
Figure 2B:
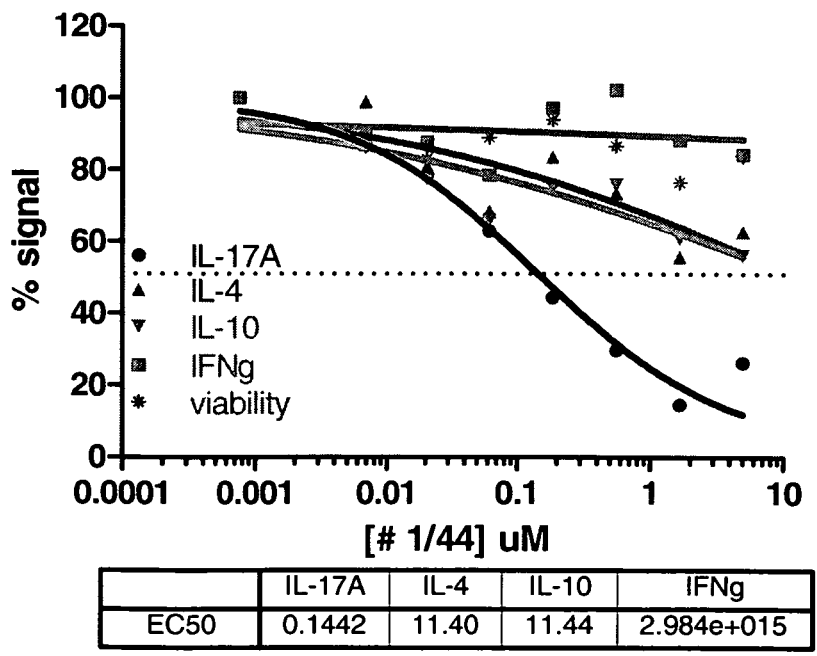

Production of Th17 indicator cytokines such as IL-17A and IL-22 as shown (but also of IL-21 and IL-17F) is inhibited with half effective inhibitory concentrations ($EC_{50}$s) ranging typically from 0.08 to 0.9 µM. The inhibitory efficacy of the molecules for these cytokines is in the range of 50-95%. Effects on cytokines like IFNγ produced mainly by Th1 cells; IL-4 (Th2 cells) or IL-10 (regulatory T cells) remain marginal. FIG. 2 illustrates the selective inhibitory effects on Th17-cytokine production in activated human PBMCs of Preparative Example 1, 16/4, 16/3 and 1/44.

In Vivo Assay for Suppression of IL-17 by RORγ Inverse Agonists

All animal models that mimic human autoimmune disease suffer from the issue that they are long lasting, require substantial amounts of exploratory drugs and do mostly not allow for monitoring IL-17 production in a simple setup. We therefore developed an in vivo assay based on an immunisation protocol that stems from a typical mouse Experimental Autoimmune Encephalomyelitis (EAE) model. Such EAE models employ the administration of certain autoimmunogenic peptides derived from i.e. Myelin Oligodendrocyte Glycoprotein (MOG) in conjunction with co-administration of a strong immune stimulants such as Complete Freund's Adjuvans (CFA) and a booster for T-cell activation such as *Pertussis* Toxin (PTX) to induce an autoimmune response. IL-17 producing Th17 cells are elevated under these conditions and about 14-21 days after the immunisation macroscopic signs of CNS inflammation such as impairment of movement become visible.

We used the same immunisation protocol not to induce the full symptoms of EAE but to prime and induce IL-17 production by Th17 cells and to demonstrate down-regulation of IL-17 in plasma by administration of an RORγ inverse agonist. Table 6 shows the immunisation, compound administration and blood sampling scheme:

TABLE 6

| | Day 0 | Day 1 | | | | Day 2 | | | | Day 3-17 | | |
|---|---|---|---|---|---|---|---|---|---|---|---|---|
| | 17:00 h | 9:00 h | 10:00 h | 12:00 h | 17:00 h | 17:30 h | 9:00 h | 10:00 h | 17:00 h | 17:30 h | 9:00 h | 17:00 h | 17:30 h |
| Drug i.p. injection 10 mpk i.p. | | X | | | | X | X | | | X | X | | X |
| (MOG)/CFA or PTX | | | (MOG)/ CFA | PTX | | | | PTX | | | | | |
| Blood sampling | X | | | | X | | | X | | | X | | |
| IL-x analysis IL-17, IFNγ, IL-2 | X | | | | X | | | X | | | X | | |
| Cpd levels | | | | | X | | | | X | | | [X] | |

This immunisation scheme, while disturbing the regular development of macroscopic EAE symptoms in mice, allows for the monitoring of proinflammatory cytokines in plasma, specifically for IL-17, IL-2 and Interferon gamma IFNγ.

For this protocol, 10-14 weeks old C57/bl6 mice (breeder: Janvier) were immunised with MOG peptide plus CFA in a pre-filled syringe (MOG 35-55 in CFA emulsion; Catalogue No. EK-0114 with PTX 3,75x, Hooke Laboratories, EAE induction kit) and CFA without MOG (Catalogue No. CK-5114, Hooke Laboratories) as well as untreated mice were used as controls. The immunisation was enhanced by administration of a fixed dose of *Pertussis* Toxin (PTX) on the same day and one day after the priming immunisation according to the manufacturer's instructions. Starting with day 0 (one day prior to immunisation) daily blood samples from the same time of the day were obtained and subjected to plasma cytokine analysis (Bio Plex x-plex assays for murine IL-17, IFNγ, IL-2 used in a Luminex® 200 instrument according to the manufacturer's instructions). The drug injection was performed at doses of 2×10 mg/(kg×day) intraperitoneally. The test article was dissolved in DMSO and then diluted into sterile saline (0.9% NaCl)+0.1% Tween 80 up to a final concentration of DMSO of maximal 5%.

Results from this in vivo assay using the compound of Preparative Example 1/8 as drug are shown in FIG. 1. It can be taken from FIG. 1 that the IL-17 peaks are nearly completely reduced upon Preparative Example 1/8 dosing. The reduction of IL-17 and the increase of IFNγ upon Preparative Example 1/8 dosing shows the shift from a Th17 to a Th1 driven immune response thereby demonstrating the impact of down-regulating RORγ activity in vivo.

The invention claimed is:
1. A compound represented by Formula (1)

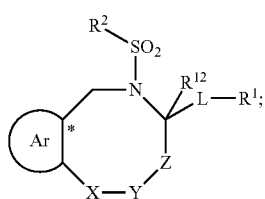

or an enantiomer, diastereomer or tautomer thereof, or a pharmaceutically acceptable salt thereof,
wherein:
$R^1$ is hydrogen; $C_{1-12}$-alkyl; $C_{1-12}$-alkenyl; $C_{1-12}$-alkynyl; $C_{3-10}$-cycloalkyl; $COOC_{1-6}$-alkyl; $CONR^{10}R^{11}$; CN; $NR^{10}R^{11}$; a saturated 3-10 membered heterocycle containing 1 or 2 heteroatoms independently selected from the group consisting of N, O and S; a 5-10 membered mono- or bicyclic heteroaromatic ring system containing 1, 2, 3 or 4 heteroatoms independently selected from the group consisting of N, O and S; or a 6-10 membered mono- or bicyclic aromatic ring system;
wherein the alkyl, the alkenyl, the alkynyl, the cycloalkyl and the heterocyclic groups are unsubstituted or substituted by 1, 2 or 3 substituents independently selected from the group consisting of hydroxy, oxo, halogen, cyano, halo-$C_{1-6}$-alkyl, O—$C_{1-6}$-alkyl, O-(halo-$C_{1-6}$-alkyl), $CONR^{10}R^{11}$ and $NR^{10}R^{11}$;
and wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{1-12}$-alkyl, $C_{3-6}$-cycloalkyl, O—$C_{1-6}$-alkyl, O-(halo-$C_{1-6}$-alkyl), COOH, $CO_2NR^{10}R^{11}$, $NR^{10}R^{11}$, a 5-10 membered mono- or bicyclic heteroaromatic ring system containing 1, 2 or 3 heteroatoms independently selected from the group consisting of N, O and S, a 6-10 membered mono- or bicyclic aromatic ring system, and a saturated 3-8 membered heterocycle containing 1 or 2 heteroatoms independently selected from the group consisting of N, O and S;
wherein the ring systems, the alkyl and the cycloalkyl groups are independently from each other unsubstituted or substituted by 1, 2 or 3 substituents selected from the group consisting of hydroxy, oxo, halogen, cyano, $C_{1-6}$-alkyl, halo-$C_{1-6}$-alkyl, O—$C_{1-6}$-alkyl, O-(halo-$C_{1-6}$-alkyl) and COOH;
or wherein the heteroaromatic and the aromatic ring systems are fused with a saturated 5-8 membered heterocycle containing 1, 2, or 3 heteroatoms independently selected from the group consisting of N, O and S;
wherein the fused ring system is unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, $CO_2NR^{10}R^{11}$ and $NR^{10}R^{11}$;
$R^2$ is $C_{1-12}$-alkyl; $C_{3-10}$-cycloalkyl; a saturated 3-10 membered heterocycle containing 1 or 2 heteroatoms independently selected from the group consisting of N, O and S; a 5-10 membered mono- or bicyclic heteroaromatic ring system containing 1, 2 or 3 heteroatoms independently selected from the group consisting of N, O and S; or a 6-10 membered mono- or bicyclic aromatic ring system;
wherein the alkyl, the cycloalkyl and the heterocycle groups are unsubstituted or substituted by 1, 2 or 3 substituents independently selected from the group consisting of hydroxy, oxo, halogen, cyano, halo-$C_{1-6}$-alkyl, O—$C_{1-6}$-alkyl, O-(halo-$C_{1-6}$-alkyl), COOH, $CONR^{10}R^{11}$ and $NR^{10}R^{11}$;
and wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{1-12}$-alkyl, $C_{3-6}$-cycloalkyl, O—$C_{1-6}$-alkyl, O-(halo-$C_{1-6}$-alkyl), O—$C_{1-6}$-alkyl substituted with a saturated 5 or 6 membered heterocycle containing 1 or 2 heteroatoms independently selected from the group consisting of N, O and S, COOH, $CO_2(C_{1-6}$-alkyl), $CONR^{10}R^{11}$, $NR^{10}R^{11}$, $SO_2(C_{1-6}$-alkyl), a saturated 3-10 membered heterocycle containing 1 or 2 heteroatoms independently selected from the group consisting of N, O and S, a 5-10 membered mono- or bicyclic heteroaromatic ring system containing 1, 2 or 3 heteroatoms independently selected from the group consisting of N, O and S, and a 6-10 membered mono- or bicyclic aromatic ring system;
wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, $CO_2NR^{10}R^{11}$ and $NR^{10}R^{11}$;
or wherein the heteroaromatic and the aromatic ring systems are fused with a saturated 5-8 membered heterocycle containing 1, 2, or 3 heteroatoms independently selected from the group consisting of N, O and S;
wherein the fused ring system is unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, $CO_2NR^{10}R^{11}$ and $NR^{10}R^{11}$;
L is —$(CR^6{}_2)_x$—, —$NR^7$—$(CR^6{}_2)_x$—, —$(CR^6{}_2)_x$—$NR^7$—, —$(CR^6{}_2)_x$—O—, or —$(CR^6{}_2)_x$—O—$(CR^6{}_2)_x$—;
$R^6$ is independently H, $C_{1-6}$-alkyl, halo-$C_{1-6}$-alkyl or halogen;
$R^7$ is H, $C_{1-6}$-alkyl, halo-$C_{1-6}$-alkyl and hydroxy-$C_{1-6}$-alkyl;
$R^{10}$ and $R^{11}$ in each occurrence are independently selected from hydrogen, $C_{1-6}$-alkyl, halo-$C_{1-6}$-alkyl, $C_{3-6}$-cycloalkyl; or $R^{10}$ and $R^{11}$ when taken together with the nitrogen to which they are attached complete a 3- to 8-membered ring containing carbon atoms and optionally containing a heteroatom selected from O, S, SO, $SO_2$ or $NR^7$, wherein the ring is unsubstituted or substituted with one or more halogen, oxo or $C_{1-6}$-alkyl;

$R^{12}$ is H, $C_{1-6}$-alkyl or halo-$C_{1-6}$-alkyl;

x is independently 1, 2, 3 or 4;

Ar is phenyl unsubstituted or substituted by 1, 2 or 3 substituents independently selected from the group consisting of hydroxy, halogen, cyano, halo-$C_{1-6}$-alkyl, $C_{1-6}$-alkyl, $C_{3-6}$-cycloalkyl, O—$C_{1-6}$-alkyl, O-(halo-$C_{1-6}$-alkyl), COOH, $CO_2NR^{10}R^{11}$, $NR^{10}R^{11}$, a saturated 3-10 membered heterocycle containing 1 or 2 heteroatoms independently selected from the group consisting of N, O and S, a 5-10 membered mono- or bicyclic heteroaromatic ring system containing 1, 2 or 3 heteroatoms independently selected from the group consisting of N, O and S and a 6-10 membered mono- or bicyclic aromatic ring system;

wherein the heteroaromatic and aromatic ring system is unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl and COOH;

X is $CH_2$, $C(CH_3)_2$ or CO;

Y is O;

Z is $CH_2$, $C(CH_3)_2$ or CO;

wherein combinations of X, Y and Z where O is directly connected to CO are excluded.

2. The compound according to claim 1, wherein:

$R^1$ is $C_{1-12}$-alkyl; $C_{3-6}$-cycloalkyl; a saturated 3-8 membered heterocycle containing 1 or 2 heteroatoms independently selected from the group consisting of N, O and S; a 5-10 membered mono- or bicyclic heteroaromatic ring system containing 1, 2 or 3 heteroatoms independently selected from the group consisting of N, O and S; or a 6-10 membered mono- or bicyclic aromatic ring system;

wherein the heteroaromatic and the aromatic ring systems are independently from each other unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl, COOH, a 5-10 membered mono- or bicyclic heteroaromatic ring system containing 1, 2 or 3 heteroatoms independently selected from the group consisting of N, O and S, and a 6-10 membered mono- or bicyclic aromatic ring system;

wherein the heteroaromatic and the aromatic ring systems are independently from each other unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl and COOH;

or wherein the heteroaromatic and the aromatic ring systems are fused with a saturated 5-8 membered heterocycle containing 1, 2, or 3 heteroatoms independently selected from the group consisting of N, O and S;

wherein the fused ring system is unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl and COOH;

$R^2$ is $C_{1-12}$-alkyl; $C_{3-6}$-cycloalkyl; a saturated 3-8 membered heterocycle containing 1 or 2 heteroatoms independently selected from the group consisting of N, O and S; a 5-10 membered mono- or bicyclic heteroaromatic ring system containing 1, 2 or 3 heteroatoms independently selected from the group consisting of N, O and S; or a 6-10 membered mono- or bicyclic aromatic ring system;

wherein the heteroaromatic and the aromatic ring systems are independently from each other unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl, COOH, a 5-10 membered mono- or bicyclic heteroaromatic ring system containing 1, 2 or 3 heteroatoms independently selected from the group consisting of N, O and S, and a 6-10 membered mono- or bicyclic aromatic ring system;

wherein the heteroaromatic and the aromatic ring systems are independently from each other unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl and COOH;

or wherein the heteroaromatic and the aromatic ring systems are fused with a saturated 5-8 membered heterocycle containing 1, 2, or 3 heteroatoms independently selected from the group consisting of N, O and S;

wherein the fused ring system is unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl and COOH;

L is —$(CR^6{}_2)_x$—, —$NR^7$—$(CH_2)_x$—, —$(CH_2)_x$—$NR^7$— or —$(CH_2)_x$—O—;

$R^6$ is independently H, $C_{1-6}$-alkyl or halogen;

$R^7$ is H or $C_{1-4}$-alkyl;

$R^{12}$ is H;

x is 1, 2, 3 or 4;

Ar is phenyl unsubstituted or substituted by 1, 2 or 3 substituents independently selected from the group consisting of hydroxy, halogen, cyano, halo-$C_{1-12}$-alkyl, $C_{1-6}$-alkyl, $C_{3-6}$-cycloalkyl, O—$C_{1-6}$-alkyl, COOH, a 5-10 membered mono- or bicyclic heteroaromatic ring system containing 1, 2 or 3 heteroatoms independently selected from the group consisting of N, O and S and a 6-10 membered mono- or bicyclic aromatic ring system;

wherein the heteroaromatic and aromatic ring system is unsubstituted or substituted by 1, 2 or 3 substituents independently selected from the group consisting of hydroxy, oxo, halogen, cyano, halo-$C_{1-12}$-alkyl, $C_{1-6}$-alkyl, $C_{3-6}$-cycloalkyl, O—$C_{1-6}$-alkyl and COOH;

X is $CH_2$, $C(CH_3)_2$ or CO;

Y is O;

Z is $CH_2$, $C(CH_3)_2$ or CO;

wherein combinations of X, Y and Z where O is directly connected to CO are excluded.

3. The compound according to claim 1 wherein:

X is $CH_2$;

Z is $CH_2$;

L is —$CH_2$—, —$CH_2O$— and —$CH_2OCH_2$—; and;

Ar is phenyl unsubstituted or substituted by 1, 2, or 3 substituents independently selected from the group consisting of hydroxy, halogen, cyano, $C_{1-6}$-alkyl, halo-$C_{1-6}$-alkyl, $C_{3-6}$-cycloalkyl, O—$C_{1-6}$-alkyl, and halo-($C_{1-6}$-alkyl).

4. The compound according to claim 1 wherein:

X is $CH_2$;

Z is $CH_2$;

L is —$CH_2$—, —$CH_2O$— and —$CH_2OCH_2$—;

$R^2$ is a 5-10 membered mono- or bicyclic heteroaromatic ring system containing 1, 2 or 3 heteroatoms independently selected from the group consisting of N, O and S; or a 6-10 membered mono- or bicyclic aromatic ring system;

wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, $CO_2$($C_{1-6}$-alkyl), $CONR^{10}R^{11}$, $NR^{10}R^{11}$, $SO_2$($C_{1-6}$-alkyl), a saturated 3-10 membered heterocycle containing 1 or 2 heteroatoms independently selected from the group consisting of N, O and S, a 5-10 membered mono- or bicyclic heteroaromatic ring system containing 1, 2 or 3 heteroatoms independently selected from the group consisting of N, O and S, and a 6-10 membered mono- or bicyclic aromatic ring system;

wherein the heteroaromatic and the aromatic ring systems are independently from each other unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, $CO_2NR^{10}R^{11}$ and $NR^{10}R^{11}$;

or wherein the heteroaromatic and the aromatic ring systems are fused with a saturated 5-8 membered heterocycle containing 1, 2, or 3 heteroatoms independently selected from the group consisting of N, O and S;

wherein the fused ring system is unsubstituted or substituted by 1, 2 or 3 substituents independently selected from the group consisting of hydroxy, oxo, halogen, cyano, $C_{1-6}$-alkyl, halo-$C_{1-6}$-alkyl, $C_{3-6}$-cycloalkyl, O—$C_{1-6}$-alkyl, O-(halo-$C_{1-6}$-alkyl), COOH, $CO_2NR^{10}R^{11}$ and $NR^{10}R^{11}$.

5. The compound according to claim 1 wherein:
X is $CH_2$;
Z is $CH_2$;
L is —$CH_2$—, —$CH_2O$— and —$CH_2OCH_2$—;
$R^1$ is $C_{1-12}$-alkyl; $C_{3-10}$-cycloalkyl or a 6-membered aromatic ring system;
wherein the alkyl and the cycloalkyl groups are unsubstituted or substituted by 1, 2 or 3 substituents independently selected from the group consisting of halogen, cyano, halo-$C_{1-6}$-alkyl, O—$C_{1-6}$-alkyl and O-(halo-$C_{1-6}$-alkyl);
and wherein the 6-membered aromatic ring system is unsubstituted or substituted by 1, 2 or 3 substituents independently selected from the group consisting of halogen, cyano, $C_{1-6}$-alkyl, halo-$C_{1-6}$-alkyl, O—$C_{1-6}$-alkyl and O-(halo-$C_{1-6}$-alkyl).

6. The compound according to claim 1 wherein Y is O.

7. The compound according to claim 1 wherein:
X is $CH_2$;
Y is O;
Z is $CH_2$;
L is —$CH_2$—, —$CH_2O$— and —$CH_2OCH_2$—;
Ar is phenyl unsubstituted or substituted by 1, 2, or 3 substituents independently selected from the group consisting of hydroxy, halogen, $C_{1-4}$-alkyl, halo-$C_{1-4}$-alkyl, O—$C_{1-4}$-alkyl, and halo-($C_{1-4}$-alkyl);
$R^1$ is $C_{1-12}$-alkyl; $C_{3-10}$-cycloalkyl; a 5 to 6-membered monocyclic heteroaromatic ring system containing 1, 2, 3 or 4 heteroatoms independently selected from the group consisting of N, O and S; or a 6-membered monoaromatic ring system;
wherein $C_{1-12}$-alkyl, $C_{3-10}$-cycloalkyl, a 5 to 6-membered monocyclic heteroaromatic ring system containing 1, 2, 3 or 4 heteroatoms independently selected from the group consisting of N, O and S, and a 6-membered monoaromatic ring system is optionally substituted by 1, 2 or 3 substituents independently selected from the group consisting of hydroxy, oxo, halogen, halo-$C_{1-6}$-alkyl, O—$C_{1-6}$-alkyl, and O-(halo-$C_{1-6}$-alkyl);

$R^2$ is a 10-membered bicyclic heteroaromatic ring system containing 1, 2 or 3 heteroatoms independently selected from the group consisting of N, O and S; or a 6-membered monoaromatic ring system;

wherein the heteroaromatic and the aromatic ring systems are independently from each other unsubstituted or substituted by 1, 2 or 3 substituents independently selected from the group consisting of halogen, $C_{1-6}$-alkyl, halo-$C_{1-6}$-alkyl, $C_{3-6}$-cycloalkyl, O—$C_{1-6}$-alkyl, and O-(halo-$C_{1-6}$-alkyl).

8. The compound according to claim 1 wherein:
X is $CH_2$;
Y is O;
Z is $CH_2$;
Ar is phenyl unsubstituted or substituted by 1, 2, or 3 substituents independently selected from the group consisting of hydroxy, halogen, $C_{1-4}$-alkyl, halo-$C_{1-4}$-alkyl, O—$C_{1-4}$-alkyl, and halo-($C_{1-4}$-alkyl);
L-$R^1$ is selected from:

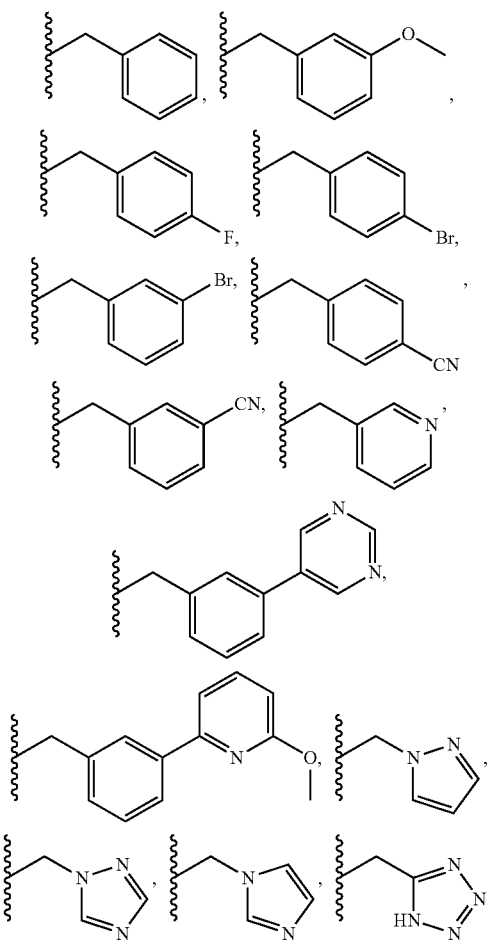

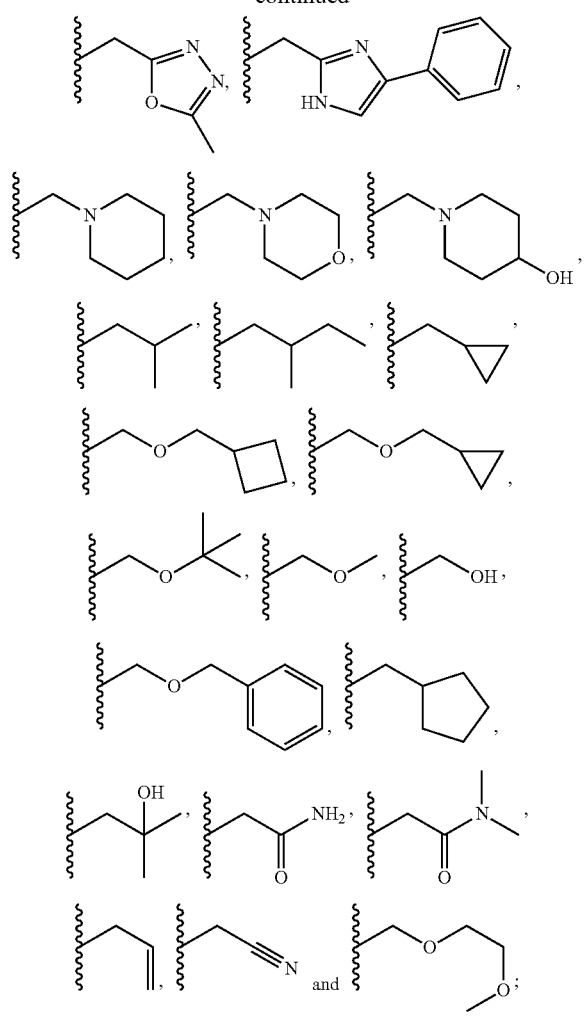
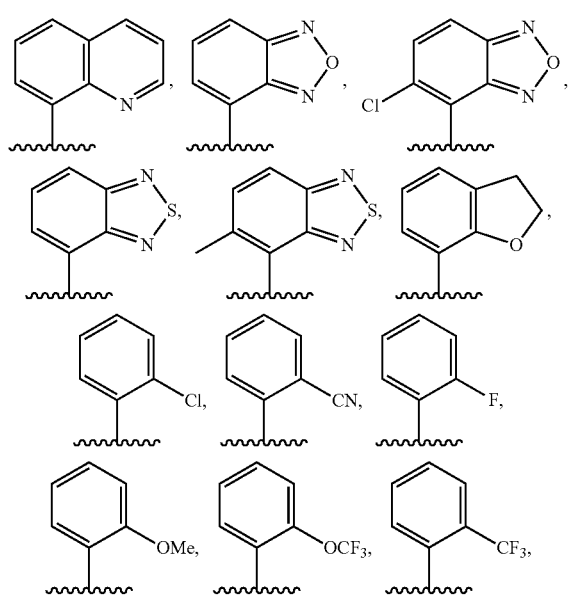
R² is selected from:
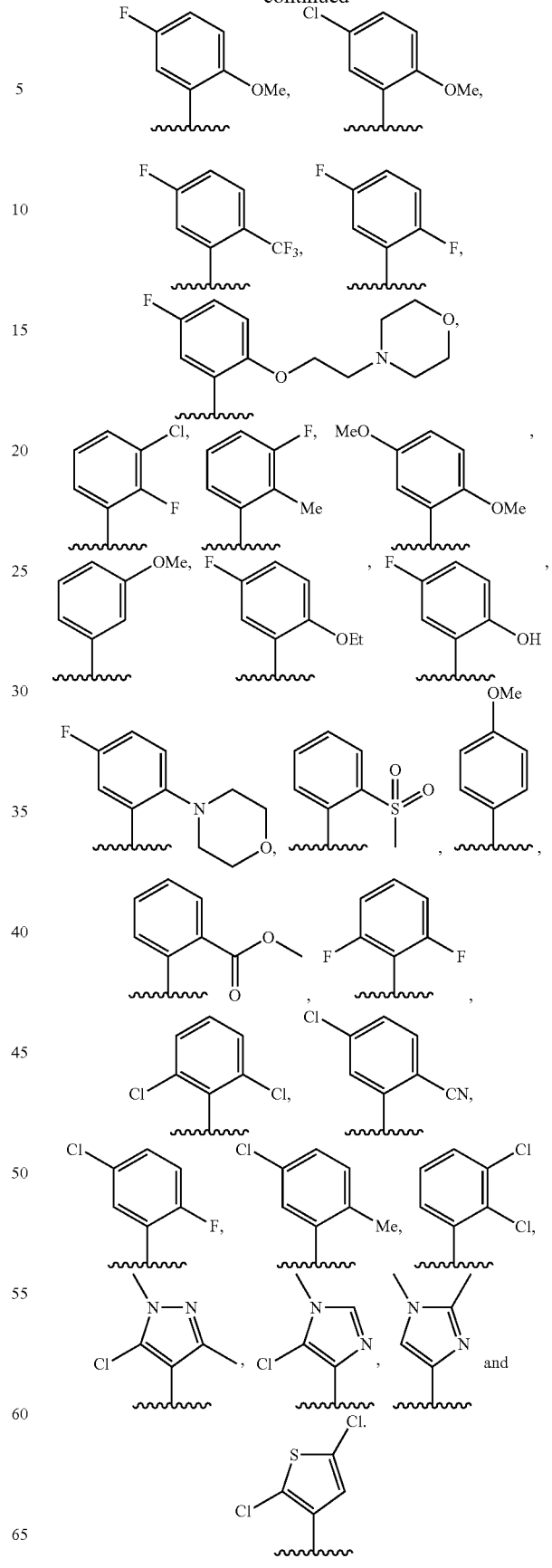

9. The compound according to claim 1 selected from:
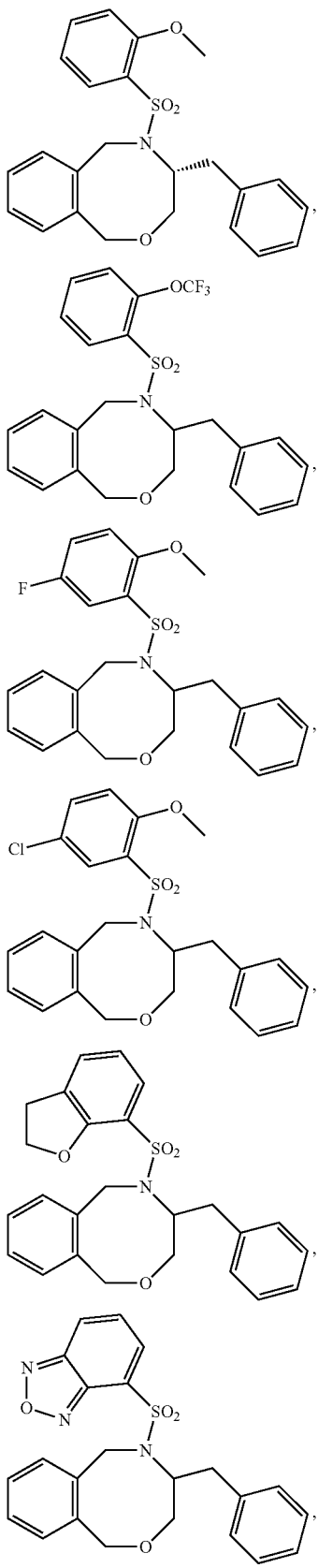
-continued
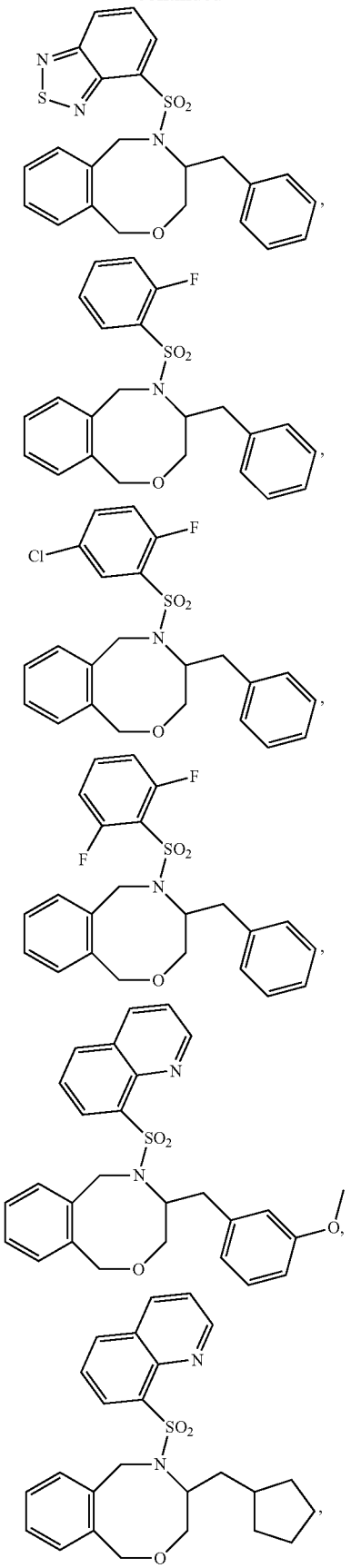

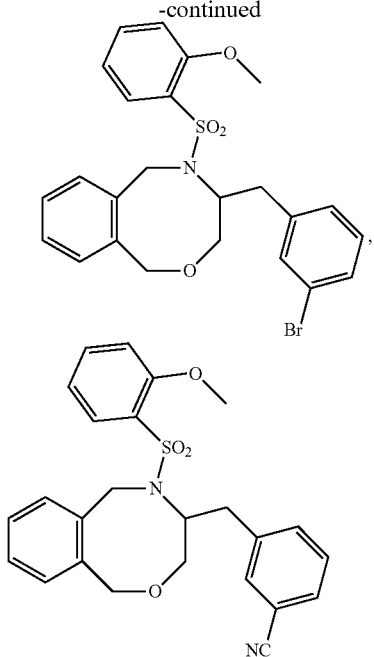
and
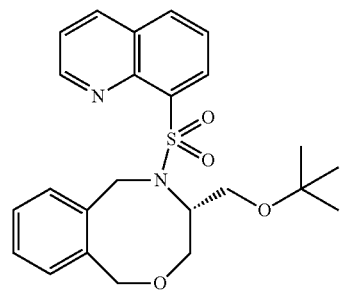
or an enantiomer, diastereomer or tautomer thereof, or a pharmaceutically acceptable salt thereof.
10. A pharmaceutical composition comprising a compound according to claim 1, or an enantiomer, diastereomer or tautomer thereof, or a pharmaceutically acceptable salt thereof, and a pharmaceutically acceptable carrier.
* * * * *